US011542481B2

(12) United States Patent
Kutchan et al.

(10) Patent No.: US 11,542,481 B2
(45) Date of Patent: Jan. 3, 2023

(54) MORPHINAN N-DEMETHYLASE ISOLATED FROM THE METHYLOBACTERIUM THEBAINFRESSER AND METHODS OF USE THEREOF

(71) Applicant: DONALD DANFORTH PLANT SCIENCE CENTER, St. Louis, MO (US)

(72) Inventors: Toni Kutchan, St. Louis, MO (US); Megan Augustin, St. Louis, MO (US)

(73) Assignee: DONALD DANFORTH PLANT SCIENCE CENTER, St. Louis, MO (US)

(*) Notice: Subject to any disclaimer, the term of this patent is extended or adjusted under 35 U.S.C. 154(b) by 597 days.

(21) Appl. No.: 16/479,085

(22) PCT Filed: Jan. 18, 2018

(86) PCT No.: PCT/US2018/014271
§ 371 (c)(1),
(2) Date: Jul. 18, 2019

(87) PCT Pub. No.: WO2018/136654
PCT Pub. Date: Jul. 26, 2018

(65) Prior Publication Data
US 2019/0352618 A1 Nov. 21, 2019

Related U.S. Application Data

(60) Provisional application No. 62/448,164, filed on Jan. 19, 2017.

(51) Int. Cl.
C12P 17/18 (2006.01)
C12N 9/02 (2006.01)
C12N 15/82 (2006.01)

(52) U.S. Cl.
CPC ....... *C12N 9/0071* (2013.01); *C12N 15/8243* (2013.01); *C12P 17/18* (2013.01); *C12Y 114/11* (2013.01)

(58) Field of Classification Search
None
See application file for complete search history.

(56) References Cited

U.S. PATENT DOCUMENTS

| 4,115,389 A | 9/1978 | Monkovic |
| 2007/0020624 A1 | 1/2007 | Rubenfield et al. |
| 2010/0087647 A1 | 4/2010 | Allen et al. |
| 2013/0332133 A1 | 12/2013 | Horn et al. |
| 2014/0227729 A1 | 8/2014 | Subramanian et al. |
| 2014/0329846 A1 | 11/2014 | Tung |
| 2019/0144900 A1* | 5/2019 | Smolke ................ C12N 9/0006 435/118 |
| 2019/0352618 A1 | 11/2019 | Kutchan et al. |

FOREIGN PATENT DOCUMENTS

| WO | 2011032214 A1 | 3/2011 |
| WO | 2016/039961 A1 | 3/2016 |

OTHER PUBLICATIONS

Singh et al., Curr. Protein Pept. Sci. 18:1-11, 2017 (Year: 2017).*
Zhang et al., Structure 26:1474-1485, 2018 (Year: 2018).*
Wu et al., Mol. Cell. Biol. 15:264-271, 1995 (Year: 1995).*
Tran et al., ACS Catalysis 1:956-968, 2011 (Year: 2011).*
Werner et al., Adv. Synth. Catal. 354:2706-2712, 2012 (Year: 2012).*
Augustin et al., Nat. Sustain. 2:465-474, 2019 (Year: 2019).*
Augustin et al., "Production of Mon-and Sesquiterpenes in *Camelina sativa* Oilseed", Planta, 2015, pp. 693-708, vol. 242.
Bolger et al., "Trimmomatic: A Flexible Trimmer for Illumina Sequence Data", Bioinformatics, 2014, pp. 2114-2120, vol. 30, Issue 15, Oxford University Press.
Brummell et al., "Probing the Combining Site of an Anti-Carbohydrate Antibody by Saturation-Mutagenesis: Role of the Heavy-Chain CDR3 Residues", Biochemistry, 1993, pp. 1180-1187, vol. 32, The American Chemical Society.
Burks et al., "In Vitro Scanning Saturation Mutagenesis of an Antibody Binding Pocket", Proc. National Academy of Sciences of the USA, 1997, pp. 412-417, vol. 94.
Burriesci et al., "Fulcrum: Condensing Redundant Reads from High-Throughput Sequencing Studies", Bioinformatics, 2012, pp. 1324-1327, vol. 28, Issue 10, Oxford University Press.
Camacho et al., "BLAST+: Architecture and Applications", BMC Bioinformatics, 2009, pp. 1-9, vol. 10, Issue 421.
Cooley et al., "Amine Dealkylations with Acyl Chlorides", Jan. 1989, pp. 1-7.
Finn et al., "The Pfam Protein Families Database: Towards a More Sustainable Future", Nucleic Acids Research, 2016, pp. D279-D285, vol. 44, Oxford University Press.
Giannoukos et al., "Efficient and Robust RNA-seq Process for Cultured Bacteria and Complex Community Transcriptomes", Genome Biology, 2012, pp. 1-13.
Grabherr et al., "Trinity: Reconstructing a Full-Length Transcriptome Without a Genome from RNA-Seq Data", National Biotechnology, 2013, pp. 1-25, vol. 29, No. 7.
Karlin et al., "Applications and Statistics for Multiple High-Scoring Segments in Molecular Sequences", Proc. National Academy of Sciences of the USA, Jun. 1993, pp. 5873-5877, vol. 90.
Kobayashi et al., "Tryptophan H33 Plays an Important Role in Pyrimidine (6-4) Pyrimidone Photoproduct Binding by a High-Affinity Antibody", Protein Engineering, 1999, pp. 879-884, vol. 12, Issue 10.
Li et al., "Fast and Accurate Short Read Alignment with Burrows-Wheeler Transform", Bioinformatics, 2009, pp. 17541760, vol. 25, Issue 14.
Lu et al., "Generation of Transgenic Plants of a Potential Oilseed Crop *Camelina sativa* by Agrobacterium-Mediated Transformation", Plant Cell Rep., 2008, pp. 273-278, vol. 27.

(Continued)

*Primary Examiner* — David Steadman
(74) *Attorney, Agent, or Firm* — Thompson Coburn LLP; William A. Holtz

(57) ABSTRACT

Disclosed herein are methods for N-demethylating an N-methylated compound using an enzymatic reaction, rather than, e.g. a chemical modification. Also provided herein are enzymes for performing the reaction.

17 Claims, 30 Drawing Sheets

Specification includes a Sequence Listing.

(56) References Cited

OTHER PUBLICATIONS

Madyastha et al., Mucor Piriformis, An Efficient N-Dealkylating Reagent for Thebaine and its N-Variants, Journal of Chemical Society. Perkins Transaction !, 1994, 911-912, Issue 8.

Madyastha, "Preparatively Useful Transformations of Steriods and Morphine Alkaloids by Mucor Piriformis", Proceedings of the Indian Academy of Science, Oct. 1994, pp. 1203-1212, vol. 106, Issue 5.

McCamley et al., "Efficient N-Demethylation of Opiate Alkaloids Using Modified Nonclassical Polonovski Reaction", Journal of Organic Chemistry, 2003, pp. 9847-9850, vol. 68, Issue 25.

Mockler et al., "The Diurnal Project Diurnal and Circadian Expression Profiling, Model-Based Pattern Matching, and Promoter Analysis", Cold Spring Harbor Symposia on Quantitative Biology, 2007, pp. 353-363, vol. 72.

Paoni et al., "Permeabilization of Cells for Studies on the Biochemistry of Bacterial Chemotaxis", Proc. National Academy of Sciences of the USA, Aug. 1979, pp. 3693-3697, vol. 76, Issue 8.

Pham et al., "Green Chemistry Studies on the Oxidative N-Demethylation of Atropine, Thebaine and Oxycodone Using a Fe III—TAML Catalyst", Green Chemistry, Mar. 2014, pp. 1399-1409, vol. 16.

Rice et al., "Procedural Refinements in the N-Demethylation of Morphine and Codeine Using Phenyl Chloroformate and Hydrazine", J. Hetercyclic Chem., 1977, pp. 665-666, vol. 14.

Rice, "An Improved Procedure for the N-Demethylation of 6,7-Benzomorphans, Morphine, and Codeine", J. Org. Chem., 1975, pp. 1850-1851, vol. 40, Issue 12.

Ripper et al., "Photochemical N-Demethylation of Alkaloids", Bioorganic & Medicinal Chemistry Letters, 2001, pp. 443-445, vol. 11.

Schwab, "14-(Arylhydroxyamino) Codeinones and Derivatives as Analgetics an Antagonists", J. Med. Chem., 1980, pp. 698-702, vol. 23.

Smith et al., "Electrochemical Dealkylation of Aliphatic Amines", The Journal of Organic Chemistry, Jun. 1969, pp. 1821-1826, vol. 34, Issue 6.

Tamura et al., "MEGA6: Molecular Evolutionary Genetics Analysis Version 6.0", Molecular Biology and Evolution, 2013, pp. 2725-2729, vol. 30, Issue 12, Oxford University Press.

Thavaneswaran et al., "Further Investigation of the N-Demethylation of Tertiary Amine Alkaloids Using the Non-Classical Polonovski Reaction", Bioorganic & Medicinal Chemisty Letters, Jun. 2006, pp. 2868-2871, vol. 16, Issue 11.

Thavaneswaran et al., "N-Demethylation of Alkaloids", National Product Communications, Jul. 2006, pp. 885-897, vol. 1, Issue 10.

William S. et al., "Bacterial Genomic DNA Isolation Using CTAB", Protocol, JGI Doe Joint Genome Institute, US Department of Energy, 2012, 4 pages.

* cited by examiner

MORPHINAN N-DEMETHYLASE ISOLATED FROM THE METHYLOBACTERIUM THEBAINFRESSER AND METHODS OF USE THEREOF

CROSS-REFERENCE TO RELATED APPLICATIONS

This application is a 35 U.S.C. § 371 U.S. National Stage application of International Patent Application No. PCT/US2018/014271, filed Jan. 18, 2018, which claims the benefit of U.S. Provisional Patent Application Ser. No. 62/488,164, filed Jan. 19, 2017, both of which are incorporated by reference in their entireties.

INCORPORATION OF SEQUENCE LISTING

The sequence listing that is contained in the file named "DDSC_47004_158297_Sequence Listing_ST25.txt", which is 12,707 bytes (measured in operating system MS-Windows), created on Jan. 18, 2017, is filed herewith by electronic submission and incorporated herein by reference in its entirety.

BACKGROUND

Naturally occurring opiates such as thebaine, morphine, and codeine are N-methylated. The N-demethylation of such opiates is a key chemical transformation in the synthesis of synthetic opiates. To date, commercial N-demethylation methods are chemical in nature and typically require toxic and expensive reagents while low in yield (WO 2011/032214A1). The naturally occurring alkaloids atropine, scopolamine, and cocaine, along with the opiate morphine all contain a tertiary N-methylamine group. Modification of the N-methylamine group alters the pharmacological properties of these alkaloids. This can lead to the production of many important pharmaceutical compounds. (Do Pham, D D et al. *Green Chem.*, 2014, 16, 1399-1409).

For example, the opiate thebaine is a synthetic precursor for the analgesic oxycodone and the intermediate oxymorphone, which is used to prepare the N-methylcyclobutyl-based analgesic nalbuphine and the N-methylcyclopropyl-based opioid antagonists naltrexone, buprenorphine, nalmefene, and the allyl-based naloxone used in the treatment of alcohol or opiate dependence and for rapid opiate detoxification. (Do Pham, D D et al. *Green Chem.*, 2014, 16, 1399-1409; *National Academies of Sciences, Engineering, and Medicine.* 2017. *Pain management and the opioid epidemic: Balancing societal and individual benefits and risks of prescription opioid use.* Washington, D.C.: The National Academies Press; Allen, B. E., et al., U.S. Patent Application Publication No. 2010/0087647 A1).

While many methods of N-demethylating opiates have been described, including the use of chemical reagents, and procedures utilizing photochemistry, electrochemistry, and microorganisms, enzymatic N-demethylation has not been widely described (J. von Braun, *Chem. Ber.* 1909, 42, 2035; J. H. Cooley, E. J. Evain, *Synthesis* 1989, 1; K. C. Rice, *J. Org. Chem.* 1975, 40, 1850; (c) K. C. Rice, E. L. May, *J. Heterocycl. Chem.* 1977, 14, 665; L. S. Schwab, *J. Med. Chem.* 1980, 23, 698; H. Merz, K. H. Pook, *Tetrahedron* 1970, 26, 1727; J. A. Ripper, E. R. T. Tiekink, P. J. Scammells, Bioorg. *Med. Chem. Lett.* 2001, 77, 443; P. J. Smith, C. K. Mann, *J. Org. Chem.* 1969, 34, 1821; J. E. Barry, M. Finkelstein, E. A. Mayeda, S. D. Ross, *J. Org. Chem.* 1974, 39, 3488; K. M. Madyastha, *Proc. Indian Acad. Sci.* 1994, 106, 1203; K. M. Madyastha, G. V. B. Reddy, *J. Chem. Soc*, Perkin Trans. 1 1994, 91 1; K. McCamley, J. A. Ripper, R. D. Singer, P. J. Scammells, *J. Org. Chem.* 2003, 68, 9847-9850; S. Thavaneswaran, P. J. Scammells, Bioorg. *Med. Chem. Lett.* 2006, 76, 2868-2871; S. Thavaneswaran, K. McCamley, P. J. Scammells, *Nat. Prod. Commun.* 2006, 7(10), 885-897).

Thus, there is a need to develop clean and efficient methods of N-demethylating opiates—as well as other drug classes such as the tropane alkaloids—for use in among other things, synthetic opiate production and new drug discovery.

SUMMARY

Provided for herein are methods for N-demethylating a low molecular weight N-methylated compound. In certain aspects, the methods comprise incubating the N-methylated compound with an enzyme comprising N-demethylase activity, wherein the enzyme is a morphinan N-demethylase (MND) identified from the *Methylobacterium* Thebainfresser having N-demethylase activity. In certain aspects, the enzyme is a fragment or variant (including derivatives) thereof having N-demethylase activity. In certain aspects, the enzyme is a fragment or variant (including derivatives) thereof having N-demethylase activity containing a cofactor, such as for example, flavin adenine dinucleotide (FAD). Said incubation converts the low molecular weight N-methylated compound into an N-demethylated compound. In certain aspects, the N-methylated compound is of natural or synthetic origin. In certain aspects, the MND enzyme or fragment or variant thereof is isolated, purified, or isolated and purified. In certain aspects, the MND enzyme or fragment or variant thereof further comprises one or more of benzylisoquinoline alkaloid N-demethylase activity, tropane alkaloid N-demethylase activity, pyrroloindole alkaloid N-demethylase activity, piperidine alkaloid N-demethylase activity, aporphine alkaloid N-demethylase activity, indole alkaloid N-demethylase activity, or Amaryllidaceae alkaloid N-demethylase activity. In certain aspects, the MND enzyme or fragment or variant (including derivatives) thereof performs the reaction in the presence of a solvent. In certain aspects, the MND enzyme or fragment or variant (including derivatives) thereof performs the reaction in the presence of a nonpolar solvent (e.g., chloroform), an aprotic polar solvent (e.g., tetrahydrofuran), and/or a polar protic solvent (e.g, methanol). In certain aspects, the MND enzyme or fragment or variant thereof has a $V_{max}$ of about 0.32 pmol s$^{-1}$, $K_m$ of about 0.97 µM, and/or a $K_{cat}$ of about 6.5×10$^{-4}$ s$^{-1}$, when thebaine is the substrate. In certain aspects, the N-methylated compound is a heterocyclic compound having between 3 and 7 atoms, having between 4 and 7 atoms, having between 5 and 7 atoms, having between 3 and 6 atoms, having between 4 and 6 atoms, having 5 or 6 atoms, or having 6 or 7 atoms, within the ring portion of the compound. In certain aspects, the MND enzyme or fragment or variant thereof comprises: i) the amino acid sequence SEQ. ID NO: 2; ii) a fragment of the amino acid sequence SEQ. ID NO: 2, wherein the fragment comprises an N- and/or C-terminal truncation of SEQ ID NO: 2; or iii) a variant of SEQ. ID NO: 2, wherein the variant has at least 85%, 90%, 95%, 98%, or 99% identity with the amino acid sequence SEQ ID NO: 2. In certain aspects, the MND enzyme fragment is a fragment produced by partial Proteinase K digestion of a polypeptide comprising the amino acid sequence SEQ ID NO: 2. In certain aspects, the N-methylated compound is selected from the group consisting of thebaine, oripavine, (R)-reticuline, salutaridine, salutaridinol, heroin, morphinone, codeinone, codeine, morphine, hydromorphone, oxymorphone, galanthamine, laudanine (laudanidine), orientaline, protosinomenine, isoorientaline, laudanosine, (S)-reticuline, scopolamine, hyoscyamine (atropine), noscapine (narcotine), gramine, (−)-lobeline, physostigmine, isothebaine, (R,S)-autumnaline, and tropinone. In certain aspects, the N-methylated compound is thebaine. In certain aspects, thebaine is converted into the N-demethylated compound N-demethylthebaine (northebaine). In certain aspects, the conversion rate of the N-methylated compound into an N-demethylated compound is at least about 10%, 20%, 30% 40%, 50%, 60%, 70%, 80%, 90%, 95%, 98%, 99%, 99.9%, or 100%. In certain aspects, the conversion rate of thebaine into northebaine is at least about 90%, 95%, 98%, 99%, 99.9%, or 100%. In certain aspects, the N-methylated compound is incubated with the MND enzyme or fragment or variant thereof for at least about 20 minutes, 30 minutes, 1 hour, 2 hours, 4 hours, 6 hours, 8 hours, 12 hours, 18 hours, 24 hours, 48 hours, or 72 hours. In certain aspects, the MND enzyme or fragment or variant thereof is immobilized. In certain aspects, the N-methylated compound is incubated with the MND enzyme or fragment or variant thereof at a temperature of from any of about 4° C., 15° C., 20° C., 25° C., 30° C., 37° C., 42° C., 48° C., 55° C., 60° C., 65° C., or 72° C. to any of about 15° C., 20° C., 25° C., 30° C., 37° C., 42° C., 48° C., 55° C., 60° C., 65° C., 72° C., or 80° C. In certain aspects, the N-methylated compound is incubated with the MND enzyme or fragment or variant thereof at a temperature of about 4° C., 15° C., 25° C., 30° C., 37° C., 42° C., 48° C., 55° C., 60° C., 72° C., or 80° C. In certain aspects, the N-methylated compound is incubated with the MND enzyme or fragment or variant thereof in a buffered solution, wherein the buffered solution comprises a buffering capacity of from any of about pH 3.0, pH 4.0, pH 5.0, pH 6.0, pH 7.0, pH 8.0, or pH 9.0 to any of about pH 4.0, pH 5.0, pH 6.0, pH 7.0, pH 9.0, pH 10.0, or pH 10.5. In certain aspects, the N-methylated compound is incubated with the MND enzyme or fragment or variant thereof at a pH of about 4.0 in a citrate buffer. In certain aspects, the N-demethylated compound produced is further modified by the chemical or enzymatic addition of a functional moiety to the demethylated nitrogen. In certain aspects, the method is used in drug discovery.

Also provided for herein are methods of producing an active N-substituted compound or precursor thereof. In certain aspects, the method comprises using an N-demethylated compound produced by any of the methods disclosed herein as a precursor to produce the active N-substituted compound or precursor thereof. In certain aspects, the active compound or precursor thereof is produced by the chemical or enzymatic addition of a functional moiety to the demethylated nitrogen. In certain aspects, the method further comprises screening the activity of the active compound for drug discovery. In certain aspects, the active compound produced is a pharmaceutical compound. In certain aspects, the active compound produced is a synthetic or semisynthetic opiate. In certain aspects, the synthetic or semisynthetic opiate is selected from the group consisting of oxycodone, oxymorphine, nalbuphine, naltrexone, buprenorphine, naloxone, and nalmefene. In certain aspects, the active compound produced is selected from the group consisting of tropane alkaloids, benzylisoquinoline alkaloids, pyrroloindole alkaloids, piperidine alkaloids, aporphine alkaloids, and Amaryllidaceae alkaloids. In certain aspects, the active compound produced is selected from the group consisting of noratropine, oxitropium, and ipratropium bromide. In certain aspects, an N-methyl group of an N-methylated compound is substituted in the active compound with at least one alkyl group. In certain aspects, the demethylated nitrogen is substituted with: (i) a neutral N—R1 group, wherein R1 is selected from the group consisting of a methyl group, an allyle group, an isopropyl group, an ethyl group, a propene group, a cyclopropylmethyl group, and a cyclobutylmethyl group, or (ii) a cationic N⁺—R1 group, wherein R1 is selected from the group consisting of a methyl group and an isopropyl group, a methyl group and an ethyl group, a methyl group and a propene group, a methyl group and a cyclopropylmethyl group, and a methyl group and a cyclobutylmethyl group. In certain aspects, the demethylated nitrogen is substituted with N—R1 or N⁺—R1 having a structure selected from the group consisting of:

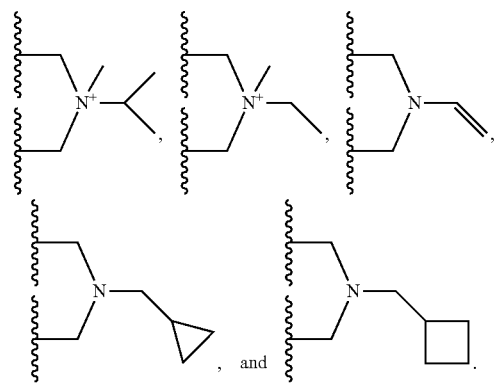

Also provided herein are non-naturally occurring nucleic acids comprising a nucleotide sequence that encodes: i) the amino acid sequence SEQ. ID NO: 2; ii) a fragment of the amino acid sequence SEQ. ID NO: 2, wherein the fragment comprises an N- and/or C-terminal truncation of SEQ ID NO: 2; or iii) a variant of SEQ ID NO: 2, wherein the variant has at least about 85%, 90%, 95%, 98%, or 99% identity with the amino acid sequence SEQ ID NO: 2. In certain aspects, the nucleotide sequence has at least about 75%, 80%, 85%, 90%, 95%, 98%, or 99% identity to SEQ ID NO: 1. In certain aspects, the nucleotide sequence comprises SEQ ID NO: 1. In certain aspects, the nucleotide sequence comprises one or more codons preferred for expression in a bacterial, yeast, insect, or plant cell. In certain aspects, the nucleotide sequence is codon optimized for expression in *Arabidopsis thaliana*. In certain aspects, the nucleotide sequence comprises SEQ ID NO: 3. In certain aspects, any of the nucleotide sequences disclosed herein is operably linked to at least one heterologous transcriptional regulatory sequence. In certain aspects, the heterologous transcriptional regulatory sequence is a promoter sequence. Certain aspects provide for a vector comprising a nucleic acid or recombinant nucleic acid construct disclosed anywhere herein. Certain aspects provide for a host cell comprising a nucleotide sequence discloses anywhere herein. In certain aspects a host cell comprises a recombinant nucleic acid construct or vector discloses anywhere herein. In certain aspects, the nucleotide sequence, the recombinant nucleic acid construct, or the vector is integrated into the genome of the host cell. In certain aspects, the host cell is a bacterial, yeast, insect, or plant cell. In certain aspects, the host cell is *E. coli* or *Agrobacterium*. In certain aspects, the host cell is a *Camelina sativa*, *Nicotiana benthamiana*, or *Papaver sominferum* cell.

Also provided herein are methods for producing a protein having N-demethylase activity. In certain aspects, a method comprises culturing a host cell disclosed anywhere herein, wherein the host cell comprises an expression vector, and wherein the method comprises recovering the thus-produced protein having N-demethylase activity.

Also provided for herein are isolated or purified non-naturally occurring proteins having N-demethylase activity, comprising: i) the amino acid sequence SEQ. ID NO: 2; ii) a fragment of the amino acid sequence SEQ. ID NO: 2, wherein the fragment comprises an N- and/or C-terminal truncation of SEQ ID NO: 2; or iii) a variant of SEQ. ID NO: 2, wherein the variant has at least 85%, 90%, 95%, 98%, or 99% identity with the amino acid sequence SEQ ID NO: 2. In certain aspects, the protein is a fragment produced by partial Proteinase K digestion of a polypeptide comprising the amino acid sequence SEQ ID NO: 2. In certain aspects, the protein further comprising a heterologous peptide sequence. In certain aspects, the heterologous peptide sequence is a sequence that targets the protein to a specific subcellular location or the heterologous peptide sequence is a histidine tag.

Also provided for herein are transgenic plants that comprise a nucleic acid, recombinant nucleic acid construct, or vector disclosed anywhere herein. In certain aspects, the nucleic acid, the recombinant nucleic acid construct, or the vector is integrated into the genome of the plant. In certain aspects, the plant is selected from the group consisting of *Camelina sativa*, *Nicotiana benthamiana*, and *Papaver somniferum*.

BRIEF DESCRIPTION OF THE DRAWINGS

FIG. 1A shows Thebainfresser morphology: images of Thebainfresser grown at 28° C. in MODLS+ thebaine media using the Nikon Eclipse 800 Microscope with 60× phase oil immersion objective.

FIG. 1B shows Thebainfresser morphology: images of Thebainfresser spread onto LB+Agar plate.

FIG. 2A shows un-inoculated thebaine crystals in MODLS+thebaine media: microscopic images using the Nikon Eclipse 800 Microscope with 60× phase oil immersion objective were taken of thebaine crystal in un-inoculated MODLS+thebaine media.

FIG. 2B shows Thebainfresser living on thebaine crystals in MODLS+thebaine media: microscopic images using the Nikon Eclipse 800 Microscope with 60× phase oil immersion objective were taken of thebaine crystal covered in Thebainfresser grown in MODLS+thebaine media.

FIG. 3 shows data from a Thebainfresser temperature optimum assay. A single colony of Thebainfresser was suspended in LB media and evenly distributed into 6 flasks, where two of each were grown at 21° C., 28° C., and 37° C. Growth of Thebainfresser was monitored by absorbance at OD600 for a period of 7 days.

FIG. 4 show data from a Thebainfresser N-demethylase induction assay. Analysis of N-demethylase induction was conducted by detection of northebaine production. Thebainfresser cultured in LB and Thebainfresser cultured in MODLS+thebaine were both washed and then resuspended in MODLS+thebaine and incubated at 28° C. for three days. The experiment was performed in duplicate. Samples were taken prior to induction and twice a day post induction and analyzed for northebaine by HPLC.

FIG. 5 shows data from an in vivo enzyme assay using candidate N-demethylase enzymes from Thebainfresser expressed in *E. coli* using thebaine as substrate. The *E. coli* expression strain BL21 Star (DE3) was individually transformed with the empty vector pET28a and four unknown enzymes (A-D). Each was cultured in Terrific Broth overnight prior to IPTG induction, toluene treatment, and addition of thebaine. Extracts were analyzed by QTRAP 6500. An overlay of MRM transitions specific to northebaine is shown (298.1/251).

FIG. 6 shows data from replicates of a toluene permeabilization assay using unknown enzyme D. *E. coli* transformed with pET28a empty vector and unknown enzyme D, the enzyme that exhibited prior N-demethylase activity, were cultured in Terrific Broth and induced with IPTG, in duplicate, and subject to toluene treatment and incubation with thebaine. Samples were extracted, analyzed, and quantitated by LC-MS/MS using the QTRAP 6500.

FIG. 7 shows SDS-PAGE of MND protein purification from expression in the *E. coli* strain 'BL21 star (DE3)'. Volumes used for cell suspensions were normalized based on OD600 then concentrated prior to running. Laemmli sample buffer supplemented with β-mercaptoethanol was added to each sample for a total volume of 20 µl prior to denaturation at 95° C. and analysis on 10% SDS-PAGE. Lane 1: 10 µl Low molecular weight ladder (BIO-RAD), Lane 2: 20 µl pET28a empty vector cell suspension (post IPTG induction), Lane 3: 17.6 µl MND cell suspension (pre IPTG induction), Lane 4: 12 µl MND cell suspension (post IPTG induction), Lane 5: 1 µl MND supernatant after cell lysis and centrifugation, Lane 6: 1 µl MND pellet after cell lysis and centrifugation, Lane 7: 2 µl MND supernatant from TALON resin, Lane 8: 2 µl 5 mM imidazole wash, Lane 9: 5 µl 100 mM imidazole wash, Lane 10: 10 µl eluted protein post PD-10 desalting column. The MND protein is indicated by an arrow.

FIG. 8 shows data from an enzyme assay with His-tag purified MND enzyme from BL21 Star (DE3) cells using thebaine as substrate. Enzyme assays contained 30 mM potassium phosphate buffer pH 8.0, 1500 pmol thebaine, and 100 µl enzyme or water in the case of the no enzyme control. The assay containing MND enzyme was performed in duplicate. An empty vector control, a no enzyme control, and a boiled MND enzyme control were also included. Enzyme assays were extracted with ethyl acetate prior to filtration, dilution and analysis by LC-MS/MS using the QTRAP 6500. The chromatograph shows the MRM transition 298.1/251.0, a transition specific to northebaine.

FIG. 9 shows the amount of northebaine produced from assays containing thebaine and purified MND enzyme, pET28a, boiled MND enzyme, or no enzyme. Enzymes were incubated overnight at 30° C. with 1500 pmol of thebaine in 30 mM potassium phosphate buffer (pH 8.0), extracted twice with ethyl acetate, and dried to completion with N2. Dried samples were reconstituted with 150 µl of 50% MeOH then diluted 100 fold prior to LC-MS/MS analysis using the QTRAP 6500.

FIG. 10 shows a purified MND enzyme assay with thebaine as substrate overlain with negative control and standard. Enzyme assays included 36 MND enzyme plus 1500 pmol thebaine in 30 mM potassium phosphate buffer pH 8.0 in a total volume of 200 µl and were allowed to incubate at 30° C. overnight. Assays were extracted twice with ethyl acetate and diluted 50 fold prior to filtration and analysis by LC-MS/MS with the QTRAP 6500. An empty vector control (pET28a) was also included. Both panels are from the same enzyme assay where the top is an overlay of MRM transition 312.1/251.0 (thebaine specific) and the bottom is an overlay of MRM transition 298.1/251.0 (northebaine specific). The chemical structures of each compound are included. The fragmentation pattern obtained from each compound is also included in their respective panel where the major fragments are indicated.

FIG. 11 shows the amount of northebaine produced by BL21 Star (DE3) and PLUSE cells transformed with pET28a and MND enzyme treated with toluene then incubated with thebaine overnight. PLUSE and BL21 star (DE3) cells transformed with an MND-encoding vector and pET28a were induced with IPTG then normalized using OD600 prior to toluene treatment and overnight incubation with 20 μM (200 nmol) thebaine. One half of each culture was extracted and concentrated to 200 μl prior to 100 fold dilution and analysis by LC-MS/MS using the QTRAP 6500. Each assay was performed in triplicate.

FIG. 12 shows SDS-PAGE of an MND-encoding vector and pET28a transformed into both BL21 Star (DE3) cells and PLUSE cells used for permeabilization assay. Samples were analyzed by 7% SDS-PAGE pre-induction and post-induction with IPTG. Laemmli sample buffer supplemented with β-mercaptoethanol was added to each sample for a total volume of 20 μl prior to denaturation at 95° C. Lane 1: 10 μl low molecular weight ladder (BIO-RAD), Lane 2: 5.7 μl pET28a empty vector in BL21 Star (DE3) cell suspension (pre IPTG induction), Lane 3: 9.4 μl pET28a empty vector in BL21 Star (DE3) cell suspension (post IPTG induction), Lane 4: 3.9 μl MND in BL21 Star (DE3) cell suspension (pre IPTG induction), Lane 5: 5.8 μl MND in BL21 Star (DE3) cell suspension (post IPTG induction), Lane 6: 5.5 μl pET28a empty vector in PLUSE cell suspension (pre IPTG induction), Lane 7: 9.1 μl pET28a empty vector in PLUSE cell suspension (post IPTG induction), Lane 8: 4.4 μl MND in PLUSE cell suspension (pre IPTG induction), Lane 9: 6.1 μl MND in PLUSE cell suspension (post IPTG induction). The GroEL and MND proteins are indicated by an asterisk and an arrow, respectively. Volumes used for cell suspensions were normalized based on OD600 and concentrated prior to running.

FIG. 13 shows SDS-PAGE of MND enzyme purification from expression in the E. coli strain 'PLUSE'. Samples taken throughout protein purification were analyzed by 10% SDS-PAGE. Volumes used for cell suspensions were normalized based on OD600 and concentrated prior to running. Lane 1: 10 μl low molecular weight ladder (BIO-RAD), Lane 2: 22 μl pET28a empty vector cell suspension (24 h post IPTG induction), Lane 3: 25 μl MND cell suspension (4 h post IPTG induction), Lane 4: 13.8 μl MND cell suspension (24 h post IPTG induction), Lane 5: 1 μl MND supernatant after cell lysis and centrifugation, Lane 6: 1 μl MND pellet after cell lysis and centrifugation, Lane 7: 2 μl MND supernatant from TALON resin, Lane 8: 2 μl 5 mM imidazole wash, Lane 9: 5 μl 100 mM imidazole wash, Lane 10: 10 μl eluted protein post PD-10 desalting column. The MND protein is indicated by an arrow. Volumes used for cell suspensions were normalized based on OD600 and concentrated prior to running. Laemmli sample buffer supplemented with β-mercaptoethanol was added to each sample for a total volume of 20 μl prior to denaturation at 95° C.

FIG. 14 shows data from an enzyme assay with His-tagged MND purified from PLUSE cells using thebaine as substrate. Enzyme assays were performed in duplicate prior to ethyl acetate extraction, filtration, dilution, and analysis by LC-MS/MS using the QTRAP 6500. Only one of the MND replicate assays is shown for clarity.

FIG. 15 shows the amount of northebaine produced from enzyme assays with purified MND enzyme using thebaine as substrate. The MND enzyme assay was performed in duplicate. All assays contained 100 μl of purified enzyme (or water), 30 mM potassium phosphate buffer (pH 8.0), and 1500 pmol thebaine and incubated overnight at 30° C. prior to ethyl acetate extraction, filtration, dilution, and analysis by LC-MS/MS with the QTRAP 6500. Quantitation of northebaine was normalized using codeine as an internal standard.

FIGS. 16A and 16B show representative compound structures used for MND enzyme substrate testing.

FIG. 17 shows data from a MND enzyme temperature optimum assay. MND enzyme activity for northebaine production was evaluated at various temperatures to identify the temperature optimum. Each assay was performed in duplicate and contained 30 mM potassium phosphate buffer pH 8.0, 100 μl purified enzyme, and 1500 pmol of thebaine. Assays were allowed to proceed for 20 min at 20° C., 25° C., 30° C., 40° C., 50° C., 60° C., 70° C., and 80° C. prior to protein precipitation, dilution, filtration and introduction to the QTRAP 6500 for LC-MS/MS analysis and quantitation. A pET28a empty vector control was included at each temperature.

FIG. 18 shows data from a MND enzyme pH optimum enzyme assay. MND enzyme activity for northebaine production included assays containing 100 μl (~36 μg) enzyme purified MND enzyme protein, 1500 pmol thebaine and 60 mM buffer (citrate buffer pH 4, and pH 5; potassium phosphate buffer pH 6, pH 7, pH 8; glycine-NaOH buffer and pH 9, pH 10, and pH 10.5). Samples were incubated at 30° C. for 20 min prior to protein precipitation, dilution, filtration, and introduction into the QTRAP 6500 for LC-MS/MS analysis and quantitation. MND enzyme samples were performed in duplicate. A pET28a empty vector control was included at each pH.

FIG. 19 shows data from a supplemental pH optimum assay with MND enzyme focusing on lower pHs. Each experimental reaction was completed in duplicate in 60 mM buffer with 1500 pmol thebaine and 100 μl (~36 μg) enzyme. Error bars show standard deviation. A control reaction was included at each pH using purified empty vector as enzyme. Assays were allowed to incubate for 20 min at 30° C. prior to addition of 2 volumes 100% MeOH and rapid mixing (30 s). Samples were centrifuged then diluted with 50% MeOH and filtered prior to analysis by QTRAP 6500. pH 4 was repeated with glycine-HCl and citrate buffer.

FIG. 20 shows protein quantification of MND enzyme from His-tag purification. The following samples were run on a 10% Mini-PROTEAN TGX precast gel: lane 1) Biorad low range molecular weight marker; lane 2) 3,000 ng BSA; lane 3) 2,000 ng BSA; lane 4) 1,500 ng BSA; lane 5) 1,000 ng BSA; lane 6) 800 ng BSA; lane 7) 5 μl MND enzyme sample A; lane 8) 5 μl MND enzyme sample B; lane 9) 5 μl MND enzyme sample C; lane 10) 5 μl pET28a empty vector control. Samples were analyzed using a GelDoc EZ Imager and quantitate using Image Lab version 5.2.1.

FIG. 21 shows determination of MND enzyme kinetic parameters. Kinetic parameters of MND enzyme were determined by enzyme assay using increasing substrate concentrations and quantitation of northebaine production by LC-MS/MS using the QTRAP 6500. The calculated kinetic values were obtained using Prism 7.

FIG. 22 shows an MND enzyme stability assay. MND enzyme (~36 μg) was incubated at 30° C. for the times indicated (in triplicate) in 30 mM potassium phosphate pH 7.0 when 1500 pmol of thebaine was added. The reaction was allowed to proceed for 20 min and stopped by addition of 400 µl 100% methanol and rapid mixing for 30 seconds. Samples were centrifuged and diluted to a total of 50 fold, filtered, and analyzed by LC-MS/MS using a QTRAP 6500.

FIG. 23 shows the effect of FAD addition and Proteinase K digestion on MND enzyme. Enzyme assays with MND enzyme were performed with and without a prior 1 hour Proteinase K digestion and in the presence and absence of 1500 pmol FAD. Assays contained 30 mM potassium phosphate buffer pH 7.0 and 1500 pmol thebaine and were allowed to proceed for 20 minutes. Assays were stopped by addition of MeOH and mixing. Samples were then centrifuged, diluted, filtered, and analyzed by LC-MS/MS with the QTRAP 6500.

FIG. 24 shows the effects of cofactors and validation of the effect of Proteinase K digestion on MND enzymatic activity. Enzyme assays were completed in duplicate. Assays contained 30 mM potassium phosphate buffer pH 7.0 and 1500 pmol thebaine. Reactions were terminated after 20 minutes by MeOH addition and mixing. Samples were centrifuged, diluted, filtered, and analyzed by LC-MS/MS using the QTRAP6500.

FIG. 25 is a Phylogenetic tree of MND enzyme and closely related protein sequences. Protein sequences for the tree were obtained from the NCBI NR database and Uniprot using the MND enzyme protein sequence and protein BLAST. Top hits were chosen in addition to hits further down the list having better annotation. Each branch is labeled using the database entry followed by the putative function and species for each sequence. Sequences were aligned using the MUSCLE algorithm and the maximum likelihood tree was constructed using MEGA 6.06 with 500 bootstraps. Placement of MND enzyme in the tree is indicated by a star. The closest hit from BLAST is indicated by an asterisk.

FIG. 26 shows that MND contains the cofactor flavin adenine dinucleotide. Samples of MND and empty vector control were either boiled or untreated prior to addition of menthol for protein precipitation. After centrifugation, supernatants were analyzed by LC-MS/MS. TIC of each sample, control, and the standards flavin adenine dinucleotide (FAD) and flavin mononucleotide (FMN) are shown.

FIG. 27 shows MND activity testing in industrial solvents. Enzyme assays with 5% and 25% of DMSO, methanol, chloroform, tetrahydrofuran, toluene, heptane, and diethyl ether were performed in duplicate and contained 30 mM potassium phosphate buffer pH 7.0, 36 µg purified enzyme, and 1500 pmol of thebaine. Assays were allowed to proceed for 20 min at 30° C. and analyzed by LC-MS/MS using the QTRAP 6500.

FIG. 28 shows MND expression testing in different *E. coli* strains. His-tagged MND and pET28a empty vector control were transformed into *E. coli* expression strains PlusSa, BL21 (DE3) pLysS, BL21 Star (DE3), and PlusE. Each strain was cultured, in duplicate, for 24 hours, and induced for 24 hours. Cell density was normalized then subjected to toluene permeabilization and incubation with 20 thebaine for about 24 hours. Cultures were extracted with ethyl acetate and northebaine production was quantitated by LC-MS/MS using QTRAP 6500.

FIG. 29 shows N-demethylation by MND attached to Sepharose beads. 1 mg of His-tagged purified MND was coupled to CNBr-activated Sepharose™ 4B (GE Healthcare). 1500 pmol of thebaine was added to a stopped up column containing 0.1 M potassium phosphate buffer pH 7.0 for 20 minutes. After sample collection by centrifugation, the column was washed with buffer and 200 µl of 0.1 M potassium phosphate buffer pH 7.0 was added in addition to another 1500 pmol of thebaine and incubated overnight. Controls included thebaine incubated with buffer, thebaine added to 200 µl of $NaHCO_3$ wash (after initial ligand binding) with and without residual beads, and to a mix of the acid/base wash as controls. Samples were precipitated with MeOH and analyzed by LC-MS/MS QTRAP 6500.

DETAILED DESCRIPTION

Figure 1A:
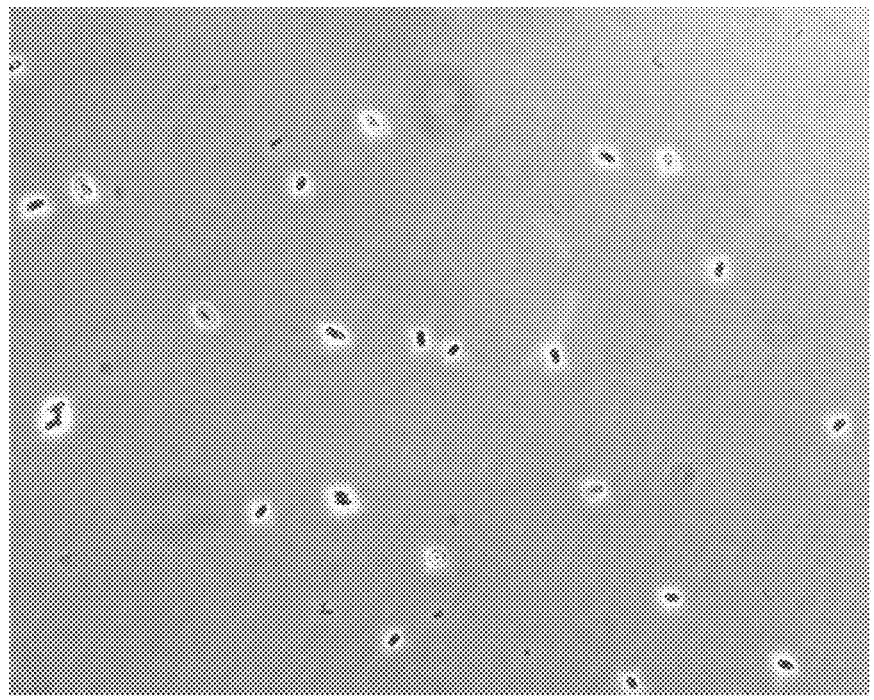
FIG. 1A.

An enzyme in a pink-pigmented facultative methylotroph has been discovered that N-demethylates thebaine to N-demethylthebaine (northebaine) with 100% conversion in an aqueous solution at 30° C. It has subsequently been demonstrated that this enzyme N-demethylates numerous compounds in addition to thebaine. The methods disclosed herein can thus eliminate the need for toxic chemicals and avoid the concomitant toxic waste of the industrial chemical N-demethylation process currently utilized in the production of synthetic opiates.

Definitions

To the extent necessary to provide descriptive support, the subject matter and/or text of the appended claims is incorporated herein by reference in their entirety.

It will be understood by all readers of this written description that the exemplary embodiments described and claimed herein may be suitably practiced in the absence of any recited feature, element or step that is, or is not, specifically disclosed herein.

It is to be noted that the term "a" or "an" entity refers to one or more of that entity; for example, "a compound," is understood to represent one or more compounds. As such, the terms "a" (or "an"), "one or more," and "at least one" can be used interchangeably herein.

Furthermore, "and/or" where used herein is to be taken as specific disclosure of each of the specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, technical and scientific terms used herein have the same meaning as commonly understood by one of ordinary skill in the art to which this disclosure is related. Numeric ranges are inclusive of the numbers defining the range. Even when not explicitly identified by "and any range in between," or the like, where a list of values is recited, e.g., 1, 2, 3, or 4, the disclosure specifically includes any range in between the values, e.g., 1 to 3, 1 to 4, 2 to 4, etc.

The headings provided herein are solely for ease of reference and are not limitations of the various aspects or aspects of the disclosure, which can be had by reference to the specification as a whole. Accordingly, the terms defined immediately below are more fully defined by reference to the specification in its entirety.

As used herein, the term "non-naturally occurring" condition, substance, polypeptide, polynucleotide, composition, entity, plant, organism, individual, and/or any combination thereof, or any grammatical variants thereof, is a conditional term that explicitly excludes, but only excludes, those forms that are well-understood by persons of ordinary skill in the art as being "naturally-occurring," or that are, or might be at any time, determined or interpreted by a judge or an administrative or judicial body to be, "naturally-occurring."

As used herein, the term "low molecular weight" in reference to an N-methylated compound means less than about 1,500 Daltons.

As used herein, the term "identity," e.g., "percent identity" to an amino acid sequence or to a nucleotide sequence disclosed herein refers to a relationship between two or more nucleotide sequences or between two or more amino acid sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. In order to optimally align sequences for comparison, the portion of a nucleotide or amino acid sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using, e.g., the program "BLAST" which is available from the National Center for Biotechnology Information, and which program incorporates the programs BLASTN (for nucleotide sequence comparison) and BLASTP (for amino acid sequence comparison), which programs are based on the algorithm of Karlin and Altschul (*Proc. Natl. Acad. Sci. USA* 90(12):5873-5877, 1993).

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-standard amino acids. A polypeptide can be derived from a natural biological source or produced by recombinant technology, but is not necessarily translated from a designated nucleic acid sequence. It can be generated in any manner, including by chemical synthesis.

A "protein" as used herein can refer to a single polypeptide, i.e., a single amino acid chain as defined above, but can also refer to two or more polypeptides that are associated, e.g., by disulfide bonds, hydrogen bonds, or hydrophobic interactions, to produce a multimeric protein.

By an "isolated" polypeptide or a fragment, variant, or derivative thereof or the like is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are recombinant polypeptides that have been separated, fractionated, or partially or substantially purified by any suitable technique. An isolated polypeptide or fragment, variant, or derivative thereof or the like can be associated, bound, etc., with a cofactor. Likewise, a purified or purified and isolated polypeptide or fragment, variant, or derivative thereof or the like can be associated, bound, etc., with a cofactor.

Other polypeptides disclosed herein are fragments, derivatives, analogs, or variants of the polypeptides disclosed herein, and any combination thereof. The terms "fragment," "variant," "derivative" and "analog" when referring to polypeptide subunit or multimeric protein as disclosed herein can include any polypeptide or protein that retain at least some of the activities of the complete polypeptide or protein (for example retain at least some of the enzymatic properties), but which is structurally different. Fragments of polypeptides include, for example, proteolytic fragments, as well as deletion fragments. Variants include fragments as described above, and also polypeptides with altered amino acid sequences due to amino acid substitutions, deletions, or insertions. Variants can occur spontaneously or be intentionally constructed. Intentionally constructed variants can be produced using art-known mutagenesis techniques. Variant polypeptides can comprise conservative or non-conservative amino acid substitutions, deletions or additions. Variant polypeptides can also be referred to herein as "polypeptide analogs." Derivatives are variants of polypeptides that have been altered so as to exhibit additional features not found on the native polypeptide. Examples include fusion proteins. As used herein a "derivative" also refers to a subject polypeptide having one or more amino acids chemically derivatized by reaction of a functional side group. Also included as "derivatives" are those peptides that contain one or more standard or synthetic amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

As used herein, a "single amino acid substitution" means replacing an amino acid residue in a polypeptide sequence with a different amino acid residue (such as replacing the native residue in a wild-type sequence with a non-native amino acid), unless otherwise specified. Also encompassed by the disclosure are a "single amino acid deletion" and/or a "single amino acid insertion."

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Methods of identifying nucleotide and amino acid conservative substitutions which do not eliminate protein activity are well-known in the art (see, e.g., Brummell et al., *Biochem.* 32: 1180-1 187 (1993); Kobayashi et al., *Protein Eng.* 12(10):879-884 (1999); and Burks et al., *Proc. Natl. Acad. Sci. USA* 94: 412-417 (1997)).

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a polypeptide subunit contained in a vector is considered isolated as disclosed herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "coding region" is a portion of nucleic acid comprising codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode a selection marker gene and a gene of interest. In addition, a vector, polynucleotide, or nucleic acid can encode heterologous coding regions, either fused or unfused to a nucleic acid encoding a polypeptide subunit or fusion protein as provided herein. Heterologous coding regions include without limitation specialized elements or motifs, such as a secretory signal peptide or a heterologous functional domain.

In certain aspects, the polynucleotide or nucleic acid is DNA. In the case of DNA, a polynucleotide comprising a nucleic acid that encodes a polypeptide normally can include a promoter and/or other transcription or translation regulatory elements operably associated with one or more coding regions. An operable association or linkage can be when a coding region for a gene product, e.g., a polypeptide, can be associated with one or more regulatory sequences in such a way as to place expression of the gene product under the influence or control of the regulatory sequence(s). Two DNA fragments (such as a polypeptide coding region and a promoter associated therewith) can be "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription regulatory elements, besides a promoter, for example enhancers, operators, repressors, and transcription termination signals, can be operably associated with the polynucleotide to direct cell-specific transcription.

A variety of transcription regulatory regions are known to those skilled in the art. These include, without limitation, transcription regulatory regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription regulatory regions include those derived from vertebrate genes such as actin, heat shock protein, bovine growth hormone and rabbit β-globin, as well as other sequences capable of controlling gene expression in eukaryotic cells. Additional suitable transcription regulatory regions include tissue-specific promoters and enhancers.

Similarly, a variety of translation regulatory elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other aspects, a polynucleotide can be RNA, for example, in the form of messenger RNA (mRNA).

Polynucleotide and nucleic acid coding regions can be associated with additional coding regions which encode secretory or signal peptides, which direct the secretion of a polypeptide encoded by a polynucleotide as disclosed herein. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain aspects, the native signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse ß-glucuronidase.

A "vector" is nucleic acid molecule as introduced into a host cell, thereby producing a transformed host cell. A vector can include nucleic acid sequences that permit it to replicate in a host cell, such as an origin of replication. A vector can also include one or more selectable marker gene and other genetic elements known in the art. Illustrative types of vectors include plasmids, phages, viruses and retroviruses.

A "transformed" cell, or a "host" cell, is a cell into which a nucleic acid molecule has been introduced by molecular biology techniques. As used herein, the term transformation encompasses those techniques by which a nucleic acid molecule can be introduced into such a cell, including transfection with viral vectors, transformation with plasmid vectors, and introduction of naked DNA by electroporation, lipofection, and particle gun acceleration. A transformed cell or a host cell can be a bacterial cell or a eukaryotic cell.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

The term "pharmaceutical composition" refers to a preparation that is in such form as to permit the biological activity of the active ingredient to be effective, and that contains no additional components that are unacceptably toxic to a subject to which the composition would be administered. Such composition can be sterile.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

N-Demethylation of an N-Methylated Compound Using MND Enzyme

Disclosed herein are methods for N-demethylating an N-methylated compound using an enzymatic reaction, rather than, e.g. a chemical modification. In certain aspects, the N-methylated compound is a low molecular weight N-methylated compound. The N-methylated compound to be demethylated, unless otherwise indicated herein, is interchangeably referred to as the "substrate". In certain aspects, the substrate has the structure of a naturally-occurring opiate compound.

Figure 16A:
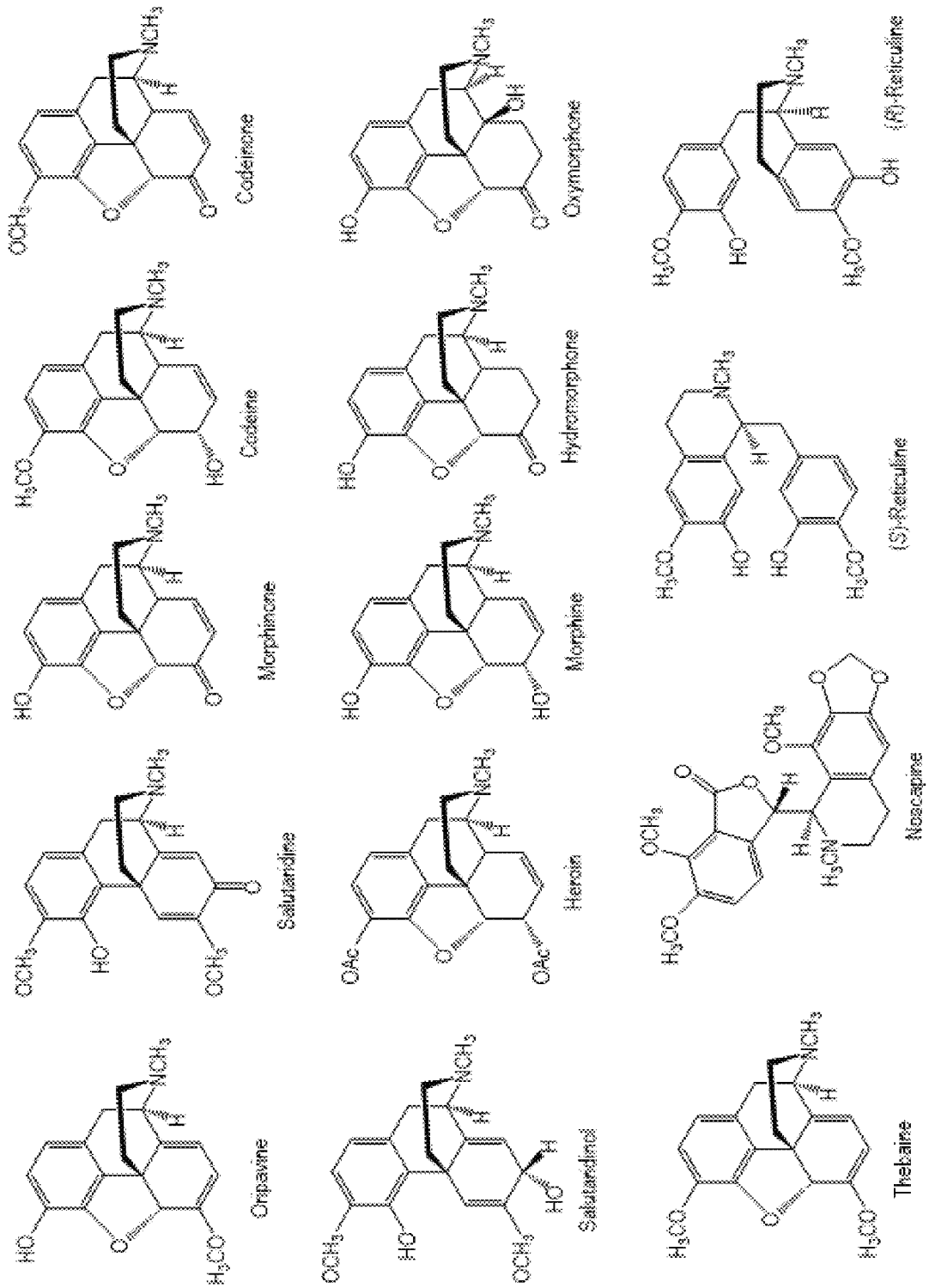
FIGS. 16A and 16B.
Figure 16B:
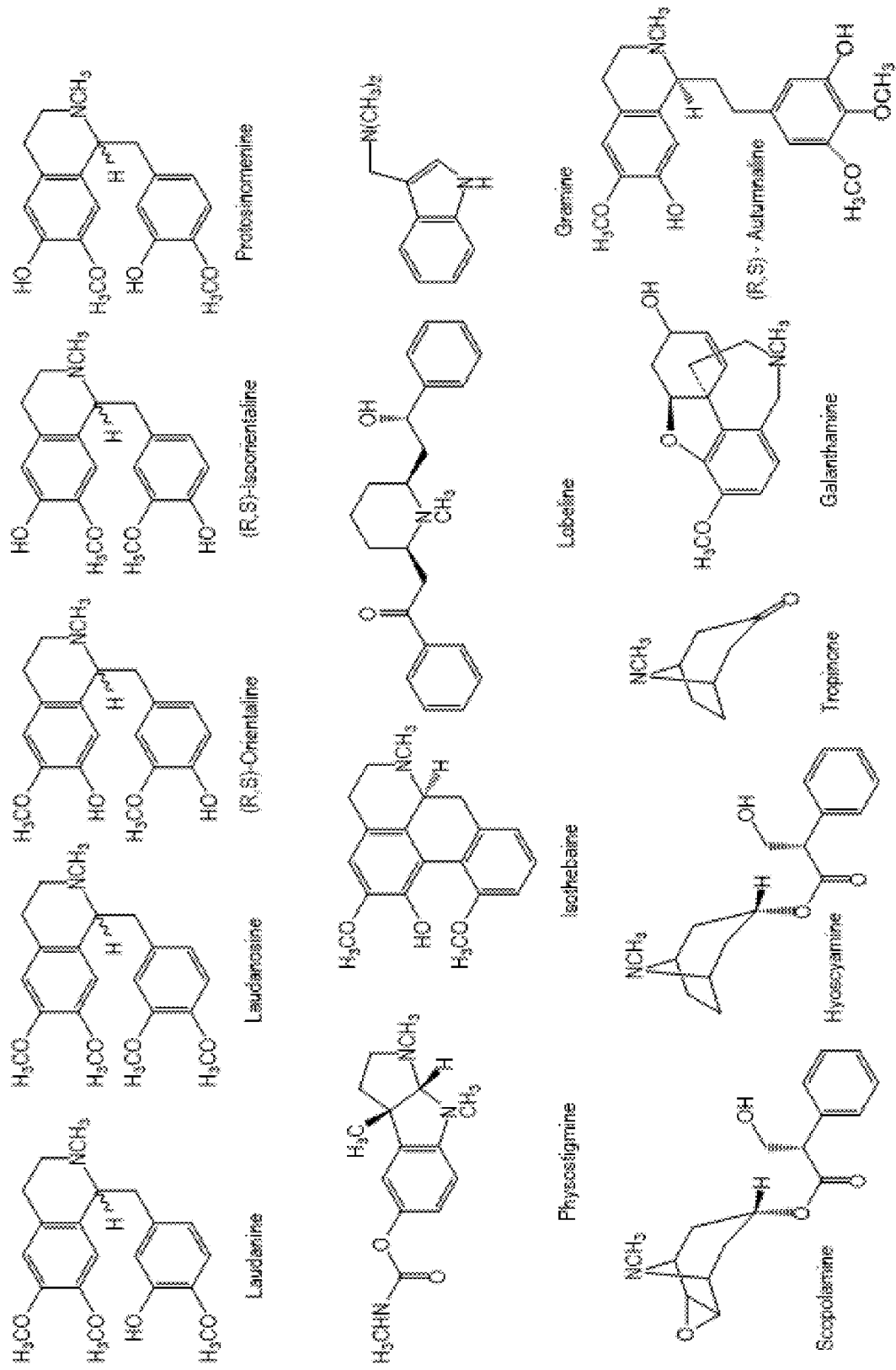

Exemplary low molecular weight N-methylated compounds include, but are not limited to, thebaine, oripavine, (R)-reticuline, salutaridine, salutaridinol, heroin, morphinone, codeinone, codeine, morphine, hydromorphone, oxymorphone, galanthamine, laudanine (laudanidine), orientaline, protosinomenine, isoorientaline, laudanosine, (S)-reticuline, scopolamine, hyoscyamine (atropine), noscapine (narcotine), tropinone, physostigmine, isothebaine, (−)-lobeline, gramine, and any of the compounds otherwise listed in FIG. 16. In certain aspects, the N-methylated compound is a heterocyclic compound. In certain aspects, a heterocyclic compound has 3, 4, 5, 6, or 7 atoms in the ring portion of the compound. Thus, in certain aspects, a heterocyclic compound has 3 or 4 atoms, between 3 and 5 atoms, between 3 and 6 atoms, between 3 and 7 atoms, 4 or 5 atoms, between 4 and 6 atoms, between 4 and 7 atoms, 5 or 6 atoms, between 5 and 7 atoms, or 6 or 7 atoms within the ring portion of the compound. In certain aspects, the N-methylated compound is a five-ringed morphinan alkaloid. In certain aspects, the N-methylated compound is thebaine which can be converted into the N-demethylated compound N-demethylthebaine (northebaine).

The methods disclosed herein of N-demethylating an N-methylated compound comprise incubating the N-methylated compound with an enzyme comprising N-demethylase activity. One of ordinary skill in the art will understand what it means to incubate a substrate with an enzyme, and exemplary parameters such as time, temperature, buffer conditions, and pH are discussed in more detail elsewhere herein. In certain aspects, the enzyme with N-demethylase activity is a morphinan N-demethylase (MND) identified from the *Methylobacterium* Thebainfresser, or a fragment or variant of this enzyme having N-demethylase activity (referred to collectively herein as the "MND enzyme"). In certain aspects where thebaine is the substrate, the MND enzyme has a $V_{max}$ of about 0.32 pmol s$^{-1}$, $K_m$ of about 0.97 µM, and/or a $K_{cat}$ of about $6.5 \times 10^{-4}$ s$^{-1}$. Although the MND enzyme was identified for its morphinan activity, it has been demonstrated that the MND enzyme exhibits N-demethylase activity on a wide range of substrates, and thus the designation of the MND enzyme as a "morphinan" N-demethylase is not limiting on the substrates of the methods disclosed herein.

Upon incubation of the N-methylated compound (substrate) with the MND enzyme, the substrate is N-demethylated to produce an N-demethylated compound. In certain aspects, the N-methylated compound contains one methylated nitrogen and thus the N-demethylated compound will no longer contain any methylated nitrogens. In certain aspects, the N-methylated compound contains two or more methylated nitrogens and the N-demethylated compound contains at least one nitrogen that has been demethylated by the MND enzyme—and thus available for the addition of a new moiety—even if not all the methylated nitrogens on the compound are demethylated. In certain aspects, the N-methylated compound contains two or more methylated nitrogens and all of the methylated nitrogens are demethylated by the MND enzyme. Unless otherwise specified, where the N-methylated compound contains two or more methylated nitrogens, the N-demethylated compound refers to a compound in which at least one of the methylated nitrogens is demethylated.

In certain aspects, the MND enzyme is isolated, purified, or isolated and purified. While the MND enzyme activity was identified in a naturally occurring bacterium, the MND enzyme can be recombinantly expressed in other organisms including bacteria, yeast, plants, fungi, insects, birds, mammals, and cells thereof, for example overexpressed in a host cell selected for protein expression, to produce more usable quantities of the MND enzyme. In certain aspects, the MND enzyme can then be isolated from the host cell. The MND enzyme can also be purified by any means of protein purification. In certain aspects, the isolation and/or purification need only result in a crude preparation. In certain aspects, the MND enzyme expressed may be utilized to convert its substrate without isolation and/or purification, such as via cell permeabilization.

The organism designated Thebainfresser is known to consume thebaine as its sole carbon source to produce northebaine. The term "fresser" is derived from the German infinitive "fressen" which means "to eat," which is used only in reference to animals. The MND enzyme isolated from the *Methylobacterium* Thebainfresser has the amino acid sequence:

```
                                                  (SEQ ID NO: 2)
MTEKTPKLGSEAANKLGLEADISRRDMVGGVLIGAGAALLASVAP

GAINRALAEGPSRLPPVRGSGTGWRGIEIADDWQGPGGIGDYSKS

NGNTGKVIRDAHAGIRNHEFEKRLATASDVNEKYDVIIVGAGISG

LHSAYDLLRQRPNIKILMLDNHAIFGGEAKQNKMEVDGQALYGGQ

GPTLYSFVGDDLPSWKGNPALASIMELKTYPKEFGLPTETTWSDK

KTDVKVPVDLWFSMASPSQTDIAYRWEGSGLVKNPLLNSFRDAPV

SQKSKDAIALMLAVDNGAKRPVEPVGDVSTWVDNMTYAEFLKKVY

GADDEAVQLVDQIDVVGTAGLGGDVFNASLAALGLNQYGGIELWN

GGLQGLSLPTGNGGVGRSILRKFMPGAIKGGTSLTDTLFGDVNWD

VLDHANNNVRIRLNSTVVGVQNNETPTGTKDATVFFLHDNRLYKA

KGKAVIMGTPQQVNRNVCLNLPNHLSEAMGDFHHAPILVVNVALR

NWKSMEKAGVSGLRWFGEYPGIGQIVRSMVIDGKEIMPCDPSKPA

VMTFYIPMNQATRGMPRGEQAMTARHMLFNLTFADIELLIRDQLT

RAFGSYGFDAKRDIAAIVANRWGHALVCAGPGFYTGLNGKPPVSK

VITAGWDRVAFGHSDLSGRQAWTVAVNYARTAVANVFPKI.
```

In certain aspects, the methods of this disclosure comprise incubating an N-methylated compound with an enzyme comprising N-demethylase activity. One of ordinary skill in the art would recognize that for the purposes of this disclosure, "incubating" refers to an intentional, human executed experimental, commercial, industrial, etc. step that excludes any activity of the enzyme against the substrate that may occur in nature without human intervention. In certain aspects, the MND enzyme comprises the amino acid sequence SEQ ID NO: 2.

The enzymatic activity of the MND enzyme may not require the full sequence of SEQ ID NO: 2 as the activity or a useful portion thereof could reside in a fragment of the amino acid sequence SEQ ID NO: 2. In certain aspects, the N-methylated compound is incubated with an enzyme comprising a fragment of the amino acid sequence SEQ ID NO: 2. In certain aspects, the fragment can result from an N-terminal truncation of SEQ ID NO: 2, a C-terminal truncation of SEQ ID NO: 2, or a truncation at both ends of SEQ ID NO: 2. In certain aspects, a fragment of SEQ ID NO: 2 can be formed by the internal deletion of one or more regions of SEQ ID NO: 2. In certain aspects, the remaining regions can be linked directly together or linked via a linker sequence. An enzyme comprising a fragment of SEQ ID NO: 2 can be produced by various methods including protease digestion of a peptide having the amino acid sequence of SEQ ID NO: 2 or the expression of a truncated version of SEQ ID NO: 2. In certain aspects, a fragment of the amino acid sequence of SEQ ID NO: 2 is produced by partial or full Proteinase K digestion of a polypeptide comprising the amino acid sequence SEQ ID NO: 2 or a fragment or variant thereof.

It is well known that the activity of an enzyme can tolerate some variation in the amino acid sequence of the MND enzyme. Further, in some cases, certain changes in the amino acid sequence of an enzyme can increase activity. In certain aspects of the methods herein, the N-methylated compound is incubated with an enzyme having N-methylase activity that has an amino acid sequence that is related to, but varies from, the MND enzyme, i.e., a "variant of MND enzyme." In certain aspects, the variant is a variant of SEQ ID NO: 2. It is understood that variants include variants of any fragment of MND enzyme and/or SEQ ID NO: 2 disclosed elsewhere herein. In certain aspects, a variant has at least about 85%, 90%, 95%, 98%, or 99% identity with the amino acid sequence SEQ ID NO: 2 or a fragment thereof. In certain aspects, a variant has the amino acid sequence SEQ ID NO: 2, or a fragment thereof, with any one of 1 to 100 amino acid substitutions. In certain aspects, one or more of the, or all of the, changes from the amino acid sequence of SEQ ID NO: 2 in the variant are conserved amino acid substitutions. In certain aspects, none of the amino acid substitutions are within the active site(s) of the MND enzyme. In certain aspects, at least one of the amino acid substitutions is within the active site of the MND enzyme. In certain aspects, the fragment or variant of SEQ ID NO: 2 possesses about the same N-demethylase activity against one or more N-methylated substrates in comparison to the MND enzyme comprising the amino acid sequence SEQ ID NO: 2. In certain aspects, the fragment or variant of SEQ ID NO: 2 possess increased N-demethylase activity against one or more N-methylated substrates in comparison to the MND enzyme comprising the amino acid sequence SEQ ID NO: 2.

The MND enzyme of this disclosure exhibits activity against a broad range of N-methylated substrates. In certain aspects, in addition to morphinan N-demethylase activity, the MND enzyme further comprises one or more of for example benzylisoquinoline alkaloid N-demethylase activity, tropane alkaloid N-demethylase activity, pyrroloindole alkaloid N-demethylase activity, piperidine alkaloid N-demethylase activity, aporphine alkaloid N-demethylase activity, indole alkaloid N-demethylase activity, or Amaryllidaceae alkaloid N-demethylase activity.

The conversion of the N-methylated compounds into N-demethylated compounds can be very efficient. In certain aspects, at least about 20%, 30%, 40%, 50%, 60%, 70%, 75%, 80%, 85%, 90%, 95%, 97%, 98%, 99%, 99.5%, 99.9%, or 100% of the substrate incubated with the MND enzyme is N-demethylated, i.e., converted into an N-demethylated compound. In certain aspects, the conversion rate of the substrate thebaine into northebaine is at least about 75%, 80%, 85%, 90%, 95%, 97%, 98%, 99%, 99.5%, 99.9%, or 100%.

The activity of the MND enzyme is very stable and under certain conditions the MND enzyme can remain active for a long time. In certain aspects, the substrate or a source of substrate is incubated with the MND enzyme for at least about 5 minutes, 10 minutes, 15 minutes, 20 minutes, 30 minutes, 45 minutes, 1 hour, 2 hours, 3 hours, 4 hours, 6 hours, 8 hours, 12 hours, 15 hours, 18 hours, 24 hours, 30 hours, 36 hours, 48 hours, 60 hours, or 72 hours. In certain aspects, the MND enzyme is immobilized such as by attachment to a surface, for example the surface of a bead or the surface of a slide or dish. In certain aspects, the bead is a SEPHAROSE bead. Immobilization of the MND enzyme can allow for incubation of the substrate with the MND enzyme and then facilitate separation of the converted N-demethylated compound from the MND enzyme. This can allow the MND enzyme to be re-used in additional incubations and can avoid the need to "kill" the MND enzyme, such as by heat or pH change after the conversion reaction is completed. In certain aspects, the N-methylated compound is passed over the immobilized MND enzyme, such as in a column, thus converting N-methylated substrate into N-demethylated product in a continuous manner.

The MND enzyme is active over a wide range of temperatures. In certain aspects, the N-methylated compound is incubated with the MND enzyme at a temperature of about 4° C., 15° C., 20° C., 25° C., 30° C., 37° C., 42° C., 48° C., 55° C., 60° C., 65° C., 72° C., or 80° C. Thus, in certain aspects, the N-methylated compound is incubated with the MND enzyme at a temperature of from any of about 4° C., 15° C., 20° C., 25° C., 30° C., 37° C., 42° C., 48° C., 55° C., 60° C., 65° C., or 72° C. to any of about 15° C., 20° C., 25° C., 30° C., 37° C., 42° C., 48° C., 55° C., 60° C., 65° C., 72° C., or 80° C. One of ordinary skill in the art will understand that the temperature of the conversion reaction can influence factors such as the rate of the conversion, the efficiency of the conversion, non-specific activity, the stability of the MND enzyme, or simply the convenience of whether the incubation mixture needs to be cooled, heated, or at room temperature, e.g., between about 20° C. and 25° C.

The MND enzyme is also active over a wide pH range. In certain aspects, the N-methylated compound is incubated with the MND enzyme at a pH of about pH 3.0, about pH 4.0, about pH 5.0, about pH 6.0, about pH 7.0, about pH 8.0, about pH 9.0, about pH 10.0, about pH 10.5, or any range in between. In certain aspects, the N-methylated compound is incubated with the MND enzyme in a buffered solution comprising a buffering capacity of from any of about pH 3.0, pH 4.0, pH 5.0, pH 6.0, pH 7.0, pH 8.0, or pH 9.0 to any of about pH 4.0, pH 5.0, pH 6.0, pH 7.0, pH 9.0, pH 10.0, or pH 10.5. In certain aspects, the N-methylated compound is incubated with the MND enzyme at a pH of about pH 4.0 in a citrate buffer. In certain aspects, the buffer is a phosphate buffer.

It has been determined that the MND enzyme contains the cofactor flavin adenine dinucleotide (FAD). Thus, in certain aspects, a cofactor, such as FAD, is added to the enzyme (or fragment, variant, and/or derivative thereof) prior to or during incubation with the N-methylated compound.

It has also been determined that the MND enzyme is active in the presence of a number of solvents, including commercially and/or industrially utilized solvents. One of ordinary skill in the art would recognize that while water is solvent, there are many commercial or industrial solvents used and thus in certain aspects, the solvent is a solvent other than water. As used herein, "in the presence of a solvent other than water" means that water may or may not also be present. In certain aspects, the MND enzyme performs the reaction in the presence of a nonpolar solvent (e.g., chloroform), an aprotic polar solvent (e.g., tetrahydrofuran), and/or a polar protic solvent (e.g, methanol). Thus, representative examples of solvents include, but are not limited to, dimethyl sulfoxide, methanol, chloroform, tetrahydrofuran, toluene, heptane, and diethyl ether. In certain aspects, the concentration of the solvent in the incubation mixture can be at least 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, 99%, or in any range in between.

N-demethylation of a compound according to the methods disclosed herein produces an N-demethylated compound that can be subjected to further chemical or enzymatic modification. In certain aspects, the N-demethylated compound is further modified by the addition of a functional moiety to the demethylated nitrogen as disclosed in greater detail elsewhere herein. In certain aspects, the modification of N-demethylated compounds produces compounds, including novel compounds that can be used for example in drug discovery, such as by screening the biological activity of the modified compounds.

Production of an Active N-Substituted Compound

Disclosed herein are methods of producing a biologically active compound (an "active N-substituted compound"), or a precursor to a biologically active compound, from an N-demethylated compound produced by any of the methods for N-demethylating an N-methylated compound disclosed elsewhere herein. In certain aspects, the N-methylated compound is a low molecular weight N-methylated compound. The active N-substituted compound or precursor can be produced by the chemical or enzymatic addition of a functional moiety at the position of the demethylated nitrogen. In certain aspects, an active compound produced is used in drug discovery such as to screen its biological activity and in certain aspects, the active compound produced is a pharmaceutical compound.

In certain aspects, the N-methyl group of the N-methylated compound (the MND enzyme substrate), having been removed by N-methylation by the MND enzyme, is substituted in the active N-substituted compound with at least on alkyl group. In certain aspects, the N-methylated nitrogen of the substrate is substituted, after N-demethylation, with a neutral N—R1 group. In certain aspects, R1 is selected from the group consisting of a methyl group, an isopropyl group, an ethyl group, a propene group, a cyclopropylmethyl group, and a cyclobutylmethyl group. In certain aspects, the N-methylated nitrogen of the substrate is substituted, after N-demethylation, with a cationic $N^+$—R1 group. In certain aspects, R1 is selected from the group consisting of a methyl group and an isopropyl group, a methyl group and an ethyl group, a methyl group and a propene group, a methyl group and a cyclopropylmethyl group, and a methyl group and a cyclobutylmethyl group. For example, in certain aspects, the N-methylated nitrogen of the substrate is substituted as:

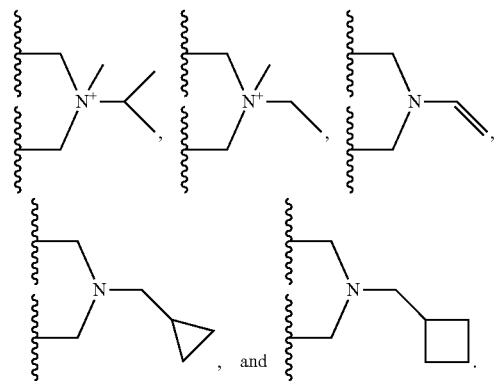

In certain aspects, the active N-substituted compound is an opiate. In certain aspects, the active N-substituted opiate is synthetic or semisynthetic. In certain aspects, a synthetic or semisynthetic opiate is selected from the group consisting of oxycodone, oxymorphine, nalbuphine, naltrexone, and nalmefene. In certain aspects, the active compound produced is selected from the group consisting of tropane alkaloids, benzylisoquinoline alkaloids, pyrroloindole alkaloids, piperidine alkaloids, aporphine alkaloids, indole alkaloids, and Amaryllidaceae alkaloids. In certain other aspects, the active compound produced is selected from the group consisting of noratropine, oxitropium, and ipratropium bromide.

For example, as described in Do Pham et al. *Studies on the oxidative N-demethylation of atropine, thebaine and oxycodone using a Fe III-TAML catalyst. Green Chem.*, 2014, 16, 1399-1409, N-demethylation of a precursor compound to form noratropine, followed by N-alkylation with isopropyl bromide and then with methyl bromide, produces the bronchodilator ipratropium bromide. By a similar process, the bronchodilator oxitropium bromide can be formed. As also described by Do Pham et al., thebaine serves as a synthetic precursor for the analgesic oxycodone and the intermediate oxymorphone. Oxymorphone is used to prepare the N-methylcyclobutyl-based analgesic nalbuphine, and the N-methylcyclopropyl-based opioid antagonists naltrexone and nalmefene, used in the treatment of alcohol or opiate dependence and for rapid opiate detoxification.

Nucleotides

Provide herein are nucleic acids comprising a nucleotide sequence that encodes the MND enzyme and/or the amino acid sequence SEQ. ID NO: 2 or a fragment or variant thereof. In certain aspects, the nucleotide sequence encodes a fragment of the amino acid sequence SEQ. ID NO: 2, wherein the fragment comprises an N- and/or C-terminal truncation of SEQ ID NO: 2; or a variant of SEQ ID NO: 2, wherein the variant has at least about 85%, 90%, 95%, 98%, or 99% identity with the amino acid sequence SEQ ID NO: 2. In certain aspects, the nucleotide sequence has at least about 50%, 60%, 70%, 75%, 80%, 85%, 90%, 95%, 98%, or 99% identity to SEQ ID NO: 1. In certain aspects, the nucleotide sequence comprises SEQ ID NO: 1.

```
                                                (SEQ ID NO: 1)
ATGACTGAAAAAACGCCTAAACTAGGCTCTGAAGCCGCAAATAAA

CTCGGATTAGAAGCTGACATTTCTCGGCGCGACATGGTGGGCGGC

GTATTGATCGGAGCAGGGGCAGCTCTGCTCGCATCCGTTGCGCCA

GGGGCGATTAATAGAGCGTTGGCCGAGGGGCCGAGCAGGCTACCG

CCGGTGCGTGGTTCCGGTACCGGTTGGCGAGGAATAGAGATCGCC

GATGACTGGCAAGGCCCAGGCGGCATCGGGGATTACTCTAAGTCA

AACGGCAACACGGGCAAAGTTATCCGTGACGCGCATGCAGGCATT

CGGAACCACGAGTTCGAGAAGCGGCTTGCTACGGCGAGTGACGTC

AACGAGAAATATGATGTTATTATTGTAGGCGCGGGCATTTCGGGG

CTTCACAGCGCCTACGATCTTCTTCGCCAGCGGCCAAATATAAAG

ATCCTAATGCTTGACAACCATGCCATCTTCGGTGGGGAGGCAAAG

CAAAATAAGATGGAGGTAGACGGTCAGGCGCTGTATGGCGGCCAG

GGCCCAACGCTTTACTCCTTCGTTGGTGATGACCTCCCGAGCTGG

AAAGGTAATCCGGCCCTCGCATCTATCATGGAACTCAAAACATAT

CCCAAGGAGTTCGGACTTCCGACCGAAACTACATGGAGCGATAAG

AAGACGGACGTAAAGGTGCCGGTCGACCTTTGGTTCTCCATGGCC

AGCCCCTCGCAGACCGACATCGCCTATCGGTGGGAGGGAAGTGGG

TTGGTGAAGAATCCTTTGCTGAACTCCTTTCGTGATGCCCCAGTG

TCGCAGAAAAGCAAAGATGCCATTGCCCTTATGCTCGCTGTCGAC

AACGGCGCGAAGAGGCCTGTTGAACCAGTGGGCGATGTATCGACC

TGGGTCGACAATATGACCTATGCGGAGTTTCTGAAGAAGGTATAT

GGTGCGGACGACGAAGCTGTTCAGCTTGTCGACCAGATTGATGTC

GTTGGAACAGCGGGGCTTGGCGGTGATGTTTTTAATGCAAGCCTT

GCAGCACTCGGACTAAATCAATACGGGGGCATCGAGCTCTGGAAC

GGCGGTTTGCAAGGGTTGAGTCTTCCGACCGGAAATGGCGGCGTG

GGGCGGTCCATCCTTCGCAAGTTCATGCCAGGAGCTATCAAGGGC

GGGACATCGCTCACCGACACGCTTTTCGGTGACGTGAACTGGGAC

GTGCTTGACCACGCTAACAACAACGTTCGAATCCGGCTCAATTCA

ACTGTCGTAGGTGTTCAGAATAATGAGACGCCGACTGGCACAAAA

GATGCGACCGTTTTCTTCCTTCACGATAATCGCCTTTACAAGGCC

AAAGGGAAGGCGGTGATCATGGGTACACCGCAGCAGGTCAATCGT

AATGTTTGCCTCAATTTGCCAAACCATCTTAGCGAGGCAATGGGC

GATTTCCATCATGCTCCGATCCTGGTTGTGAATGTGGCCCTCCGG

AACTGGAAATCGATGGAAAAGGCTGGCGTTTCCGGCTTGCGGTGG

TTCGGAGAATATCCGGGTATCGGTCAGATAGTTCGATCGATGGTC

ATTGACGGCAAAGAGATCATGCCTTGCGATCCCTCGAAACCAGCG

GTCATGACCTTCTATATCCCGATGAATCAAGCGACACGGGGCATG

CCTCGCGGCGAGCAAGCGATGACCGCCCGCCACATGCTTTTCAAC

TTGACGTTCGCAGATATCGAACTGCTCATTCGGGATCAGCTCACT

CGTGCGTTCGGATCTTATGGATTTGATGCCAAGCGGGACATCGCT

GCCATTGTTGCAAACAGGTGGGGACATGCGCTGGTCTGCGCCGGG

CCAGGATTTTACACTGGGCTTAACGGCAAACCGCCCGTCAGTAAG

GTGATCACCGCTGGATGGGACCGAGTGGCATTCGGGCATTCGGAC

CTTTCCGGCAGACAAGCATGGACCGTGGCCGTAAATTATGCACGG

ACAGCGGTTGCGAATGTCTTCCCTAAAATCTGA.
```

Because of redundancy in the genetic code, the nucleotide codons encoding specific amino acid residues can differ between organisms and there can be bias towards using one of the several codons that encode the same amino acid over the others. Thus, in certain aspects, a nucleic acid sequence comprises one or more codons preferred for expression in a bacterial, yeast, insect, or plant cell. In certain aspects, the nucleotide sequence is codon optimized for expression in *Arabidopsis thaliana*. In certain aspects, the nucleotide sequence comprises SEQ ID NO: 3.

```
                                                (SEQ ID NO: 3)
ATGACTGAGAAGACACCTAAACTTGGATCTGAGGCAGCTAATAAG

TTGGGTTTGGAGGCTGACATCTCTAGGAGAGATATGGTGGGAGGA

GTGCTTATCGGTGCAGGTGCTGCTTTGCTTGCATCTGTTGCTCCT

GGTGCTATCAACAGGGCTCTTGCAGAAGGACCATCAAGGCTTCCT

CCAGTTAGAGGTTCAGGAACTGGATGGAGGGGTATTGAGATTGCA

GACGACTGGCAAGGACCTGGAGGAATCGGAGATTATTCTAAGTCT

AACGGTAACACTGGAAAGGTGATCAGGGACGCTCACGCTGGTATC

AGGAACCATGAGTTCGAAAAGAGGTTGGCTACTGCTTCTGACGTG

AACGAGAAGTACGACGTGATCATCGTGGGAGCTGGTATCTCTGGA
```

-continued

```
CTTCACTCTGCATACGATTTGTTGAGACAAAGACCTAATATTAAA

ATTTTAATGTTGGACAACCACGCTATCTTCGGTGGTGAGGCTAAG

CAGAACAAGATGGAGGTTGACGGTCAGGCATTGTACGGAGGACAG

GGACCAACTCTTTACTCATTCGTTGGAGACGATTTGCCTTCATGG

AAGGGAAACCCTGCTTTGGCATCTATCATGGAACTTAAGACATAT

CCAAAGGAGTTCGGACTTCCAACTGAGACTACTTGGTCAGATAAG

AAGACTGACGTTAAGGTTCCAGTGGACCTTTGGTTCTCAATGGCA

TCACCTTCACAGACAGATATTGCTTACAGGTGGGAGGGTTCTGGT

TTGGTGAAAATCCTTTGCTTAACTCTTTCAGGGATGCTCCAGTT

TCTCAGAAGTCAAAGGATGCTATCGCTTTGATGCTTGCAGTGGAC

AACGGTGCTAAGAGACCTGTGGAACCTGTTGGAGACGTGTCTACA

TGGGTGGACAACATGACATACGCTGAGTTTTTGAAGAAGGTGTAC

GGAGCAGATGATGAGGCAGTTCAGTTGGTGGACCAGATCGACGTT

GTGGGTACAGCTGGACTTGGTGGAGACGTGTTCAACGCATCACTT

GCTGCTTTGGGTTTGAACCAGTACGGTGGAATCGAGTTGTGGAAC

GGAGGATTGCAGGGTCTTTCTTTGCCAACAGGTAATGGAGGAGTG

GGTAGGTCTATCCTTAGGAAGTTCATGCCTGGTGCTATTAAGGGT

GGAACATCTTTGACAGATACTCTTTTCGGTGACGTGAACTGGGAC

GTTTTGGATCACGCAAACAACAATGTGAGAATTAGACTTAATTCT

ACAGTGGTTGGAGTGCAGAACAACGAGACTCCTACAGGAACAAAA

GACGCTACTGTGTTTTTTTGCATGACAATAGACTTTATAAGGCT

AAGGGAAAAGCTGTGATCATGGGAACACCTCAGCAGGTGAATAGA

AACGTTTGTCTTAACCTTCCAAACCATCTTTCTGAGGCTATGGGT

GACTTCCATCACGCTCCAATCTTGGTGGTGAACGTGGCTCTTAGG

AACTGGAAATCTATGGAAAAGGCAGGAGTGTCAGGACTTAGGTGG

TTTGGAGAGTACCCTGGTATCGGACAGATCGTTAGGTCTATGGTG

ATTGATGGAAAGGAGATTATGCCATGCGACCCTTCTAAGCCAGCT

GTTATGACATTTTACATTCCTATGAATCAAGCTACTAGGGGAATG

CCAAGAGGAGAGCAGGCTATGACTGCTAGGCACATGCTTTTCAAT

CTTACTTTCGCTGATATTGAGTTGCTTATCAGGGACCAGTTGACT

AGGGCTTTCGGTTCTTACGGTTTCGACGCTAAGAGGGACATTGCT

GCTATCGTGGCTAACAGATGGGTCATGCTTTGGTTTGCGCTGGT

CCTGGATTCTACACTGGACTTAACGGAAAGCCTCCAGTGTCAAAG

GTGATCACAGCTGGATGGGACAGAGTGGCTTTTGGACATTCAGAC

TTGTCAGGAAGGCAGGCTTGGACAGTTGCTGTGAACTACGCTAGG

ACAGCAGTGGCTAACGTTTTCCCTAAGATATGA
```

Certain aspects provide for a recombinant nucleic acid construct that comprises a nucleic acid sequence encoding the MND enzyme or a fragment or variant thereof as disclosed herein. In certain aspects, the nucleic acid sequence encoding the MND enzyme or a fragment or variant thereof is operably linked to at least one transcriptional regulatory sequence. For example, in certain aspects, the sequence is operably linked to transcription regulatory sequences such as promoters, transcription terminators, enhancers, etc. The operable link can be direct or indirect, i.e. with or without intervening sequences, such as internal ribosome entry sites (IRES). The regulatory sequences can be endogenous to the coding sequence, i.e. they are the regulatory sequences naturally associated with the MND enzyme-encoding sequence in the genome of *Methylobacterium Thebainfresser*. Alternatively, the regulatory sequences can be heterologous. In this latter case the resulting construct comprises a coding sequence derived from *Methylobacterium Thebainfresser* operably linked to at least one heterologous transcription regulatory sequence. In certain aspects, the heterologous transcription regulatory sequence is a promoter sequence. Promoter sequences can include constitutive promoters, tissue specific promoters, developmentally specific promoters, and/or inducible promoters, depending upon what type of expression is sought. Examples of such promoters include but are not limited to the tissue specific promoters glycinin promoter, napin promoter, and oleosin promoter, the constitutive promoters 35 S promoter and cauliflower mosaic virus promoter and inducible promoters such as T7 promoter and AOX1 promoter. In certain aspects, the heterologous transcription regulatory sequence is a terminator sequence or other 3' regulatory regions. Several such terminators are available and known in the art (e. g. tm1 from CaMV, E9 from rbcS). Examples of such terminators include but are not limited to prokaryotic terminators t7 and rrnB, and engineered terminators such as TO.

Certain aspects provide for a vector comprising a recombinant nucleic acid construct described herein. A vector can be used to transfer a nucleic acid sequence (e.g., a shuttle vector) or to express the gene product of a nucleic acid sequence (e.g., expression vector). The nucleic acid molecules of the disclosure can be used to transform or transfect eukaryotic and prokaryotic cells. Thus, in certain aspects, the vector is inserted into a host cell so that the host cell comprises the vector. In certain aspects, the host cell is a bacterial, yeast, insect, avian, plant, or mammalian cell. In certain aspects, the host cell is a bacterial cell such as *E. coli* or *Agrobacterium*. In certain aspects, the host cell is a plant cell such as from *Camelina sativa, Nicotiana benthamiana*, or *Papaver sominferum*. In certain aspects, a nucleic acid of the disclosure (e.g., a nucleic acid that encodes the MND enzyme or a fragment or variant thereof, a construct, a vector, etc.) is used to create a transgenic plant. Thus, in certain aspects, a transgenic plant comprises a nucleic acid that encodes the MND enzyme or a fragment or variant thereof or a recombinant construct comprising such nucleic acid. In certain aspects, the plant is *Camelina sativa, Nicotiana benthamiana*, or *Papaver sominferum*. In certain aspects, the nucleic acid is integrated into the genome of a host cell or transgenic organism such as a transgenic plant.

Host cells comprising a nucleic acid sequence encoding the MND enzyme and/or a construct and/or vector disclosed herein can be used to produce a protein having an N-demethylase activity as described herein. Such host cells are provided by this disclosure. Thus, certain aspects provide for a method of producing a protein having N-demethylase activity. Such method comprises culturing a host cell comprising an expression vector under conditions conventional in the art for protein expression and recovering the MND enzyme having N-demethylase activity produced by the host cell. Certain aspects provide for producing an MND enzyme under conditions conventional in the art for protein expression and recovering the MND enzyme having N-demethylase activity produced by the host cell.

Morphinan N-Demethylase (the MND Enzyme)

This disclosure also provides for a protein having N-demethylase enzymatic activity referred to herein as the morphinan N-demethylase (MND) enzyme, although its N-demethylase activity is not limited to morphinan. In certain aspects, the protein is isolated, purified, or isolated and purified. In certain aspects, the protein is non-naturally occurring. In certain aspects, the protein comprises the amino acid sequence SEQ ID NO: 2. As discussed elsewhere herein, the protein can comprise a fragment or variant of SEQ ID NO: 2 having N-demethylase activity. Thus, in certain aspects, the protein comprises a fragment of the amino acid sequence SEQ. ID NO: 2, wherein the fragment comprises an N- and/or C-terminal truncation of SEQ ID NO: 2; a variant of SEQ. ID NO: 2, wherein the variant has at least 85%, 90%, 95%, 98%, or 99% identity with the amino acid sequence SEQ ID NO: 2; or any other fragment or variant disclosed anywhere herein. In certain aspects, the protein is a fragment produced by full or partial Proteinase K digestion. In certain aspects, the protein comprises an internal deletion within the MND enzyme and/or SEQ ID NO: 2 sequence. In certain aspects, the remaining sequence is directly linked or linked by one or more linker sequences.

In certain aspects, the amino acid sequence of a protein having N-demethylase activity comprises a heterologous peptide sequence such as a signal peptide that can target the protein to a specific subcellular location or a peptide that can aid in the isolation and/or purification of the peptide, such as a histidine tag.

The following examples are included to demonstrate certain embodiments of the disclosure. It should be appreciated by those of skill in the art that the techniques disclosed in the examples which follow represent techniques discovered by the inventor to function well in the practice of the disclosure. However, those of skill in the art should, in light of the present disclosure, appreciate that many changes can be made in the specific embodiments which are disclosed and still obtain a like or similar result without departing from the spirit and scope of the disclosure.

EXAMPLES

Materials and Methods
1.0. Culture Medium and Conditions.

Thebainfresser was routinely cultivated by addition of 10 ml of frozen stock in 90% culture medium/10% DMSO into 75 ml of MODLS+thebaine media. Cultures were maintained by diluting ½ with fresh media (usually 35 ml culture+25 ml of fresh media). Cells were grown at 21° C. or 28° C. at 140 rpm. Cultures were streaked or serially diluted on Potato Dextrose Agar media, MODLS+thebaine, MODLS+thebaine+vitamins media, and LB media to obtain single colonies of different organisms. Once single colonies of each organism were obtained and cultured, enzyme activity was monitored using N-demethylation of thebaine by TLC and later confirmed by LC-MS/MS using the QTRAP 4000.

2.0. Temperature Optimum for Thebainfresser Bacterial Growth.

A single colony of Thebainfresser was resuspended in 7 ml of LB media and 1 ml was aliquoted to each of 6 flasks containing 25 ml LB media. 500 µl were removed from each flask to serve as time point 1. Thebainfresser was cultivated at three temperatures; 21° C., 28° C., and 37° C., 200 rpm, two flasks in each. The OD600 was measured every day for 7 days.

3.0. Detection of Thebaine Conversion to Northebaine by TLC.

A solvent system consisting of toluene, acetone, ethanol, and ammonia (45:45:14:6) and TLC silica gel 60 F254 or Polygram SIL G/UV254 0.2 mm silica gel with florescent UV254 indicator was used for separation of thebaine and northebaine. 5 nmol of standard and 10-20 µl of culture were loaded onto the plate prior to placing in the solvent.

4.0. Detection of Thebaine Conversion to Northebaine by LC-MS/MS.

4.1 Qtrap 4000 Conditions.

Samples were extracted with chloroform under basic conditions or ethyl acetate and analyzed on a QTRAP 4000 by 10 µl injections using a flow rate of 0.5 ml/min. Source parameters included detection in the positive mode, CUR 30, CAD High, IS 5500, TEM 500, GS1 50 and GS2 55. Compounds were separated using a Gemini C-18 column (150×2.00 mm, 5 micron 110 Å; Phenomenex) and the following gradient using solvents A (5% acetonitrile/5% MeOH/10 mM ammonium acetate/15 mM $NH_4OH$) and B (90% acetonitrile/10 mM ammonium acetate/15 mM $NH_4OH$): 0-2.0 min 0% B, 2.0-9.0 min 0-44% B, 9.0-11.0 min 44-100% solvent B, 11-13 min 100% B and 100-0% solvent B from 13-14 min and held at 0% B for an additional 4 min. MRM (multiple reaction monitoring) scans detecting ion fragments 312.1/251 and 312.1/221 for thebaine and 298.1/251.0 and 298.1/236.0 for northebaine and EPI (enhanced product ion) scans for masses 312 m/z for thebaine and 298 m/z for northebaine were used with a DP (declustering potential) of 40 and a CE (collision energy) of 35. Data were analyzed using Analyst 1.5.

4.2 QTRAP 6500.
4.2.1 Method 1.

Samples were injected with an Eksigent ekspert microLC 200 system using a 15 µl/min flow rate and separated using a PLRP-S column (100×0.5 mm, 3µ, 100 Å, Higgins Analytical) prior to introduction to the QTRAP 6500 using the following solvents and binary gradient: solvent A (0.05% formic acid/0.01% NH4OH in H2O), solvent B (0.05% formic acid/0.01% NH4OH in 90% acetonitrile), and 0-2.0 min 5% B, 2.0-7.0 min 0-45% B, 7.0-7.5 min 45-100% solvent B, 7.5-9.0 min 100% B and 100-5% solvent B from 9.0-9.5 min and held at 5% B for an additional 5.5 min. Detection proceeded in the positive mode with source parameters including CUR 20, CAD-3, IS 5500, TEM 200, GS1 20, and GS2 20. Compounds were detected by MRM using CE 35, DP 85, Dwell 75 msec, and CXP 14 and detecting ion fragments 312.1/251 and 312.1/221 for thebaine and 298.1/251.0 and 298.1/236.0 for northebaine. EPI scans for masses 312 m/z for thebaine and 298 m/z for northebaine were used to qualitatively identify peaks initially, but not included for quantitation. Data were analyzed using Analyst 1.6.2. Quantitation was achieved by standard curve using peak area.

4.2.2 Method 2.

Samples were injected by the UFLCXR (Shimadzu) autosampler/pump system using a 0.5 ml/min flow rate prior to separation using a Gemini C-18 column (150×2.00 mm, 5µ, 110 Å; Phenomenex) and introduction into the QTRAP 6500. The program consisted of a binary gradient with solvent A (5% acetonitrile/5% MeOH/10 mM ammonium acetate/15 mM NH4OH) and solvent B (90% acetonitrile/10 mM ammonium acetate/15 mM NH4OH) and the following gradient: 0-2.0 min 0% B, 2.0-9.0 min 0-44% B, 9.0-11.0 min 44-100% solvent B, 11-13 min 100% B and 100-0% solvent B from 13-14 min and held at 0% B for an additional 8 min. EPI scans for each substrate and predicted product mass were included for each enzyme assay and source parameters were identical to those used for the QTRAP 4000 above except CE and DP which were based upon the optimum for each individual compound. Masses used can be found in table 3. Data were analyzed using Analyst 1.6.2.

4.2.3 Method 3.

Parameters were the same as method 2 except for the column, solvent A, and the gradient. Samples were separated using a Luna C-8 (2) 5μ 240×4.61 mm (Phenomenex). Solvent A was 10 mM ammonium acetate/15 mM NH4OH in H2O, and the following gradient was used: 0-4.0 min 1.5% B, 4.0-9.0 min 1.5-44% B, 9.0-11.0 min 44-100% solvent B, 11-13 min 100% B and 100-1.5% solvent B from 13-14 min and held at 0% B for an additional 8 min. Masses for EPI scans can be found in table 3.

4.2.4 Method 4.

Source parameters, hardware, and column were identical to Method 2. The program consisted of a 10 ul injection volume with a binary gradient including solvent A (0.1% formic acid in water) and solvent B (0.1% formic acid in acetonitrile) with the following gradient: 0-2.0 min 5% B, 2.0-32.0 min 5-95% B, 32.0-35.0 min 95% solvent B, 35.0-36.0 min 95%-5% B, and held at 5% B for an additional 9 min. The method included EPI scans for 786 m/z (FAD) and 457 m/z (FMN) with a DP of 85 and a CE of 25, and an EMS scan (200-1000 m/z).

5.0 Microscopy Images.

Microscopy images were obtained using the Nikon Eclipse 800 Microscope with a 60× phase oil immersion objective, 1.4 NA-pixel size 170 nm (used in FIJI/Image J to measure sizes or make scale bar).

6.0 Induction Experiment.

Thebainfresser was grown both in MODLS+thebaine (2×70 ml cultures) for several weeks and started fresh from single colonies in LB media (2×70 ml cultures). The cultures grown in MODLS+thebaine were sub-cultured (20 ml of culture into 50 ml fresh MODLS+thebaine) 7 days prior to cell collection and washing. Cultures growing in LB media were inoculated 11 days prior to cell collection and washing. 50 ml of each culture were collected by centrifugation (3,000×g, 20 min, RT) and washed three times with 10 ml of MODLS (no thebaine added). The final pellets were resuspended in 20 ml of MODLS+thebaine. 1 ml of each resuspended culture was used to measure the OD600. The OD600 was used to normalize the density of each culture in a final volume of 50 ml MODLS+thebaine. Cultures were incubated at 28° C., 200 rpm, and allowed to grow for 3 days. A 0.5 ml sample was taken prior to cell washing and twice each day post induction.

Samples were diluted 1:1 with 100% methanol followed by rapid mixing and centrifugation (16,000×g, 10 min, RT) prior to HPLC analysis using a Waters 1525 binary HPLC pump coupled with a Waters 2998 photo diode array detector. Samples were injected (50 μl) by a Waters 2707 autosampler prior to compound separation by a Gemini C-18 column (150×2.00 mm, 5μ, 110 Å, Phenomenex). The HPLC method utilized a flow rate of 0.5 ml/min and a binary gradient (solvent A: 5% acetonitrile/5% MeOH/10 mM ammonium acetate/15 mM NH$_4$OH and solvent B: 90% acetonitrile/10 mM ammonium acetate/15 mM NH$_4$OH), 0-2.0 min 0% B, 2.0-9.0 min 0-44% B, 9.0-11.0 min 44-100% B, 11-13 min 100% B and 100-0% B from 13-14 min and held at 0% B for an additional 4 min. Samples were quantitated by standard curve using peak area with the software Breeze 2.

7.0 Induction Experiment for RNA Extraction.

A single colony resuspended in 5 ml of LB was used to inoculate three 1 L flasks (A-C) containing 250 ml of LB media where 1 ml of the suspension was aliquoted to each flask. The cultures were incubated at 28° C. for 7 days then moved to 21° C. Flask A, cultured only in LB media, was collected at day 8 by centrifugation (3000×g, 15 min, 4° C.) and the final pellet was resuspended in 4 ml of RNA-later (Ambion). The culture was then collected by centrifugation (3000×g, 15 min, 4° C.) and flash frozen in a dry ice/ethanol bath. This culture was considered to not be induced for MND enzyme production.

Flasks B-C were collected at day 7 and washed (2000×g, 15 min, RT) 3 times with 20 ml of MODLS+thebaine and resuspended in 10 ml of MODLS+thebaine and moved to a 1 L flask containing 250 ml of MODLS+thebaine immediately prior to incubation at 21° C. Suspension of cells previously grown in LB then cultured in MODLS+thebaine was performed to induce the production of MND enzyme. Cells were collected at 3 days (flask B) and 6 days (flask C) post-induction in the same manner as flask A.

Prior to collection, 1 ml of each culture was plated on LB media to check for contamination and 200 μl of each sample were extracted by addition of 400 μl sodium carbonate buffer (pH 9.5) and 400 μl chloroform by 1 min rapid mixing followed by centrifugation (16,000×g 2 min RT). The extraction was repeated once and dried to completion under N2. Dried samples were resuspended in 200 μl 80% methanol and diluted 1/10 before LC-MS/MS analysis.

8.0 RNA Extraction.

Modified from Giannoukos et al. *Genome Biology* 2012 13: r23. Cells were thawed on ice and aliquoted into 16×1.5 ml sterile, RNAse free microcentrifuge tubes and pelleted by centrifugation (4,000×g, 10 min, RT). The supernatant was removed and the cells were resuspended in 200 μl of bacterial lysis buffer (30 mM tris.HCl pH 8.0, 1 mM EDTA), 15 mg/ml lysozyme, and 20 μl of proteinase K. Samples were incubated at room temp for 10 min with rapid mixing for 10 s every 2 min. RNA extraction proceeded using RLT buffer in the RNeasy Plant Mini Kit (QIAGEN). The remainder of the extraction followed manufacturer's instructions. Samples were combined and precipitated using LiCl precipitation solution (Ambion) and resuspended in 100 μl of RNase free H2O. RNA was treated with DNase (Ambion) and followed by another LiCl precipitation. RNA concentration was determined using a nanodrop and RNA integrity was evaluated with an Agilent Bioanalyzer 2100.

9.0 Transcriptome Sequencing.

Library preparation and sequencing using Illumina Miseq (2X300 run, 40 million reads) was performed by MOgene (found on the world wide web at mogene.com).

10.0 Transcriptome Assembly.

Raw reads were first normalized using Fulcrum (Burriesci et al. 2012) prior to trimming with Trimmomatic (Bolger et al. 2014) for quality processing. Trimmed reads were then assembled with Trinity (Grabherr et al. 2011) using default parameters. A homology search was performed on the resulting contigs using BLAST (found on the world wide web at blast.ncbi.nlm.nih.gov/Blast.cgi). Blast results were analyzed and filtered for quality in two steps. First, contigs were filtered based upon the meaningfulness of the alignment. Contigs having a 15% or lower alignment with an existing sequence in the BLAST NR database were discarded. However, contigs having a length over 500 base pairs were kept, regardless of alignment. Second, contigs were filtered based upon homology to known organisms by an additional BLAST search against a database consisting of human, zebrafish, *Arabidopsis, C. elegans, D. melanogaster,* and yeast. Contigs with significant alignment to these organisms were discarded. The remaining contigs were used for determining expression data with BWA (Burrows-Wheeler Aligner) (Li and Durbin 2009) in conjunction with the raw reads. Open reading frames in the filtered set of contigs were estimated using an in-house algorithm based upon BLAST.

11.0 HAYSTACK Analysis and Candidate Gene Selection.

Production of northebaine on induced cultures was quantitated and used as the model for HAYSTACK (found on the world wide web at haystack.mocklerlab.org) (Mockler et al. 2007) to mine the expression data of Thebainfresser contigs (gene transcripts). The following parameters were used for HAYSTACK: correlation cutoff 0.8, fold cutoff 2, P-value 0.05, and background cutoff 1. Transcripts that demonstrated an induction pattern that mirrored the accumulation of northebaine in the Thebainfresser-inoculated culture medium were selected for further analysis.

12.0 Thebainfresser DNA Extraction.

Thebainfresser was grown for 2 months in MODLS+ thebaine media prior to DNA extraction. DNA extraction was as previously described (William and Copeland 2012).

13.0 Cloning of Candidate Genes.

Four genes belonging to two clusters were chosen for analysis based upon their expression pattern and putative annotation. The MND enzyme coding region was cloned using primers for nested PCR and addition of restriction sites for cloning (respectively).

```
comp7134_5_UTR_f:
                                    (SEQ ID NO: 4)
CCGATCTATGACGGGATATCTGGGA Tfcont_9516_3UTR_RC:
                                    (SEQ ID NO: 5)
TGACGCGACAATCCCTCTACC comp7134_f_NdeI:
                                    (SEQ ID NO: 6)
CACCATATGACTGAAAAAACGCCTAAACTAG Tfcont_9516_EcoRI_RC:
                                    (SEQ ID NO: 7)
GAGGAATTCTCAGATTTTAGGGAAGACATTCGCAACC.
```

PCR was performed using Phusion DNA polymerase (NEB) and the following cycle parameters: 98° C. 30 sec (1 cycle), 98° C. 10 sec 56° C. 30 sec, 72° C. 2 min (35 cycles), and 72° C. 10 minutes (1 cycle). The MND enzyme-encoding fragment was digested and ligated into the pET28a expression vector and cloned into both BL21 Star (DE3) (Invitrogen) and PLUSE expression strains of *E. coli.* PLUSE cells also expression the GroES and GroEL chaperone proteins to assist in protein folding.

14.0 Toluene Permeabilization Assay.

14.1 Multiple Enzyme Testing.

Enzyme activity was first tested by permeabilization of BL21 Star (DE3) cells expressing each gene by toluene treatment based upon work by Paoni N. and Koshland D (Paoni and Koshland 1979). Cells growing at 30° C. in terrific broth (TB) were first induced with 100 µM IPTG and transferred to 16° C. for 24 hours. Cells were collected by centrifugation (3,000×g, 10 minutes, RT) then reconstituted in TB to a final OD of 2. Toluene was added to 5 ml of each culture to 0.14% and subject to rapid mixing for 2 minutes. Cultures were incubated for 1 hr at 30° C. Cells were then collected by centrifugation (3,000×g, 10 minutes, 4° C.), washed with 5 ml TB, and brought up to a total volume of 10 ml in TB. Thebaine was added to a final concentration of 20 µM (200 nmol) and cultures were incubated overnight at 30° C., 200 rpm. The next day, 5 ml of each culture was extracted with equal volume ethyl acetate and dried to completion with N2. Dried samples were resuspended in 200 µl of 80% MeOH before diluting $\frac{1}{100}$ for analysis on the QTRAP 6500 using method 1.

14.2 MND Enzyme Activity Verification, Performed in Triplicate Testing Two Individual Colonies Encoding the MND Enzyme and pET28a in BL21 Star (DE3).

Two individual colonies of both pET28a empty vector and MND enzyme-encoding clones in pET28a (with N-terminal His-tag) transformed into BL21 Star (DE3) cells were cultured, in triplicate, in 2.5 ml of terrific broth (TB) (Tartoff and Hobbs 1987) media supplemented with 50 µg/ml kanamycin at 30° C. overnight. The next morning, after the addition of 4.5 ml of TB media, cultures were induced with 100 µM IPTG and transferred to 16° C. for 24 hours. Cells were collected by centrifugation (3,000×g, 10 minutes, 4° C.) then reconstituted in TB to a final OD of 2. Toluene was added to 5 ml of each culture to 0.14% and mixed gently for 2 minutes. Cultures were incubated for 1 hr at 30° C., 200 rpm. Cells were then collected by centrifugation (3,000×g, 10 minutes, 4° C.), washed with 5 ml TB, and brought up to a total volume of 10 ml in TB. Thebaine was added to a final concentration of 20 µM and cultures were incubated overnight at 30° C., 200 rpm. The next day, 5 ml of each culture was extracted with equal volume ethyl acetate and dried to completion with N2. Dried samples were resuspended in 200 µl of 80% MeOH before diluting $\frac{1}{100}$ for analysis on the QTRAP 6500 using method 1.

15.0 Protein Purification.

Protein purification was performed on pET28a empty vector and the MND enzyme-encoding clones in pET28a (with N-terminal His-tag) transformed into BL21 Star (DE3) and PLUSE expression strains by culturing cells in 300 ml of TB media supplemented with 50 µg/ml kanamycin (BL21 Star (DE3) cells) or 50 µg/ml kanamycin and 32 µg/ml of chloramphenicol (PLUSE cells) for 12 hours at 30° C., 180 rpm. The following day, 600 ml of TB media supplemented with appropriate antibiotics and IPTG (100 µM final concentration) were added to each culture. Cells were incubated at 15° C., 180 rpm for 24 hours. Cells were then collected (8,000×g, 10 min, RT), resuspended in 15 ml EB (50 mM sodium phosphate pH 7.0, 300 mM NaCl, 10% glycerol), and lysed. Lysis was achieved by addition of 1.75 ml of 10 mg/ml lysozyme followed by incubation at RT for 20 min with gentle agitation and sonication (repeat 5×, 15 s each, pulse 5). Cell lysate was collected (20,000×g, 20 min, 4° C.) and added to 2 ml TALON metal affinity resin (Clontech) which was washed twice with EB (700×g, 2 min, 4° C.) and kept on ice. The resin/protein mixture was incubated for 1 h on ice with gentle shaking then washed twice with 20 ml EB (700×g, 5 min 4° C.). The final pellet was resuspended in 2.5 ml of EB and placed into a Talon 2 ml disposable gravity column (Clontech). The protein bound resin was washed with EB supplemented with 5 mM imidazole and the protein was eluted with EB supplemented with 100 mM imidazole. The protein was then desalted using 50 mM potassium phosphate buffer pH 8.0 and PD-10 Desalting Columns (GE Healthcare) according to manufacturer's instructions.

16.0 Purified MND Enzyme Assays Using Thebaine as Substrate.

16.1 Enzyme Assay with MND Enzyme Purified from BL21 Star (DE3) Cells.

Enzyme assays included 100 µl of MND enzyme purified protein preparations (~36 µg) incubated in 30 mM potassium phosphate buffer (pH 8.0) with 7.5 µM (1500 pmol) thebaine, in a total volume of 200 µl at 30° C. overnight. No enzyme, boiled enzyme, and purified empty vector controls were included. MND enzyme was heated for 10 min at 95° C. for the boiled enzyme control. Assays were extracted twice with 400 µl ethyl acetate and dried to completion with N2. Dried samples were resuspended in 150 µl of 50% MeOH, filtered (low protein binding 0.2 µm, 4 mm, PTFE; Millipore), and diluted 100 fold prior to LC-MS/MS analysis on the QTRAP 6500 using method 1 and a 5 µl injection volume.

16.2 Enzyme Assay on MND Enzyme Purified from PLUSE Cells.

Enzyme assays using the purified MND enzyme protein produced in PLUSE cells were done, in duplicate, as indicated above with the following exceptions: 10 µl of 100 µM codeine standard was added to each assay, prior to extraction, as an internal standard. Dried extracts were resuspended in 200 µl of 50% MeOH, filtered (0.2 µm, 4 mm, PTFE, Millipore). Samples were diluted 50 fold prior to a 5 µl injection onto the QTRAP 6500 using method 1.

17.0 SDS-PAGE for Protein Purification.

17.1 SDS-PAGE for MND Enzyme from BL21 Star (DE3) Cells.

Protein purification was analyzed by SDS-PAGE using the Mini-PROTEAN Tetra system and a 10% mini-PROTEAN TGX gel. Samples were denatured in Laemmli Sample Buffer supplemented with β-mercaptoethanol by heating at 95° C. for 10 minutes prior to analysis.

17.2 SDS-PAGE on MND Enzyme in PLUSE Cells.

Samples for SDS-PAGE were processed as above and analyzed on a 10% gel.

17.3 SDS-PAGE for Protein Quantitation.

His-tag purified MND enzyme samples were quantitated with SDS-PAGE using the method in 17.1 by comparison to pure BSA standards. The following concentrations of BSA were run alongside MND enzyme samples: 3,000 ng, 2,000 ng, 1,500 ng, 1,000 ng, and 800 ng. MND enzyme samples were run in triplicate. Imaging was performed with a GelDoc EZ Imager (BIORAD) and the samples were quantitated using Image Lab version 5.2.1. The band running at the predicted size of 72 kD was used for subsequent calculations.

18.0 MND Enzyme in Bl21 Star (DE3) Cells Vs. PLUSE Cells: Permeabilization Assay.

18.1 Permeabilization of Bl21 Star (DE3) and PLUSE *E. coli* Cells Expressing MND Enzyme with Toluene Incubated with Thebaine and Northebaine Production Analysis.

Permeabilization assays were carried out as above, in triplicate, for MND enzyme-encoding vectors transformed into both BL21 Star (DE3) and PLUSE cells. Cells transformed with the empty vector pET28a were included as a control. Samples were also extracted as above but the dried extracts were resuspended in 200 µl of 80% MeOH prior to filtration and 100 fold dilution. Samples were analyzed and quantitated by QTRAP 6500 using method 1 with a 2 µl injection volume.

18.2 SDS PAGE on MND Enzyme-Encoding Vectors and pET28a Transformed into BL21 Star (DE3) and PLUSE Cells Cultured for Permeabilization Assay.

The OD600 of each culture was measured and used to normalize each sample concentration prior to analysis by SDS-PAGE by using 6 µl of sample per an OD600 of 10. The varying amounts of cultures were then centrifuged (16,000× g, 5 min, RT) and 20 µl of Laemmli Sample Buffer supplemented with β-mercaptoethanol was added to each pellet and heated at 95° C. for 10 minutes prior to SDS-PAGE using a 7% gel.

19.0 Poppy Seed Inoculation Experiment.

Thebainfresser grown in LB media were used to inoculate 10 seeds each of three *Papaver sominferum* cultivars, Munich, Nopa (Norman parent), and Norman by rotating the seeds at room temperature for both 1 hour and 24 hours. Seeds were also incubated in LB only as a control. Each experiment was performed in triplicate. Seeds were planted immediately post inoculation in Metromix 360 soil and cultivated on site in the greenhouse (Donald Danforth Plant Science Center, St. Louis Mo.). Leaf tissue was harvested from each plant 55 days after planting. The leaves chosen were newer and all from the same developmental stage (about the 10th leaf from the original true leaves), and frozen in liquid nitrogen immediately post-harvest. Capsules were harvested after petal fall and the latex from one of each experimental group and control were streaked out onto MODLS+thebaine agar plates to monitor for growth of Thebainfresser.

20.0 MND Enzyme Substrate Testing.

Substrates were prepared in a 1 mM stock concentration then diluted to 100 µM working concentration for use in enzyme assays with the MND enzyme. Ethanol was added to the stock solutions to aid in solubility for compounds that did not dissolve easily in water. No more than 15% ethanol was added to the 1 mM concentrations. The following substrates were tested: oripavine, (R)-reticuline, salutaridine, salutaridinol, heroin, thebaine, morphinone, codeinone, codeine, morphine, hydromorphone, oxymorphone, galanthamine, laudanine, orientaline, protosinomenine, isoorientaline, laudanosine, (S)-reticuline, scopolamine, hyoscyamine, noscapine, tropinone, physostigmine, isothebaine, (−)-lobeline, gramine, and autumnaline. Several other substrates were also tested with no detectable activity, but reasons for this could be attributed to solubility and detection issues, therefore these results were considered inconclusive. All enzyme assays contained 30 mM potassium phosphate buffer pH 8.0, 7.5 µM substrate and 100 µl of purified MND enzyme (~36 µg) in a total volume of 200 µl. Duplicate assays of each substrate using purified pET28a empty vector were performed as negative control and an assay containing thebaine and MND enzyme was used as a positive control. Assays were incubated at 30° C. overnight prior to ethyl acetate extraction. All samples were diluted 10 fold with 50% MeOH and analyzed on the QTRAP 6500 using method 2 and a 20 µl injection volume. The percentage of substrate demethylation was calculated based upon reduction of substrate in the enzyme assay as compared to the negative control. The calculations were based on overnight assays which are most likely out of the enzyme's linear range. Therefore, the percentages should be considered approximate.

21.0 *Agrobacterium* Mediated Transformation of MND Enzyme-Encoding Vectors into *Camelina sativa*.

The PCR product containing the MND enzyme open reading frame cut with NdeI and BamHI was ligated into the vector pKL11-gly (digested with the same enzymes) then transformed into *E. coli* DH5 α. The vector pKL11-gly is a small *E. coli* vector containing the Glycinin promoter and terminator from soybean and an ampicillin resistance gene. The entire expression cassette containing the Glycinin promoter, MND enzyme coding region, and Glycinin terminator was then amplified by PCR using the following primers to add the AvrII and RsrII restriction sites (respectively):

```
GLYP_AvrII_F
                                                    (SEQ ID NO: 8)
(5'-ATGGTACCTAGGGTACGTAAGTACGTACTCAA-3').

GLYT_RsrII_Rev
                                                    (SEQ ID NO: 9)
(5'-CACTCACGGACCGAAGTCATGAAGAACCTGATAAGAC-3').
```

The PCR product was then digested with AvrII and RsrII and ligated into pRSe3 vector (Augustin et al. 2015) cut with the same enzymes. The ligation reaction was first transformed into *E. coli* DH5α for sequence verification then transformed into the *Agrobacterium* strain GV3103 pMP90. *Camelina sativa* Suneson and *Camelina sativa* Licalla were both transformed with the MND gene via *agrobacterium* (Lu and Kang 2008). In addition, a synthetic version of an MND enzyme coding region, encoding the identical amino acid sequence as the MND enzyme but codon optimized for *Arabidopsis thaliana*, a relative of *C. sativa*, was ordered (Genewiz) and cloned into pRSe3 and transformed into *C. sativa* using the same procedure.

22.0 Phylogenetic Analysis

The MND enzyme protein sequence was subject to a protein BLAST (Camacho et al. 2009) search using the NR database at NCBI to obtain the most closely related sequences known. Sequences were aligned with MUSCLE and a maximum likelihood tree (500 bootstraps) was created with MEGA v 6.06 (Tamura et al. 2013).

23.0 Temperature Optimum Assay

Enzyme assays with 100 μl purified MND enzyme (~36 μg), 7.5 μM thebaine, and 30 mM potassium phosphate pH 8.0 in a total assay volume of 200 μl were performed in duplicate and allowed to incubate at the following temperatures for 20 minutes: 20° C., 25° C., 30° C., 40° C., 50° C., 60° C., 70° C. and 80° C. Assays with purified pET28a empty vector control were included at each temperature. Assays were quenched by the addition of 400 μl MeOH followed by rapid mixing for 30 s then subject to centrifugation (16,000×g, 30 min, RT). Samples were diluted further (total of 50 fold dilution) to achieve an analyte concentration of 0.15 μM prior to filtration (low protein binding 0.2 μm, 4 mm, PTFE; Millipore) and introduction into the QTRAP 6500 using Method 1.

24.0 pH Optimum Assay

Enzyme assays with 100 μl purified MND enzyme (~36 μg), 7.5 μM thebaine, and 60 mM buffer (citrate buffer pH 4 and pH 5, potassium phosphate buffer pH 6.0, pH 7.0, and pH 8.0, and glycine-NaOH buffer pH 9, pH 10, and pH 10.5) in a total assay volume of 200 μl were allowed to incubate at 30° for 20 minutes. Assays with no enzyme and a purified pET28a empty vector control in pH 8.0 were included. The remaining protocol was the same as for the temperature optimum above. A supplemental pH assay was run in the same manner as above to verify the low pH results using a glycine-HCL buffer for pH 2, 3, and 4 and citrate buffer for pH 4, 5, and 6.

25.0 Kinetic Assay

Kinetic assays were performed in triplicate with 100 μl purified MND enzyme (~36 μg) using 30 mM potassium phosphate buffer pH 7.0 at 30° C. in a total volume of 200 μl and allowed to proceed for 20 min. The following substrate concentrations were used 0 μM, 0.5 μM, 1 μM, 5 μM, 10 μM, 15 μM, 20 μM, 30 μM, 40 μM, and 50 μM. No enzyme and empty vector controls were also included. Assays were quenched, filtered, and diluted as in section 23.0 and analyzed using Method 1. Kinetic parameters were determined using Prism 7 version 7.01.

26.0 MND Enzyme Stability Assay

100 μl purified MND enzyme (~36 μg) was incubated in 30 mM potassium phosphate buffer pH 7.0 at 30° C. for 72, 48, 24, 6, 3, and 1 hours prior to addition of 1500 pmol thebaine in a total volume of 200 μl. The assay was allowed to proceed for 20 minutes after substrate addition and was processed and analyzed as in section 23.0.

27.0 MND Enzyme Treatment with Proteinase K and Addition of Several Cofactors to Determine Effects on Enzymatic Conversion of Thebaine to Northebaine The first of two assays performed included adding 1500 pmol FAD to the 200 MND enzyme assay including 100 μl purified MND (~36 μg) and 1500 pmol thebaine in 30 mM potassium phosphate buffer pH 7.0 with and without a prior 1 hour digest (of MND enzyme) with Proteinase K. Controls included a no enzyme control, FAD addition to a no enzyme control, a pET28a empty vector control, a pET28a empty vector control with FAD, and a pET28a empty vector control digested with Proteinase K followed by FAD addition. Assays were allowed to incubate for 20 minutes and then processed as in section 23.0. A second set of assays was performed, in duplicate, to validate the results found in the previous assay in addition to testing more cofactors. This assay included the following conditions; MND enzyme, MND enzyme pre-digested with Proteinase K for 1 hour, MND enzyme digested with Proteinase K in the presence of 1% SDS and 10 mM EDTA, MND enzyme with 1% SDS and 10 mM EDTA (no Proteinase K pre-digestion), pET28a empty vector, pET28a empty vector pre-digested with Proteinase K for 1 hour, pET28a empty vector digested with Proteinase K in the presence of 1% SDS and 10 mM EDTA, MND enzyme with the addition of 1500 pmol FMN, pET28a empty vector with the addition of 1500 pmol FMN, MND enzyme with the addition of 1500 pmol PLP and pET28a empty vector with the addition of 1500 pmol PLP. Assays were allowed to proceed for 20 minutes prior to processing and quantitation as described in section 23.0.

28.0 Attachment of MND to Sepharose Beads 1 mg of His-tagged purified MND underwent buffer exchange into 0.1 M NaHCO$_3$/0.5 M NaCl buffer using a PD-10 column (GE Healthcare) and concentrated to 1 ml using 3K Amicon filter (Millipore). The sample was then coupled to CNBr-activated Sepharose™ 4B (GE Healthcare) following manufacturer's instruction with the following modifications. The recommended volumes were reduced by ¹⁄₁₄ and washes were performed using vacuum filtration in a DNA plasmid purification column (Qiagen). After attachment, the column was washed several times before the final wash with 0.1 M potassium phosphate buffer pH 7.0. Some buffer remained in the column and 1500 pmol of thebaine was added to the stopped up column. After 20 minutes, the column was subject to centrifugation and the sample was collected. The column was stopped up again and 200 μl of 0.1 M potassium phosphate buffer pH 7.0 was added in addition to 1500 pmol of thebaine. Thebaine was incubated overnight and collected the next morning. 1500 pmol of thebaine was also added to 200 μl of NaHCO$_3$ wash (after initial ligand binding) with and without residual beads, to phosphate buffer only, and to a mix of the acid/base wash as controls.

29.0 Testing of MND in Different *E. coli* Strains

His-tagged MND and empty vector pET28a was transformed into PlusSa *E. coli* cells (expressing skp chaperone protein) and BL21 (DE3) pLysS. The following cells lines were tested for active protein production by toluene permeabilization assay, in duplicate, that contained His-tagged MND and an empty vector control: BL21 Star (DE3), PlusE, pLysS, and PlusSa. Cell growth was normalized and subjected to toluene permeabilization and incubation with thebaine. Northebaine production was detected and quantified by LC-MS/MS using method 2.

30.0 AKTA Protein Purification for Determination of Native Protein Size and Quaternary Structure Additional protein purification after cobalt column was performed using the AKTA purifier (GE Heathcare) fitted with P-900 pumps, UV-900 monitor, and the Frac-920 fraction collector. Protein was separated on a HiLoad 16/600 Superdex 200 prep grade size exclusion column with a flow rate of 1 ml/min. For MND, 1 ml protein was loaded (350-850 μg/ml) after filtration with 0.45 GHP (Pall) syringe filter. A gel filtration standard (Bio-Rad cat. #151-1901) was reconstituted according to manufacturer's instructions and run prior to MND. Data was analyzed using Unicorn 5.10.

31.0 Protein Sequencing of Both Bands Detected by SDS-PAGE

About 8.5 μg of HIS-tagged MND purified by cobalt resin was run on SDS-PAGE as previously described. The two prominent bands that appear on the gel were excised separately and sequenced by the Proteomics and Mass Spectrometry Facility at the Donald Danforth Plant Science Center. The Results were analyzed by Scaffold™ version 4.7.2.

32.0 Morphinan N-Demethylase (the MND Enzyme)

32.1 Cofactor Identification

Due to the reaction type and color of the purified protein, it was suspected that the enzyme contained a co-factor. After methanol precipitation of MND and an empty vector control, the supernatant was analyzed by LC-MS/MS for potential cofactors. A large peak for FAD, but not FMN or any other cofactor, was detected in the MND containing samples and not in the pET28a containing samples.

32.2 Protein Analysis: Sequence, Native Size, and Tertiary Structure

Purified His-tagged MND analyzed by SDS-PAGE revealed two prominent protein bands around 60 and 75 kD. In order to verify the bands, and determine if one was a processed peptide of MND, the bands were excised and sequenced. The larger band corresponded to a weight of about 74 kD and was indeed the His-tagged version of MND. Also of note, the first methionine appeared to be cleaved. The smaller band had a calculated size of about 57 kD and turned out to be the *E. coli* GroEL chaperone protein. MND protein purified by FPLC using a size exclusion column with the AKTA protein purification system successfully separated the GroEL chaperone protein from MND. The activity, however, was variable and with the amount of lost material and activity, this purified form was not chosen for further analysis. However, a gel filtration standard was run directly prior to a run with MND to verify native size. The MND protein band (verified after fraction collection by enzyme assay) eluted between the Gamma-globulin (158,000 kD) and the Ovalbumin (44,000) protein standard, indicating the protein, in its native form, is most likely the predicted size of 74 KD and therefore exists as a monomer.

Figure 1B:
FIG. 1B.
Figure 2A:
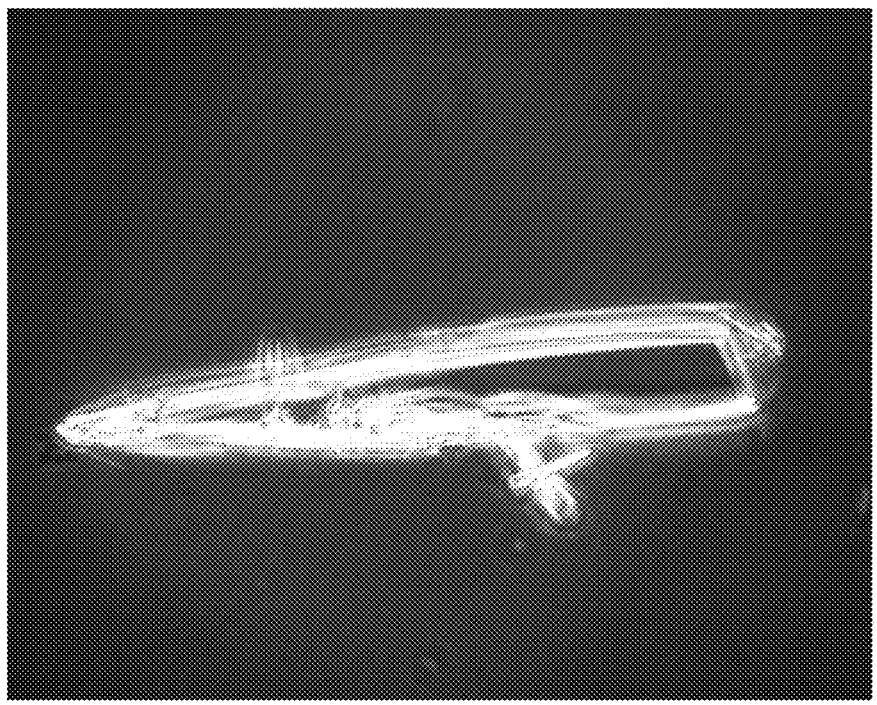
FIG. 2A.
Figure 2B:
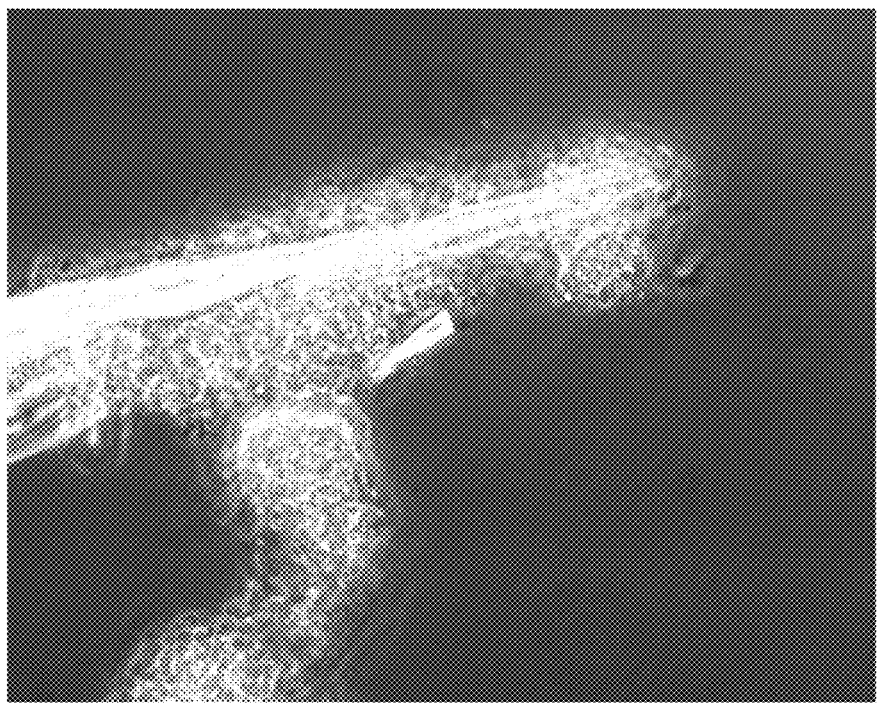
FIG. 2B.

Results 33.0 Thebainfresser Isolation, Growth, and Morphological Characteristics A sludge pond sample was added to minimal media containing thebaine as the sole carbon source (MODLS+thebaine). Incubated under non-sterile conditions at room temperature over many months, eventually microbial growth was observed. The culture was then subcultured under the same conditions until remnants of the original sludge sample were no longer observed, but microbial growth was consistently achieved. The bacterium producing the thebaine-demethylating enzyme that was eventually isolated was one in a complex mixture of soil microorganisms (both bacterial and fungal) from the sludge pond sample. After multiple rounds of serial dilutions on various media, the organism producing the desired N-demethylation reaction was isolated. The organism had pink pigment (FIG. 1B) and grew on LB media and MODLS+thebaine media but not on Potato Dextrose Agar media. Colonies could be seen developing on LB media in 5-7 days, but took about a month to grow on MODLS+thebaine. Microscopic images of Thebainfresser growing in MODLS+thebaine showed morphology of rod shaped bacteria (FIG. 1A). Further microscopic analysis of MODLS+thebaine incubated alone (FIG. 2A) and MODLS+thebaine cultured with Thebainfresser (FIG. 2B) showed the Thebainfresser colonizing on the thebaine crystals.

Figure 3:
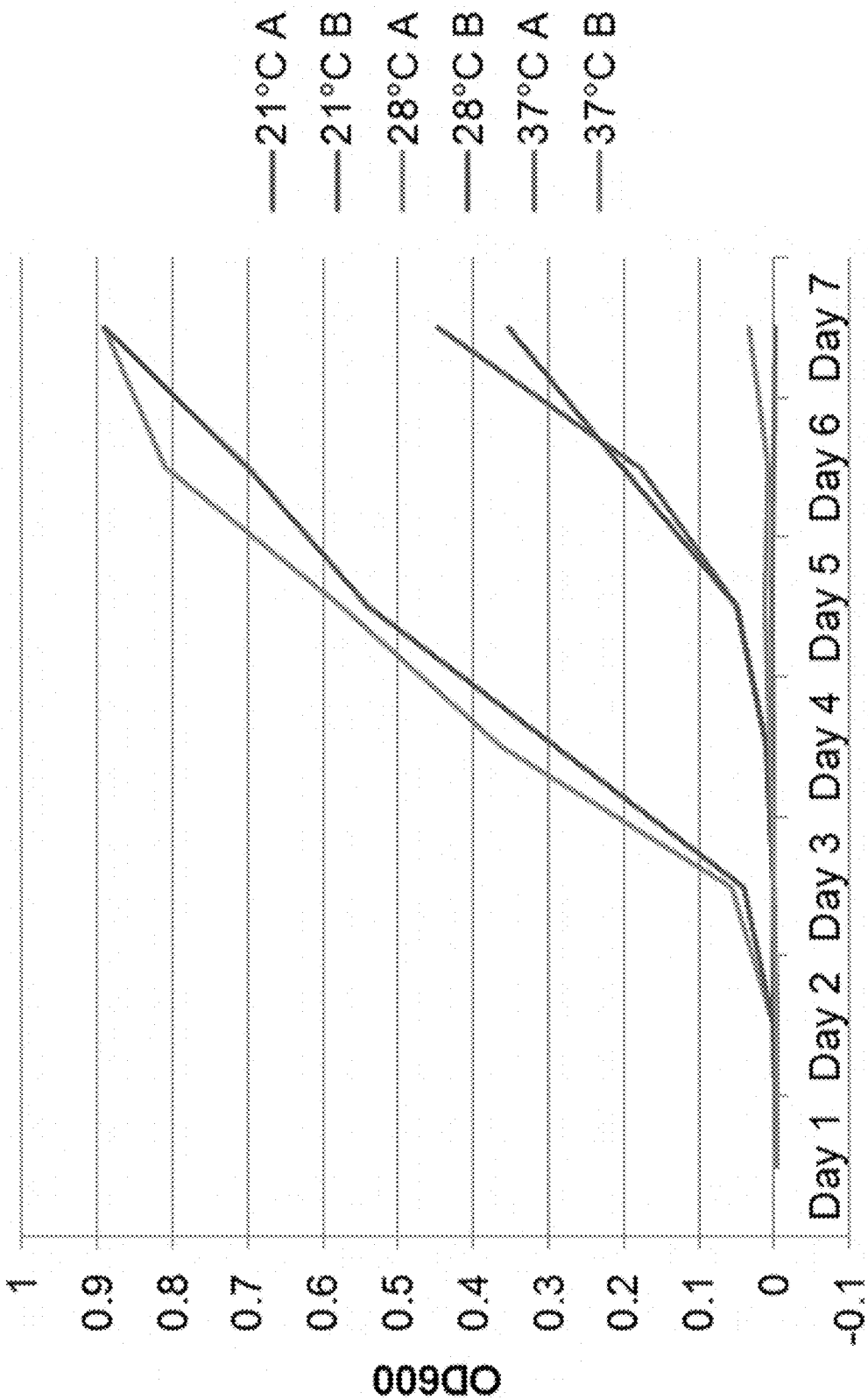
FIG. 3.

In order to determine the best growth conditions for culturing Thebainfresser, cultures were incubated at different temperatures and density was observed. Thebainfresser was cultured at 21° C., 28° C., and 37° C., in duplicate, and the cell density was measured spectrophotometrically using OD600 (FIG. 3). Thebainfresser grew to a higher culture density at 28° C.

34.0 N-Demethylase Enzyme Induction, RNA Extraction, and Sequencing

Figure 4:
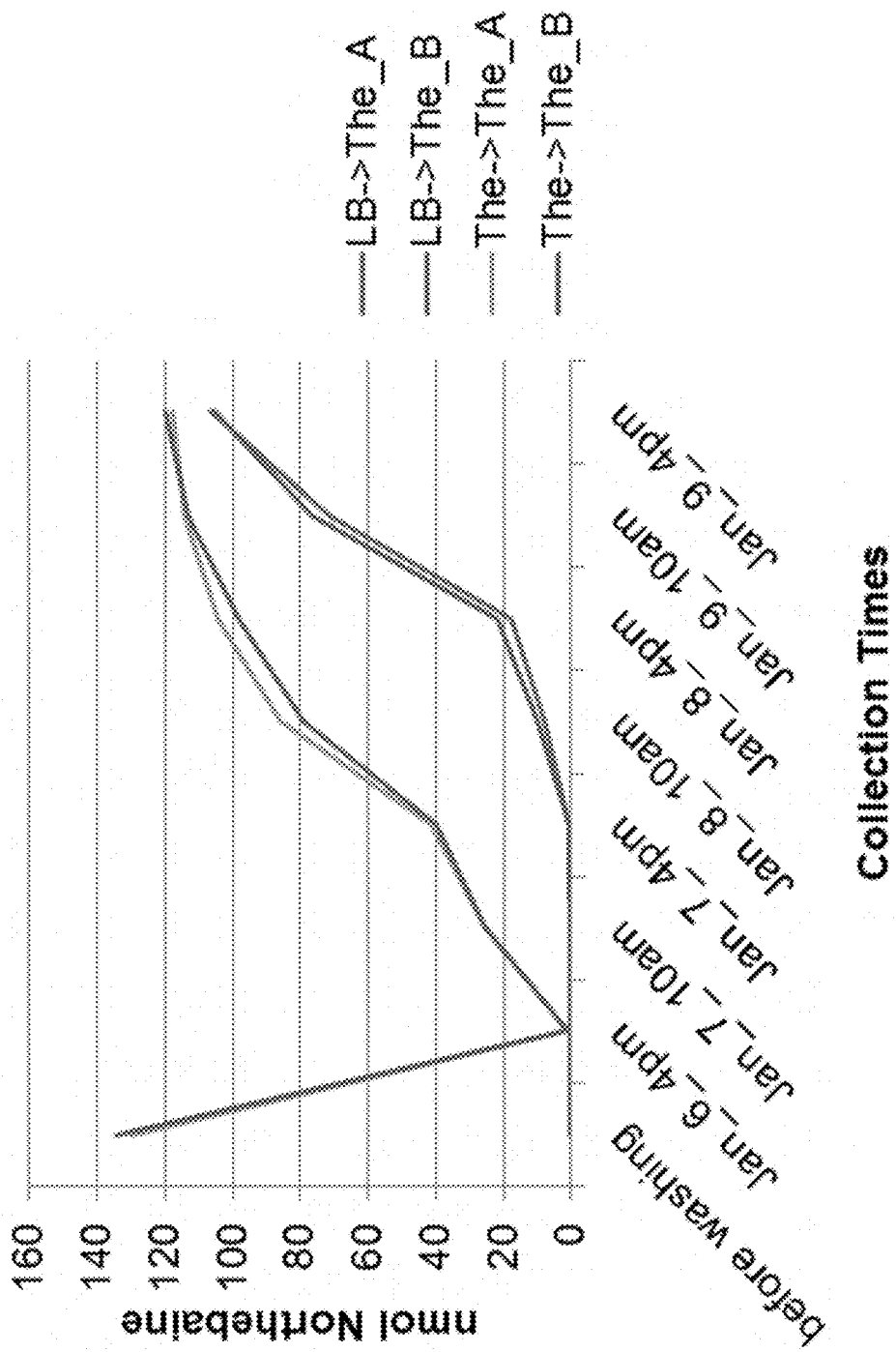
FIG. 4.

In order to determine if the N-demethylating enzyme of interest was induced upon growth in a media lacking a carbon source other than thebaine, an induction experiment was performed. Cultures growing in nutrient rich LB media and cultures growing in MODLS+thebaine were washed with and resuspended in MODLS+thebaine. The amount of northebaine produced was monitored over several days (FIG. 4). The lag in northebaine accumulation in cultures growing in LB media indicated that production of the MND enzyme was induced under low carbon and nutrient poor conditions.

RNA was extracted from cultures grown under three conditions; 1) LB only (Day 0), 2) LB then washed and resuspended in MODLS+thebaine for 3 days (Day 3), and 3) LB then washed and resuspended in MODLS+thebaine for 6 days (Day 6). The RNA was then check for quality using the Bioanalyzer and sent to MoGene for library preparation and Illumina sequencing using MiSeq. MoGene ran the samples twice and provided us with both sets of raw reads. The number of reads, length of reads, and the GC content of each set are presented in Table 1. UND indicates undetermined reads that could not be positively associated with any of the three samples.

35.0 Thebainfresser Transcriptome Assembly

The raw reads for Day 0, Day 3, and Day 6 from both Illumina Miseq runs were used in the assembly. Raw reads were normalized using Fulcrum (Burriesci et al. 2012) and trimmed with the Trimmomatic (Bolger et al. 2014) program. The processed reads were then assembled with Trinity (Grabherr et al. 2011). The number of contigs produced by trinity was 829,495 (Table 2). These contigs were then submitted to BLAST, and the resulting annotations suggest that the organism is a Pink Pigmented *Methylobacterium* (*Methylobacterium* spp) as 37% of contigs significantly aligned to *Methylobacterium* while 53% had no significant hits. Many of the contigs had confident annotations for *Homo sapiens* (Human), *Cricetulus griseus* (Chinese Hamster), and others. These contigs that had no hits in the database or significantly aligned to eukaryotes were removed. Statistics for our trinity assembly throughout the filtering process, in addition to statistics for two known metholybacteria are presented in Table 2. The similar GCcontent (65%) and number of contigs (6,792) found in our assembly compared to the known methylobacteria suggest our final transcriptome is of high quality.

36.0 Candidate Gene Selection

Gene expression was determined by aligning raw reads to the transcriptome using BWA (Li and Durbin 2009). The expression dataset was then mined using HAYSTACK (Mockler et al. 2007) to find contigs (gene transcripts) that had an expression pattern consistent with the production of northebaine in the induced cultures (FIG. 4). The HAYSTACK analysis resulted in 34 contigs whose expression pattern fit the model. The list was curated to produce 4 candidates for cloning based upon annotation and length of open reading frame. Candidate A annotated as an ethanolamine utilization protein, candidate B annotated as a diguanylate cyclase, candidate C annotated as a glutamine synthase, and candidate D annotated as an FAD-dependent oxidoreductase.

37.0 Identification of Morphinan N-Demethylase ("the MND Enzyme")

Figure 5:
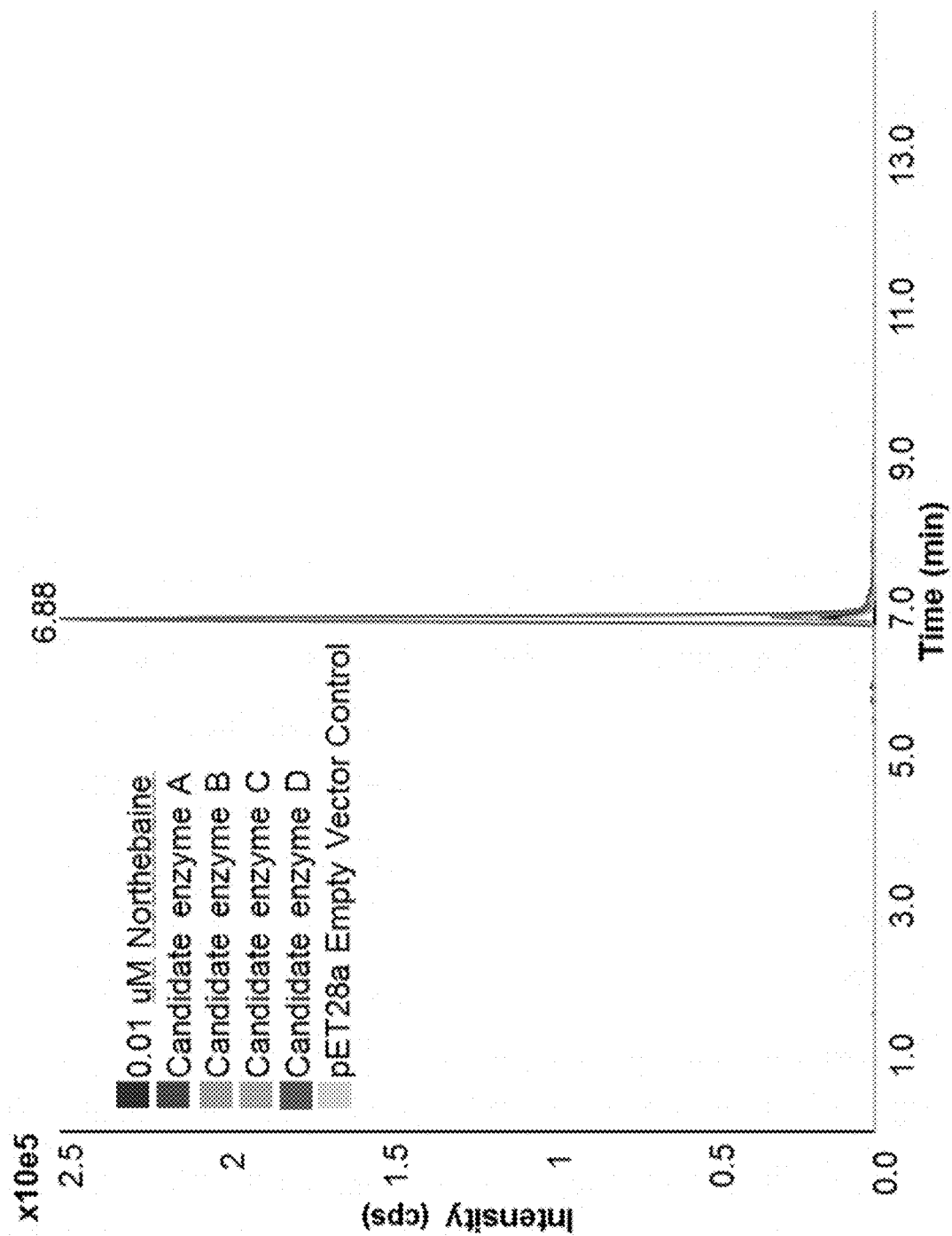
FIG. 5.
Figure 6:
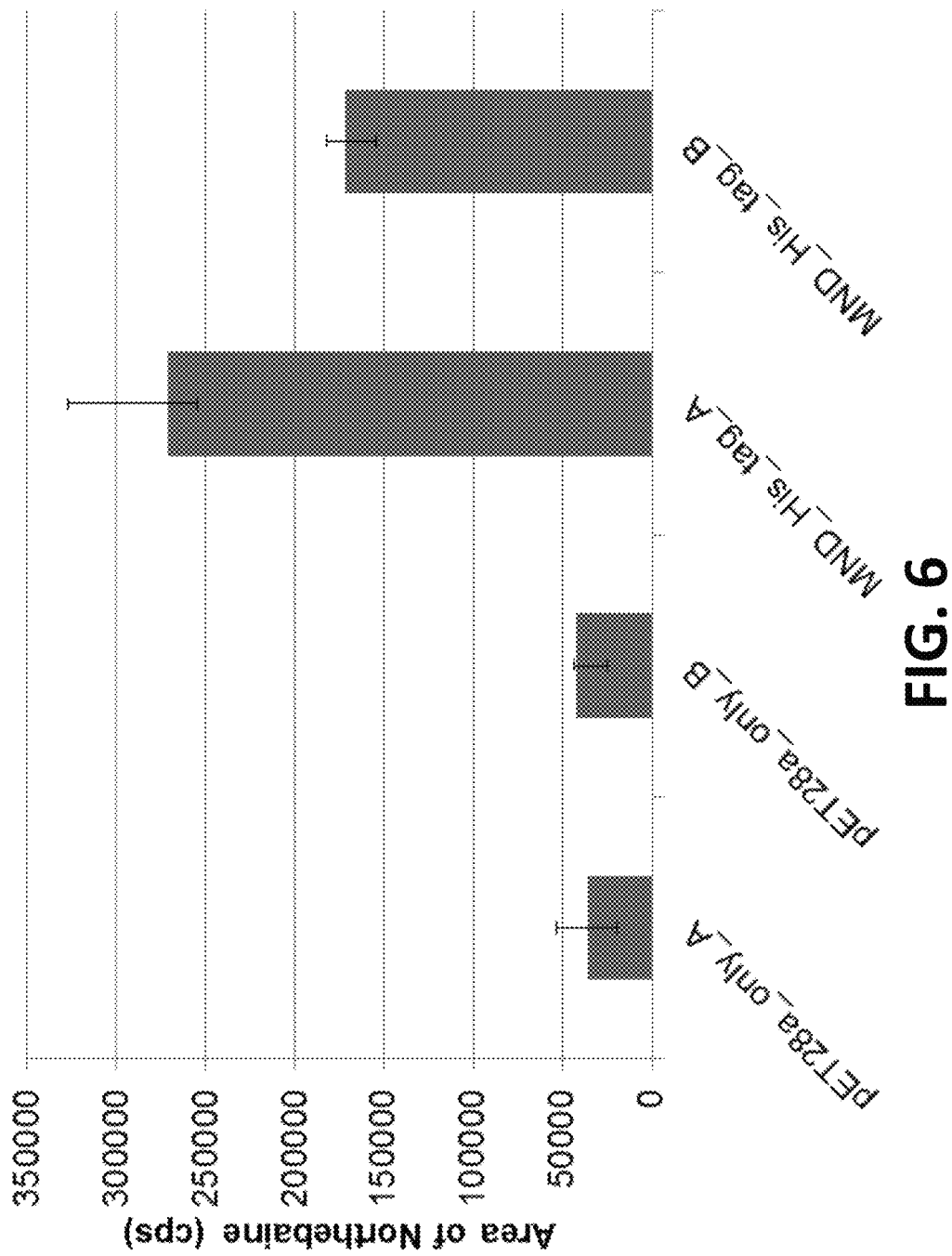
FIG. 6.
Figure 7:
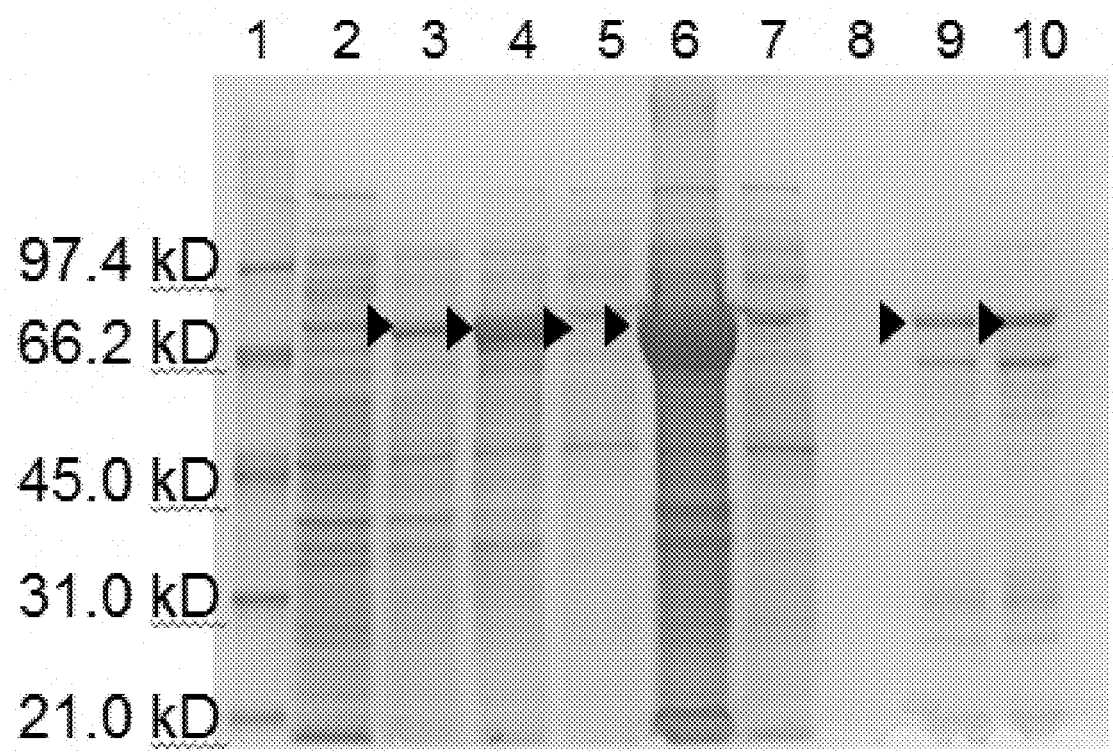
FIG. 7.
Figure 8:
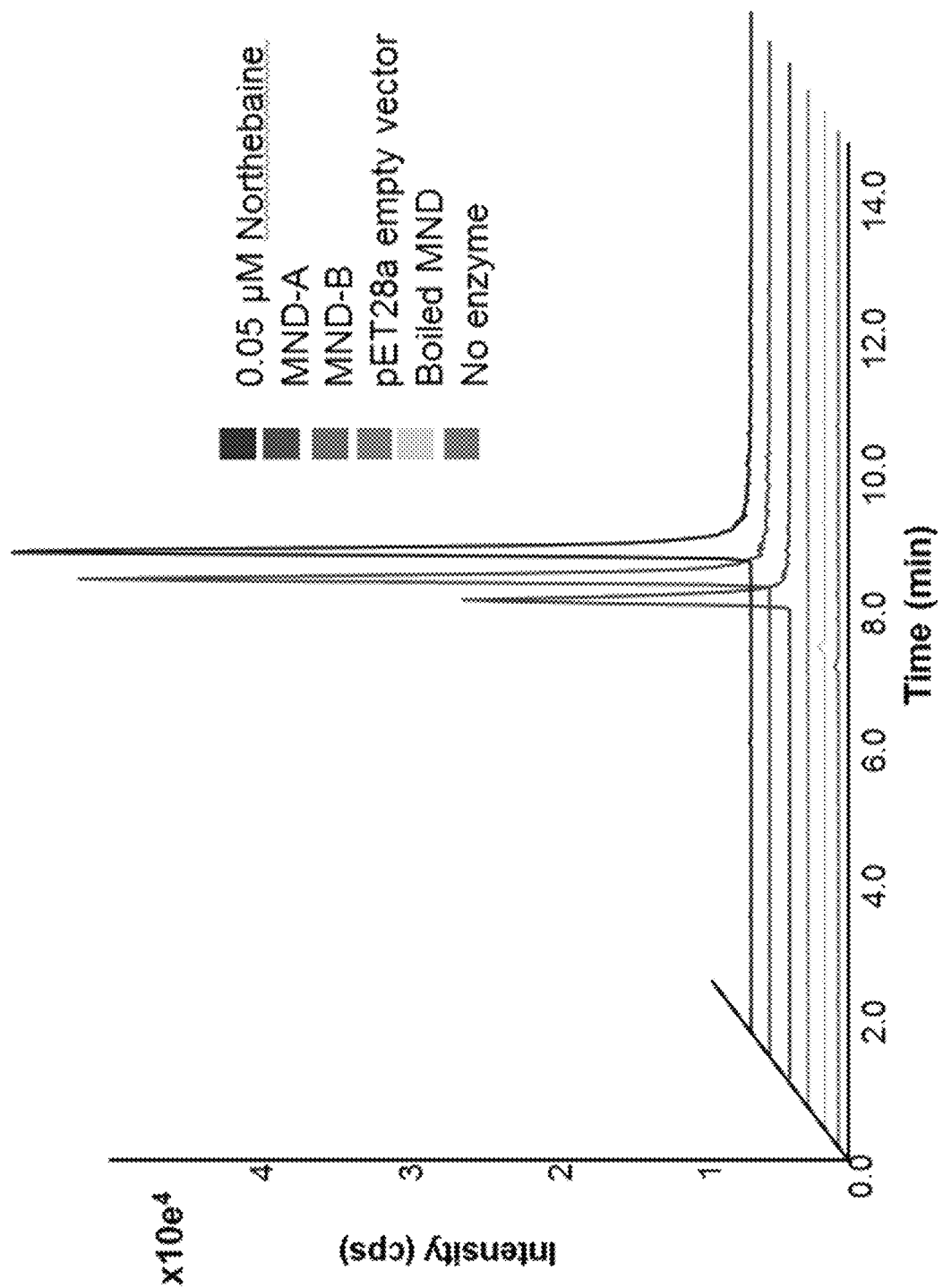
FIG. 8.
Figure 9:
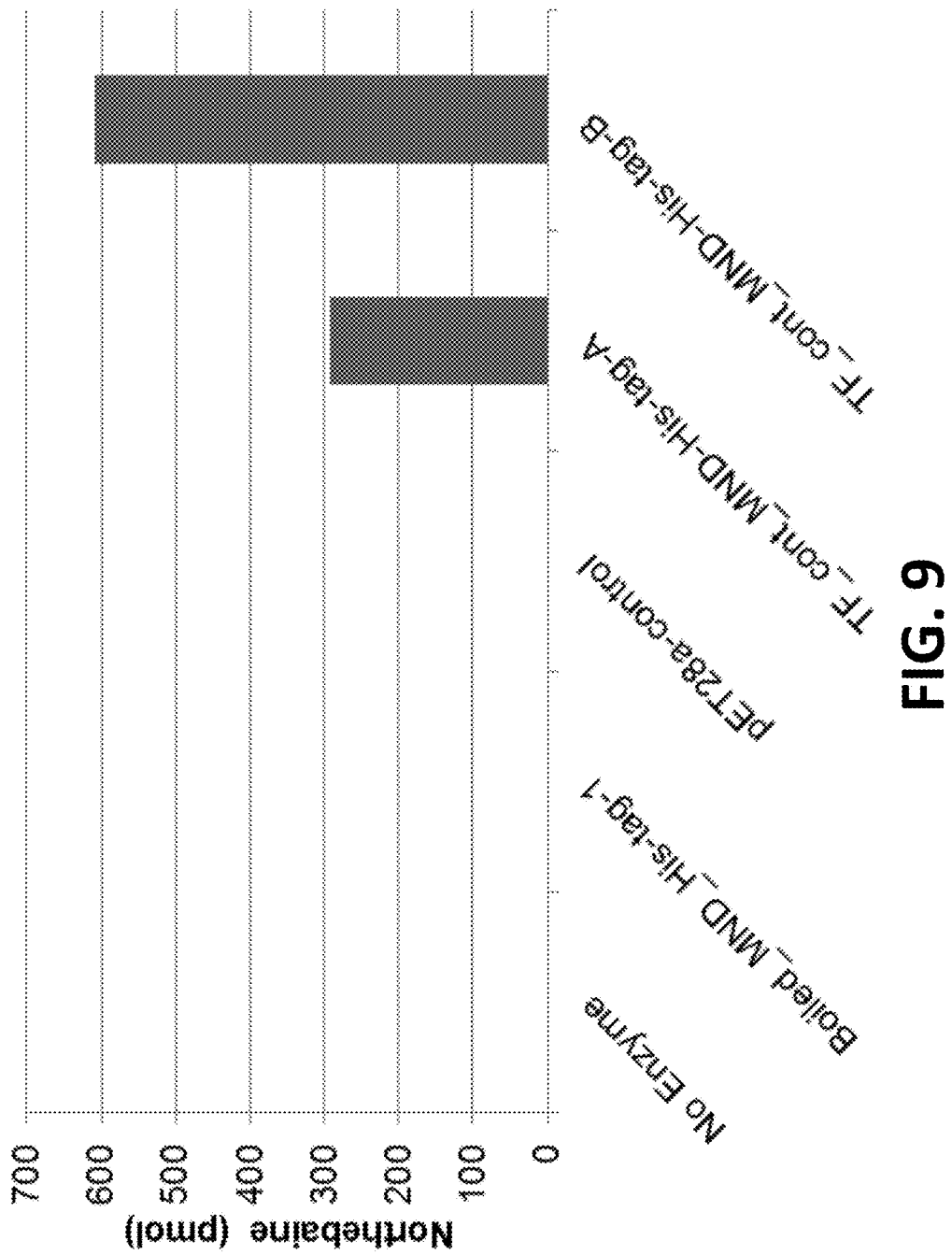
FIG. 9.
Figure 10:
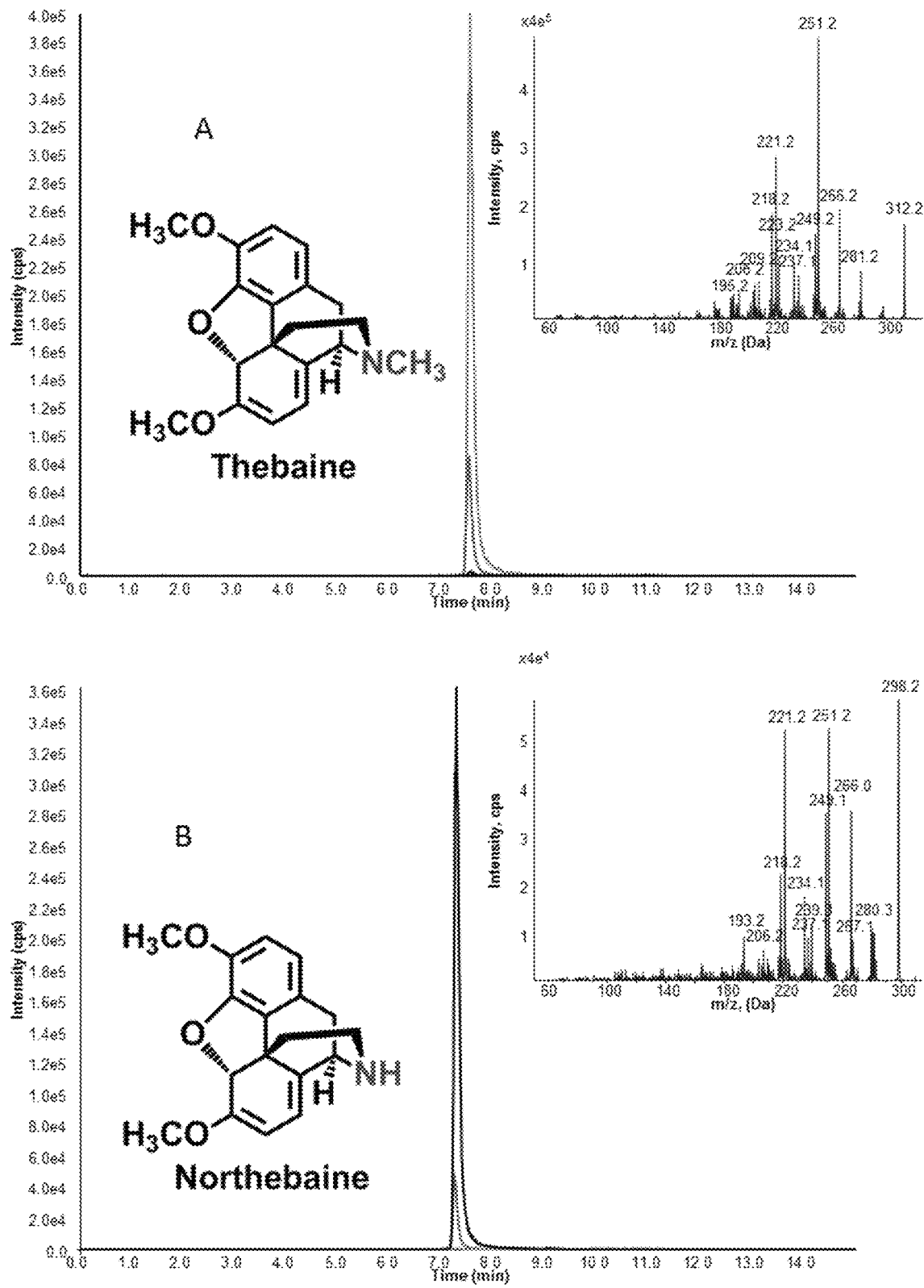
FIG. 10.

The four candidate genes were cloned into the E. coli expression vector pET28a and initially transformed into the expression strain BL21 Star (DE3). For initial enzyme function testing, the genes were expressed and the cells were treated with toluene to permeabilize the membrane and allow for substrate uptake. The toluene was washed away and the cells were resuspended in media supplemented with thebaine and incubated overnight. Half of each culture was extracted and analyzed for northebaine production by LC-MS/MS. Candidate enzyme D showed morphinan N-demethylase activity and was therefore designated morphinan N-demethylase (MND enzyme) (FIG. 5). All other enzymes showed a background accumulation of northebaine similar to the pET28a empty vector control. The experiment was repeated with two individually transformed BL21 Star (DE3) colonies of pET28a and MND enzyme, each performed in triplicate (FIG. 6). Purification of MND enzyme showed a high protein accumulation, but much of that protein was insoluble and remained in the pellet (FIG. 7). Additional verification of protein purification and function was performed by enzyme assay with the purified protein and thebaine as substrate. The assay was performed in duplicate (FIG. 8) with empty vector, boiled enzyme, and no enzyme controls. Only MND enzyme showed any accumulation of northebaine. Quantitation of northebaine production is presented in FIG. 9. Another assay was completed with purified MND enzyme in the same manner, to verify activity (FIG. 10). As presented in FIG. 10, the substrate thebaine was depleted completely in the overnight assay. Chromatograms for both the substrate and product are presented with an inset displaying the fragmentation pattern and structure of each. Both panels contain an overlay of the standard and the negative control.

38.0 Optimized Expression of MND Enzyme Using PLUSE Cells

Figure 11:
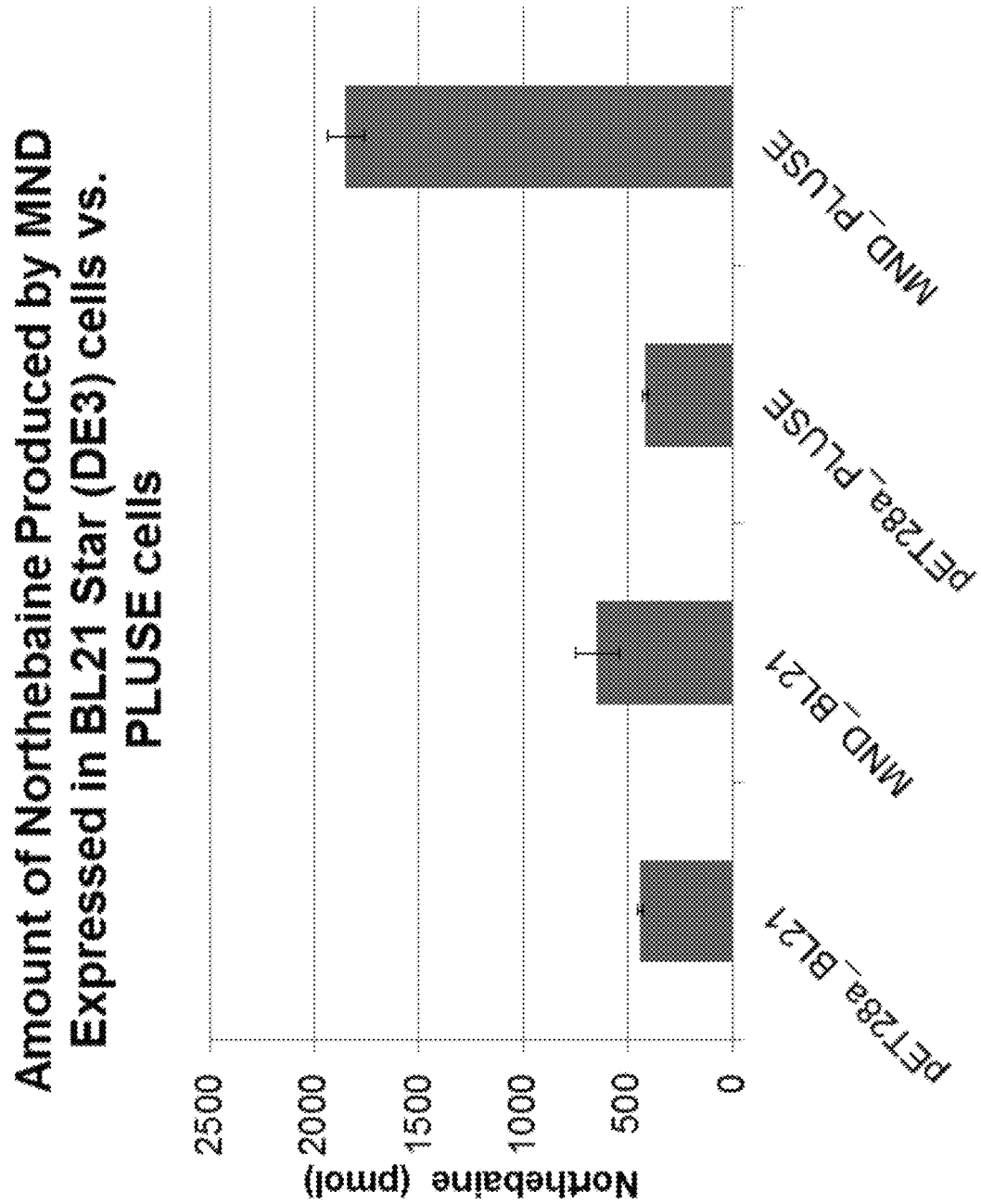
FIG. 11.
Figure 12:
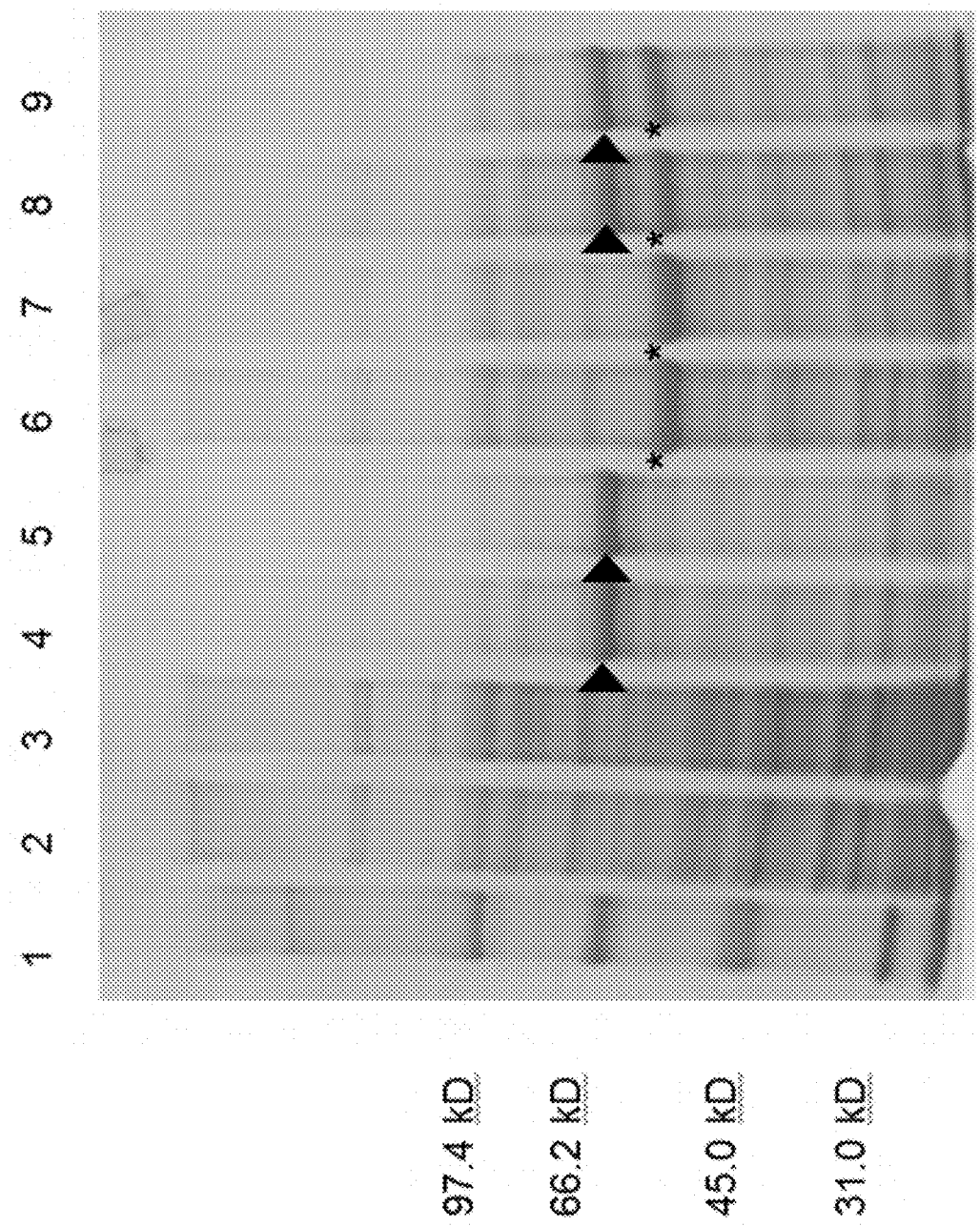
FIG. 12.
Figure 13:
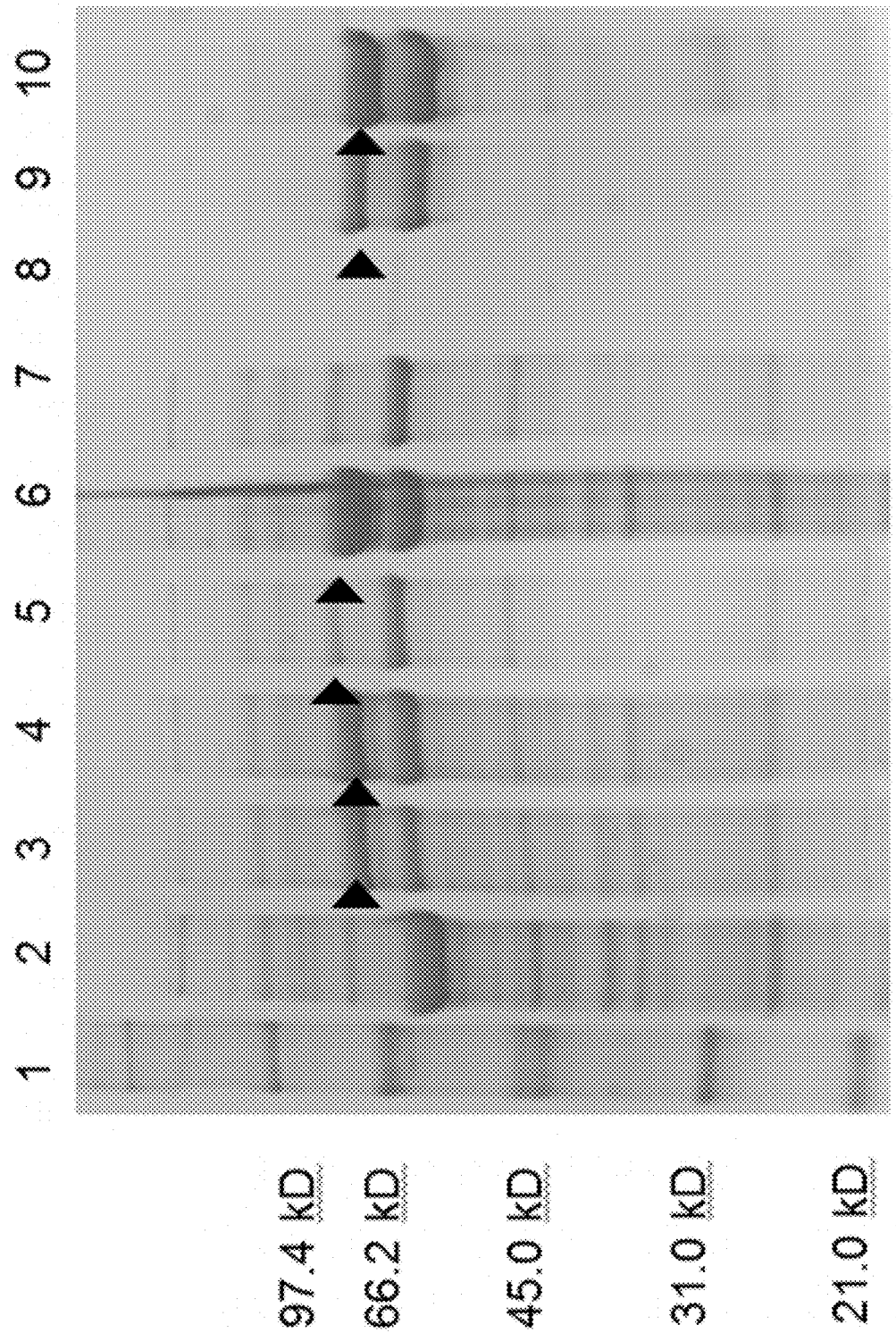
FIG. 13.
Figure 14:
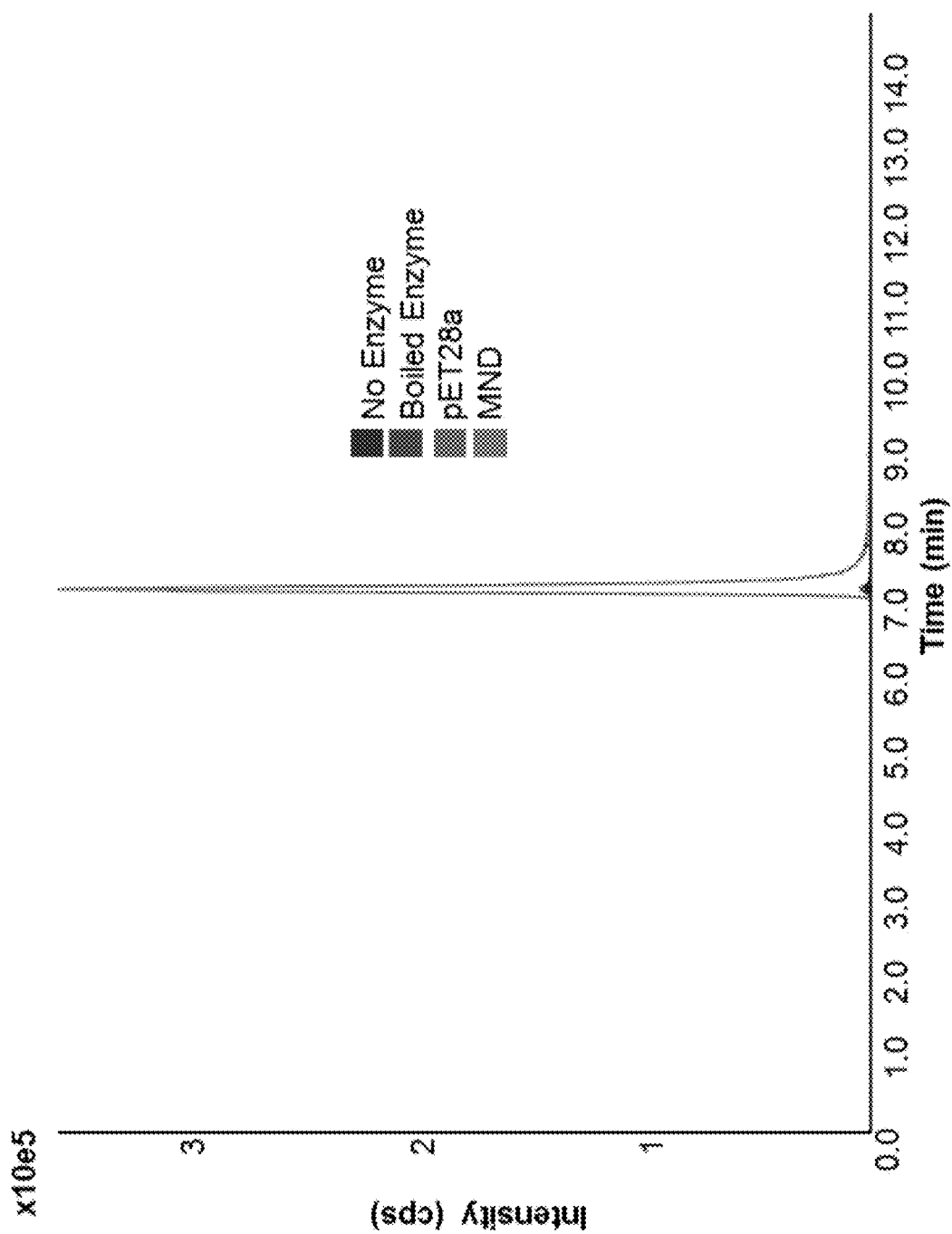
FIG. 14.
Figure 15:
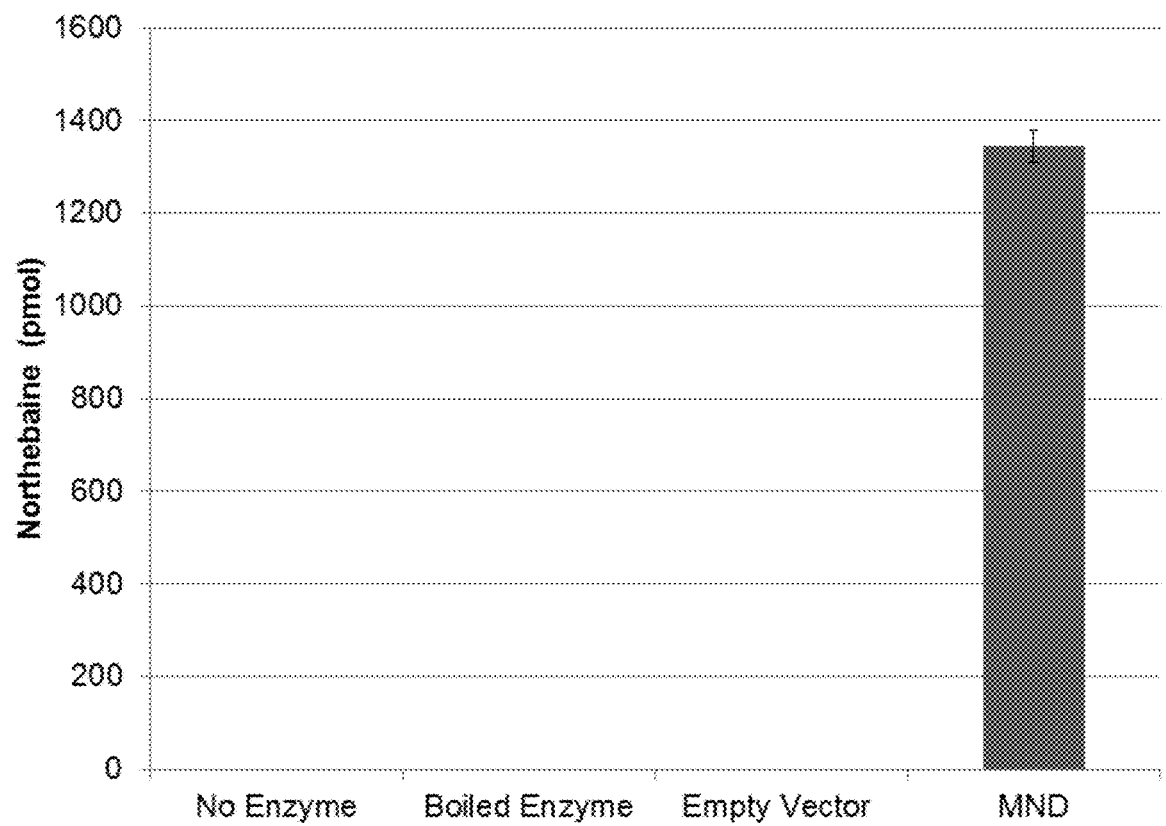
FIG. 15.

Due to the large amount of insoluble protein, several tests were performed to optimize protein production. MND enzyme production occurred pre-induction (FIG. 7, lane 3), so it was hypothesized that the protein was being produced too quickly and mis-folding. Protein production was analyzed under different concentrations of IPTG and different temperatures but the amount of insoluble protein was not improved. The expression vector was then transformed into the PLUSE E. coli expression strain that also express the GroEL and GroES chaperone proteins. The amount of functional protein expressed was significantly increased during the toluene permeabilization assay (FIGS. 11 and 12) when compared to the Bl21 Star (DE3) cells. Therefore, the protein was purified from PLUSE cells for further testing and enzyme characterization (FIG. 13). The purified MND enzyme from PLUSE cells was functionally validated prior to further testing (FIG. 14) and the amount of northebaine produced was quantified (FIG. 15). Essentially all of the substrate was converted to product.

39.0 MND Enzyme Characterization and Substrate Testing

Purified MND enzyme from PLUSE cells was used to test various substrates containing a methylated nitrogen (FIG. 16) in overnight assays. MND enzyme was able to demethylate morphinan compounds tested with high efficiency and was also able to demethylate benzylisoquinoline alkaloids with slightly less efficiency (Table 3). Some of the more surprising substrates accepted by the MND enzyme include galanthamine, scopolamine, hyoscyamine, gramine, (−)-lobeline, physostigmine, isothebaine, and tropinone, indicating that the MND enzyme is promiscuous.

Figure 17:
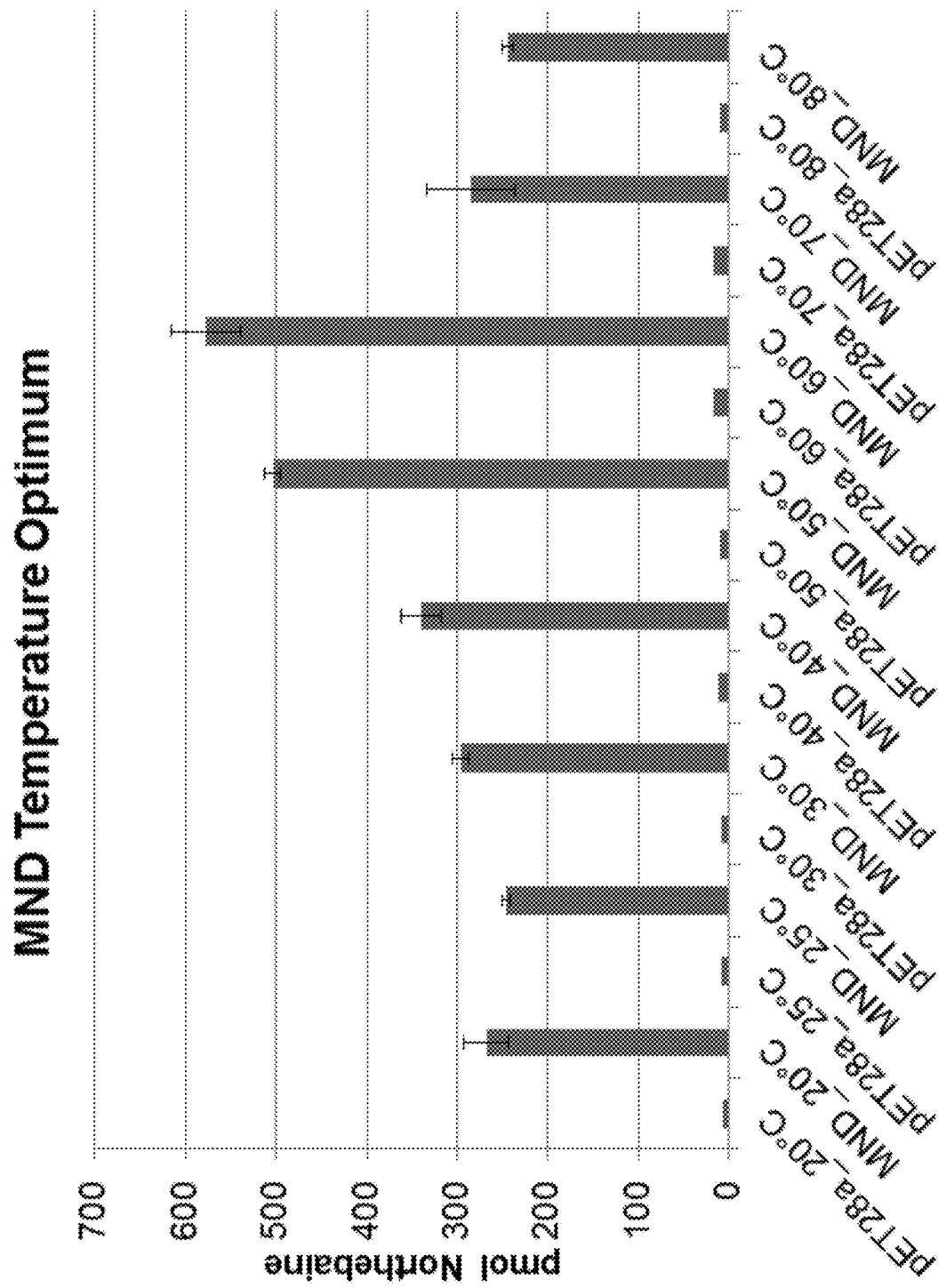
FIG. 17.
Figure 18:
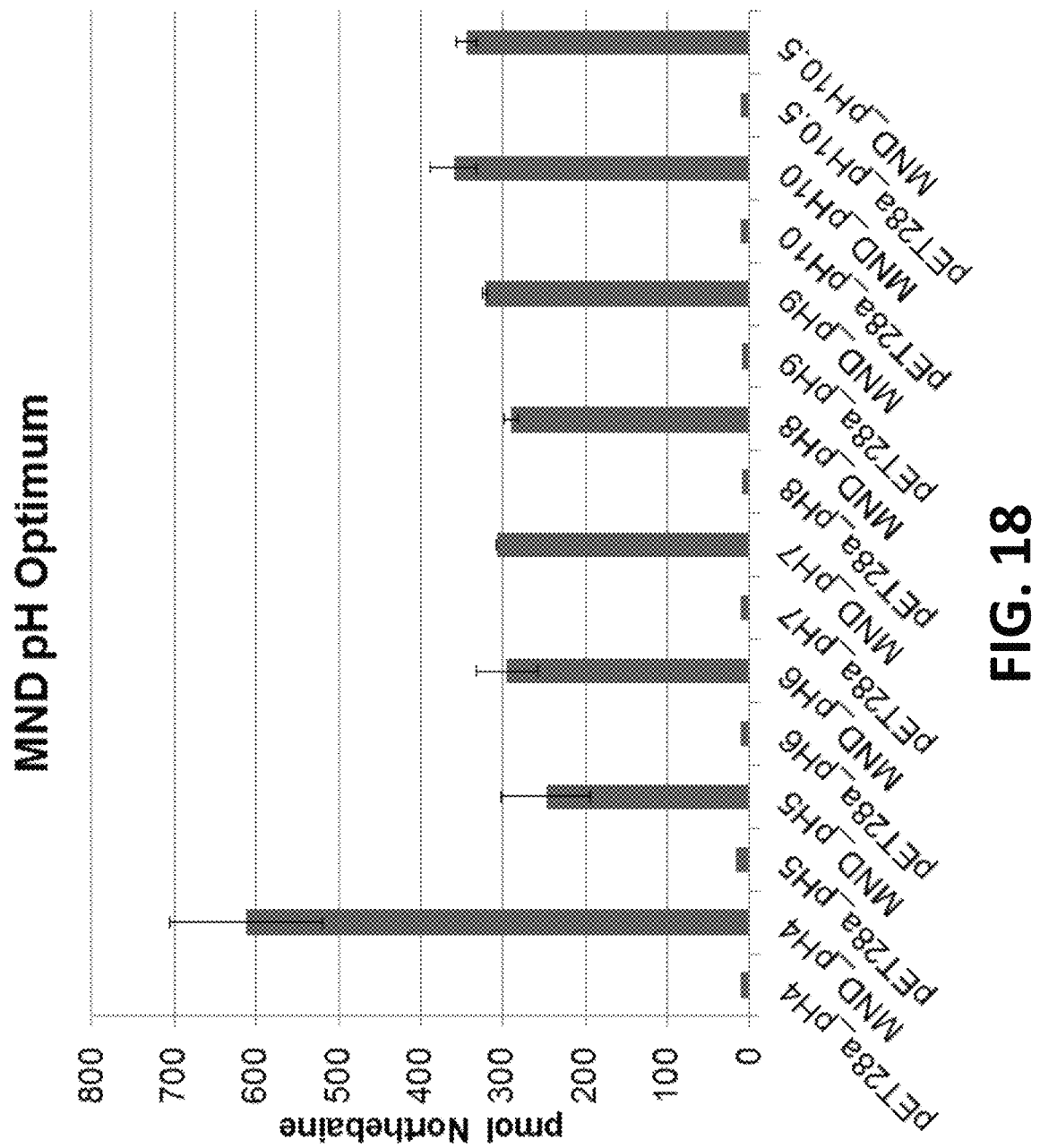
FIG. 18.
Figure 19:
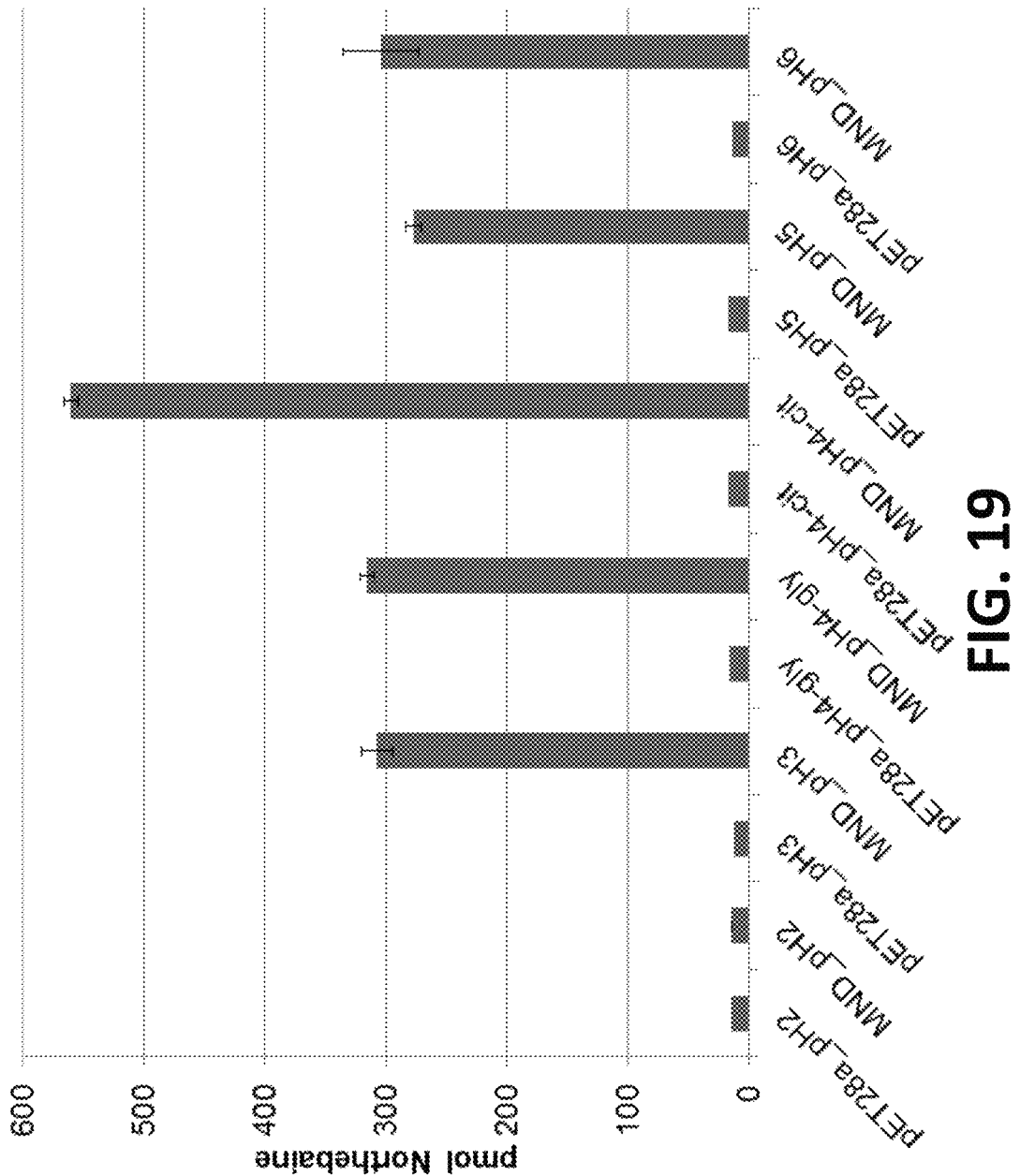
FIG. 19.

The MND enzyme was also able to perform at a wide range of temperatures tested. Assays were allowed to incubate for only 20 min to remain in the linear range of product production. Northebaine was detected at temperatures of 20° C.-80° C., but the highest accumulation was found at 60° C. (FIG. 17). The MND enzyme was also tested in a range of pH solutions including pH 2, 3, 4, 5, 6, 7, 8, 9, 10 and 10.5. There was no significant difference in northebaine production when tested in the pH range of 5-10.5, but pH 4 produced nearly twice as much (FIG. 18). This phenomena was validated with a supplemental assay (performed in duplicate) including pH 4 with two different buffers (FIG. 19), but was only observed in the citrate buffer, not the glycine-HCL buffer.

40.0 MND Enzyme Protein Quantitation

Figure 20:
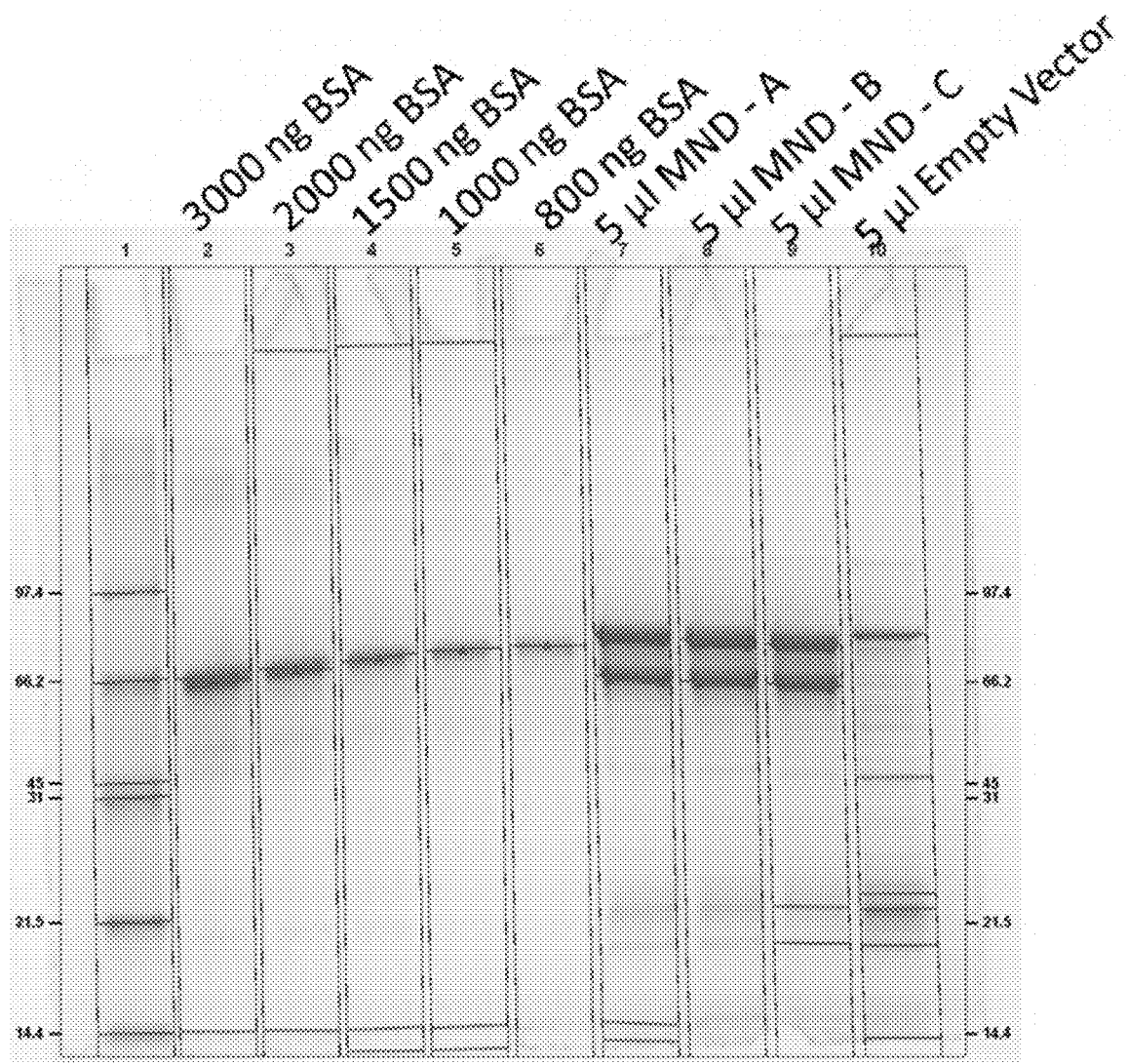
FIG. 20.

The concentration of MND in each protein purification prep was determined by SDS-PAGE using a BSA standard curve. The MND protein purification used for substrate testing and kinetic assays revealed a protein concentration of 360 ng/μl (FIG. 20). The larger band only was used for quantitation as it was shown to be MND by protein sequencing. The average amount of soluble protein was 2 mg/l (in PLUSE cells) and the amount remaining in the inclusion bodies was around 300 mg/l.

41.0 Determination of MND Enzyme Kinetic Values

Figure 21:
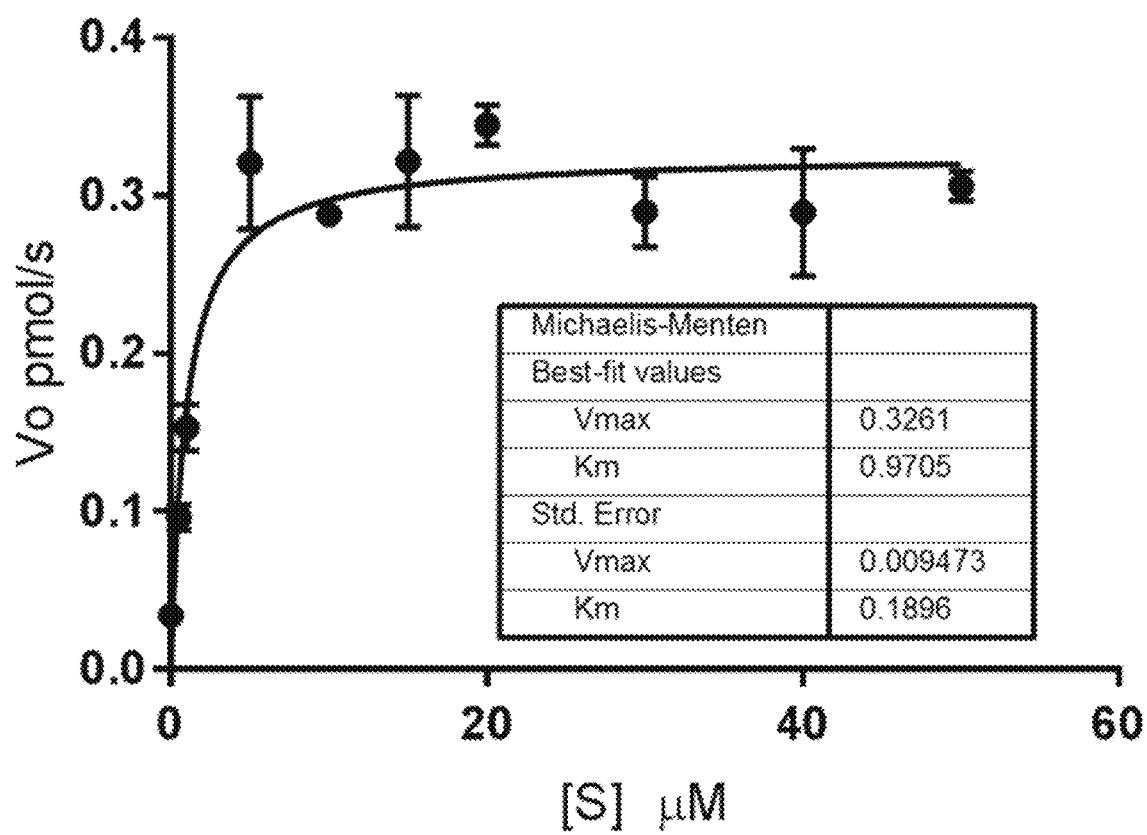
FIG. 21.

MND enzyme assays with increasing substrate concentrations were performed in order to determine kinetic parameters (FIG. 21). MND enzyme was found to have a Vmax of 0.32 pmol s$^{-1}$, $K_m$ of 0.97 μM, and $K_{cat}$ of 6.5×10$^{-4}$ s$^{-1}$.

42.0 MND Enzyme Maintains it Ability to Demethylate after Days of Incubation at 30° C.

Figure 22:
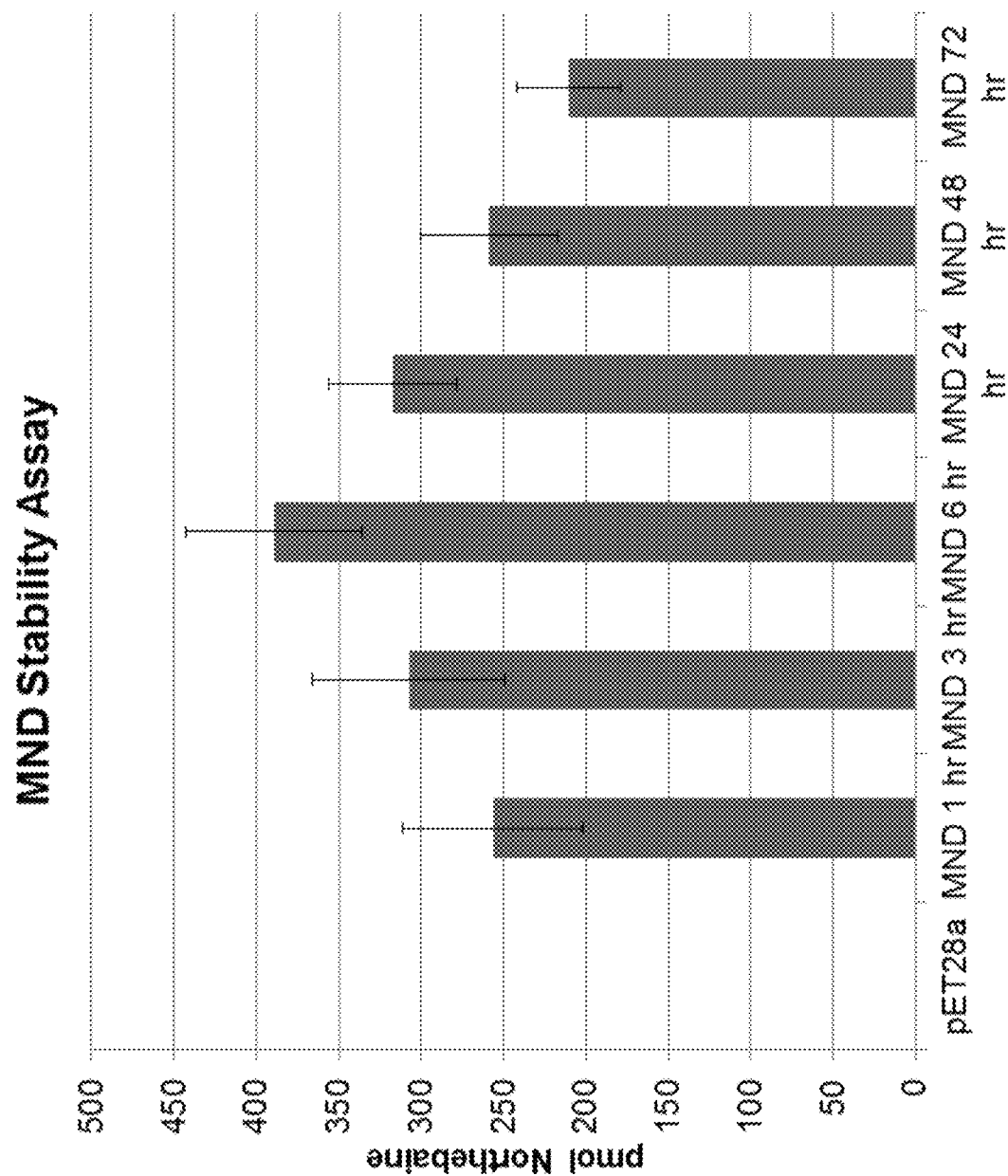
FIG. 22.

MND enzyme was incubated at 30° C. in assay buffer for 1, 3, 6, 24, 48, and 72 hours prior to addition of substrate (thebaine) in order to determine the stability of the MND enzyme (FIG. 22). Upon addition of substrate, assays were allowed to proceed for 20 minutes and product formation was quantitated as above. The MND enzyme maintained its ability to demethylate thebaine after 72 of incubation at 30° C. suggesting the MND enzyme is relatively stable under these conditions.

Figure 23:
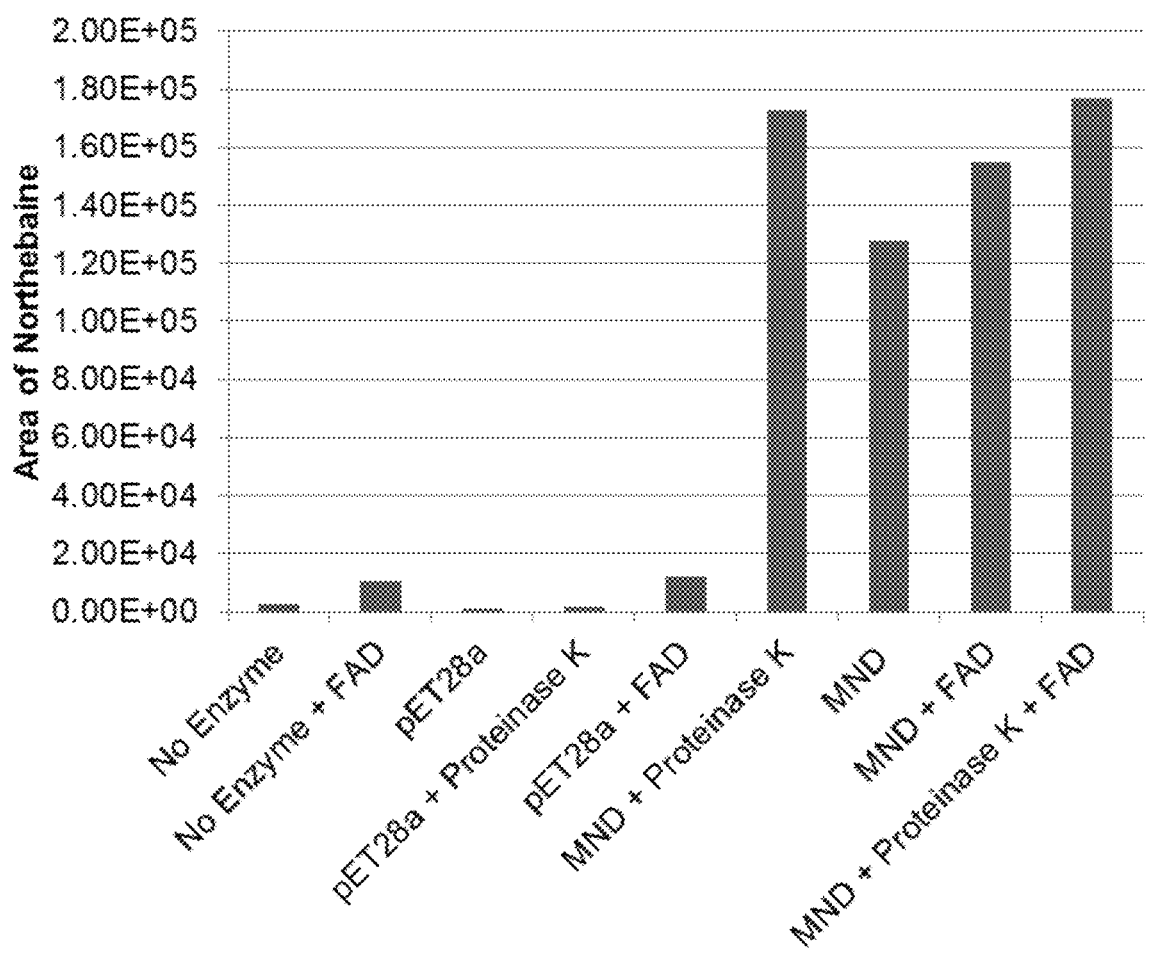
FIG. 23.
Figure 24:
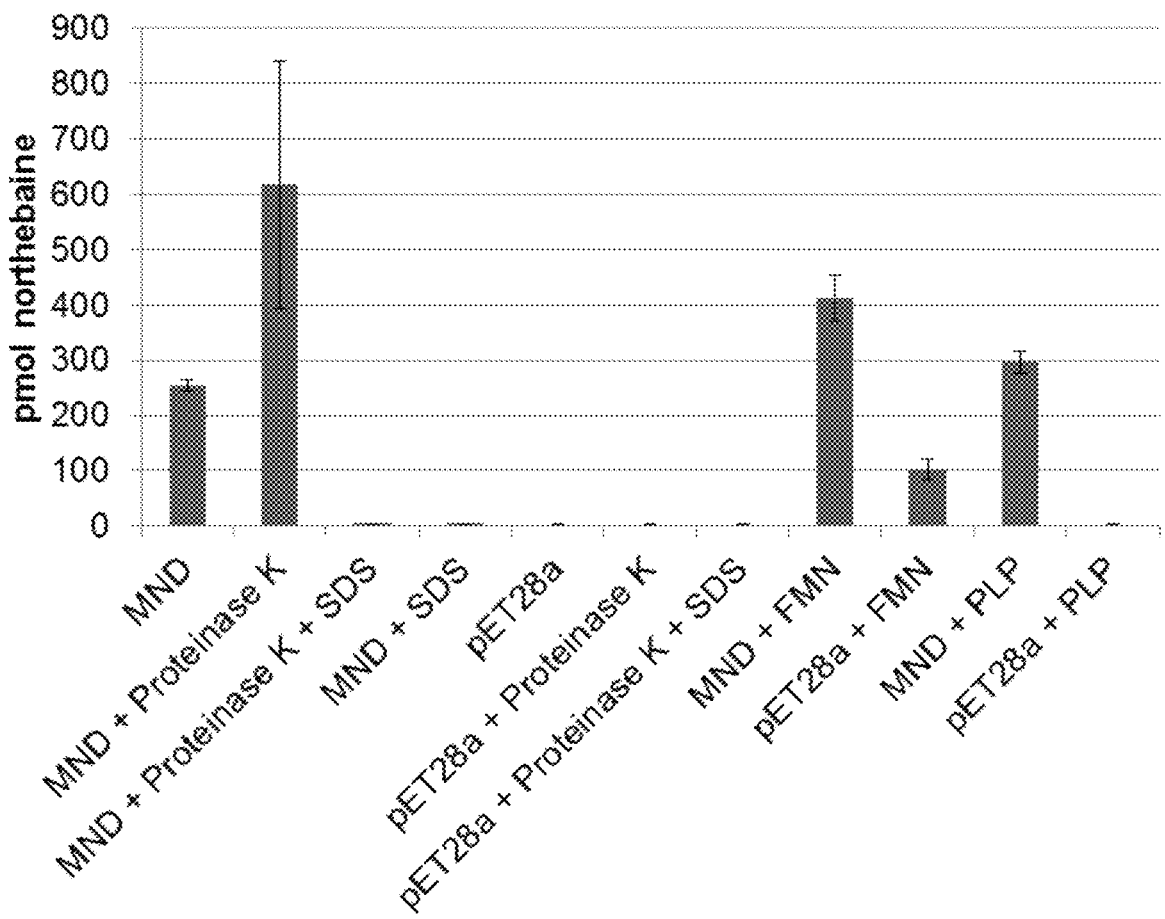
FIG. 24.

43.0 Effects of Cofactor Addition and Proteinase K Digestion on Enzymatic Activity of the MND Enzyme Several assays were performed in order to determine the effect additional cofactors would have on MND enzyme activity. Addition of FAD to no enzyme and pET28a empty vector controls showed a slight increase in the background demethylation of thebaine to northebaine but not close to levels detected in assays containing MND enzyme (FIG. 23). Addition of FMN also showed an increase in background activity, but addition of PLP did not (FIG. 24). MND enzyme was also digested with Proteinase K prior to enzyme assay (FIGS. 23 and 24) in the presence of SDS (increases Proteinase K activity) and additional FAD. Surprisingly the amount of northebaine produced increased after the MND enzyme had been treated with Proteinase K.

44.0 PHYLOGENETIC ANALYSIS OF THE MND ENZYME

The nucleotide sequence and protein sequence of the MND enzyme were subject to BLAST searches using the NCBI NR database and Uniprot. The MND enzyme gene contains 2,013 nucleotides and the resulting protein sequence is 670 amino acids long with an estimated molecular weight of 72 kD. No similar sequences were obtained using the nucleotide BLAST optimized for highly similar sequences. The nucleotide BLAST optimized for more dissimilar sequences resulted in only two hits with very low query coverage (3% and 1%) and high E values (0.005 and 9.2). The top 7 hits resulting from the protein BLAST only shared 39-42% identity with the MND enzyme and were all classified as hypothetical proteins. The subsequent 5 protein BLAST hits annotated as FAD-dependent oxidoreductases. Interestingly, even though the majority of contigs in the Thebainfresser transcriptome annotated as genes from *Methylobacterium* using the NCBI BLAST NR database, not one of the top 100 blast hits using the MND enzyme as query was a *Methylobacterium* gene.

Figure 25:
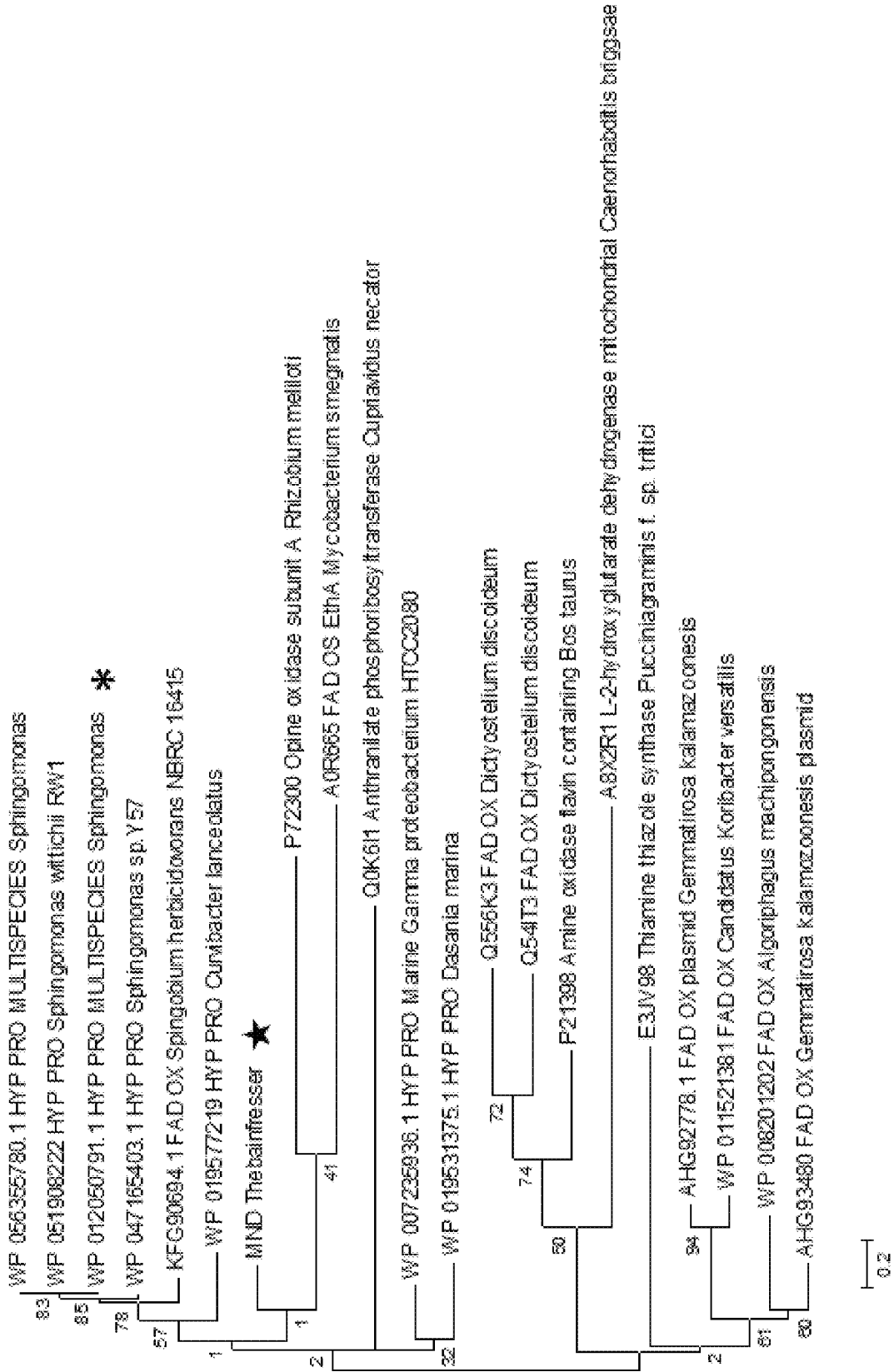
FIG. 25.
Figure 26:
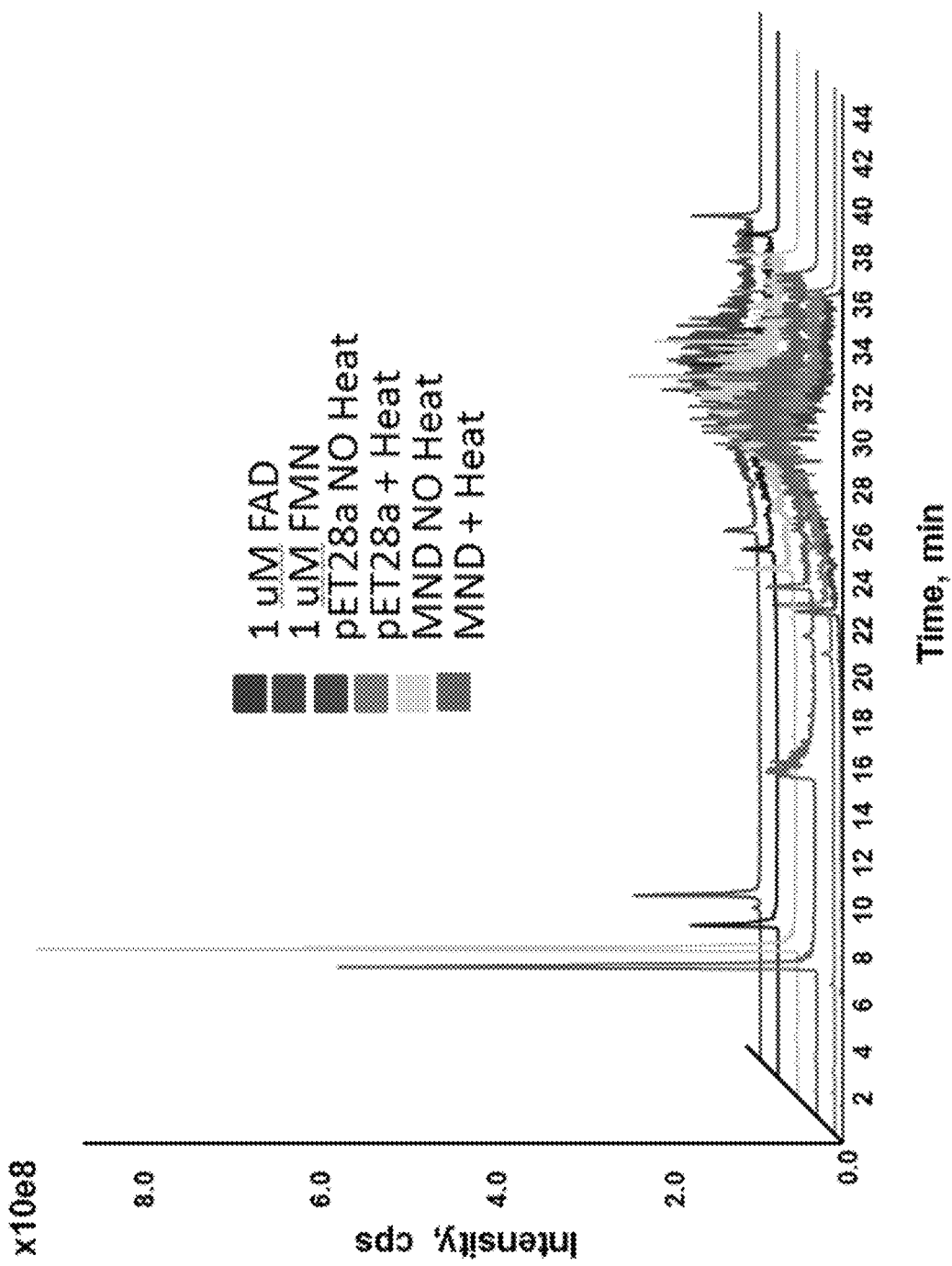
FIG. 26.

The protein sequences of the closest hits obtained by protein BLAST and additional less similar proteins, but with better annotation, were aligned with the Muscle algorithm. A phylogenetic tree was then constructed with the alignment using Mega 6.06 (FIG. 25). The placement of the MND enzyme in the tree indicates no known sequences are closely related. The top protein BLAST hit from the NCBI NR database did not cluster with the MND enzyme and the low bootstrap value clustering the MND enzyme with an opine oxidase subunit from *Rhizobium* and a the ethanolamine utilizing FAD-containing monooxygenase from *Mycobacterium* suggest that its placement in the tree is arbitrary and that it is too dissimilar from all sequences for proper phylogenetic placement, making true annotation difficult.

However, several conserved domains were detected with the protein BLAST. Most notable are a NAD_binding_8 (Rossmann-like) domain spanning amino acids 128-162, a L-aspartate oxidase domain spanning amino acids 121-154, a FAD-dependent oxidoreductase domain spanning amino acids 125-164, a hydroxyglutarate oxidase domain spanning amino acids 124-155, and a deaminating D-amino acid oxidase domain spanning amino acids 121-167. In addition, a thiazole biosynthesis enzyme conserved domain was detected spanning amino acids 125-162 and a phospholipase C domain spanning amino acids 23-67 were also detected. Only one domain was detected when the MND enzyme protein sequence was submitted to Pfam (Finn et al. 2016), and that was also the NAD_binding_8 domain spanning amino acids 128-173. With this in mind, the amino acids from 121-173, spanning the region covered by most conserved domains, was then subject to protein BLAST using both the traditional protein BLAST and the DELTA-BLAST. In addition to one oxidoreductase, the most abundant top BLAST hits were for proteins involved in the twin-arginine translocation pathway. The programs Interpro and Prosite also identified a twin-arginine translocation signal from amino acids 1-53. The motifs uncovered by BLAST and Pfam do suggest binding of nucleotide containing cofactors including FAD, NAD, and NADP, but the lack of homology to known proteins leaves functional identification using sequence alone highly improbable.

45.0 Testing Different *E. coli* Expression Strains

Figure 28:
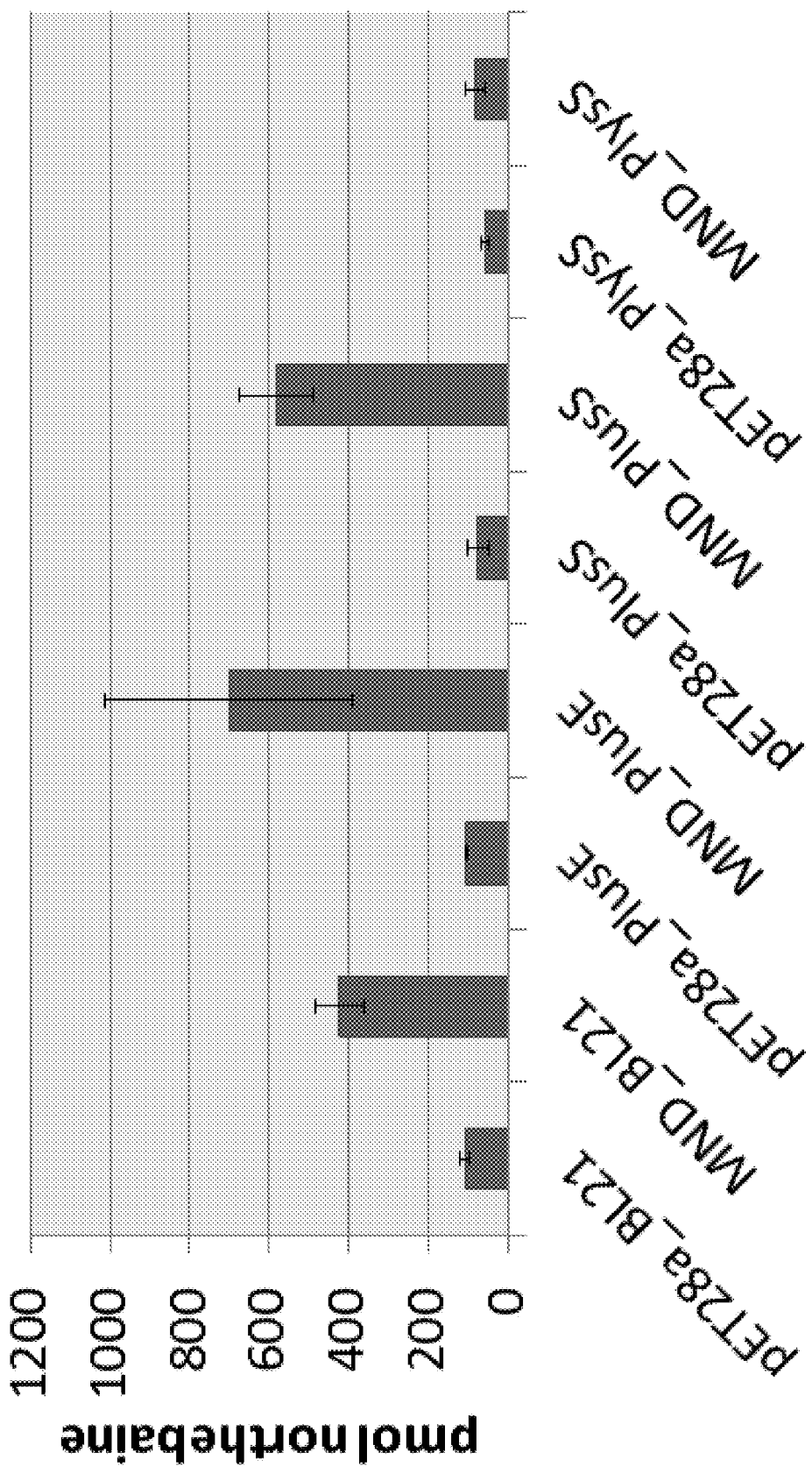
FIG. 28.

Several *E. coli* expression strains were tested in parallel for N-demethylase activity of thebaine by toluene permeabilization assay (FIG. 28). MND in PlusE cells showed the highest activity, with almost 40% more northebaine production than the BL21 Star (DE3) cells, almost 20% more than PluSa cells, and nearly 90% more than pLysS cells. Therefore, this strain was chosen for further experiments.

46.0 Solvent Stability Assays

Figure 27:
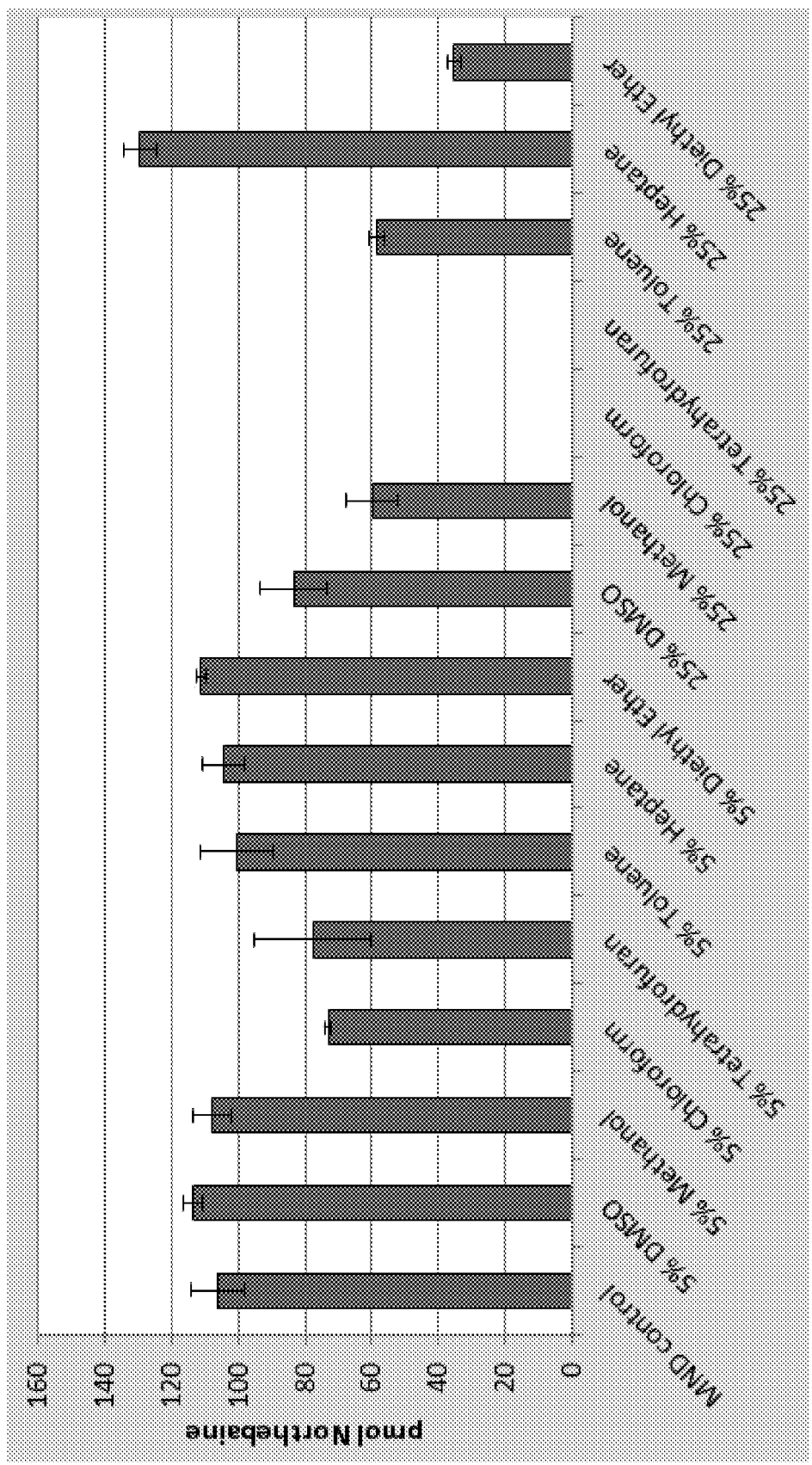
FIG. 27.

Enzymes used in pharma manufacturing must withstand harsh conditions and tolerate solvents, especially if the substrate is insoluble in water (FIG. 27). MND activity was tested in the following solvents at 5% and 25% concentration: DMSO, methanol, chloroform, tetrahydrofuran, toluene, heptane, and diethyl ether. MND showed particular resilience to DMSO, toluene, and methanol with little to no reduction in activity at 5% solvent and only a 21%, 44% and 43% reduction in 25% solvent (respectively). Activity was completely abolished at 25% chloroform and tetrahydrofuran and diethyl ether had a significant reduction of 66%. The heptane reaction was an outlier with no reduction in activity which is most likely due to its insolubility with the enzyme assay components and therefore sat on top of the reaction.

47.0 MND Immobilization to CNBr-Activated SEPHAROSE 4B

Figure 29:
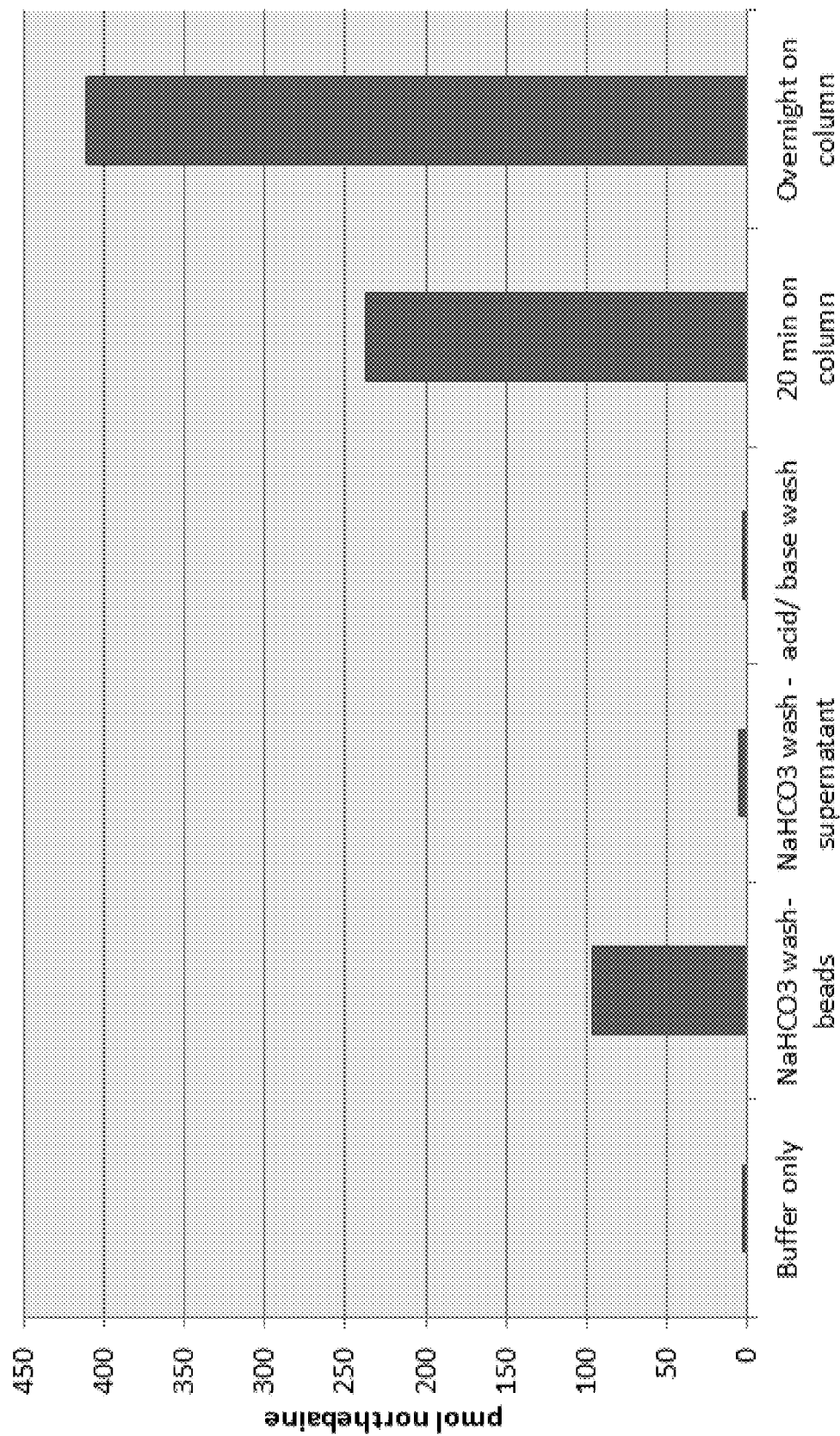
FIG. 29.

MND attached to CNBr-activated Sepharose beads exhibited N-demethylation activity on thebaine. After 20 min on the column, nearly 250 pmol of northebaine was detected while over 400 pmol of northebaine was detected after the overnight incubation (FIG. 29). The only control that showed activity was the sodium carbonate that contained residual sepharose beads, which had MND attached, so this result was expected. An increase in N-demethylase activity could most likely be achieved if substrate was added slowly, allowing the substrate to access more immobilized enzyme.

48.0 Tables

TABLE 1

Thebainfresser Miseq statistics

| | First Run | | | Repeat Run | | |
|---|---|---|---|---|---|---|
| | Reads | length | % GC | Reads | length | % GC |
| Day 0 | 8,257,281 | 35-301 | 49 | 8,970,445 | 35-301 | 49 |
| Day 3 | 12,133,967 | 35-301 | 50 | 10,427,558 | 35-301 | 50 |
| Day 6 | 12,275,725 | 35-301 | 61 | 11,114,298 | 35-301 | 61 |
| UND | 1,047,586 | 35-301 | 51 | 806,073 | 35-301 | 51 |

TABLE 2

Thebainfresser transcriptome statistics through several filtering steps compared to two known Methylobactenum

|  | Methylobacterium extorquens AM1 | Methylobacterium populi BJ001 | Thebainfresser TRINITY RAW | Thebainfresser TRINITY contigs with BLAST Hits only | Thebainfresser TRINITY BLAST hits filtered |
|---|---|---|---|---|---|
| sequences | 6367 | 5546 | 829495 | 18096 | 6792 |
| total length | 5640375 | 5093839 | 217434520 | 12413160 | 9406279 |
| longest | 47493 | 44490 | 50344 | 50344 | 50344 |
| shortest | 30 | 74 | 201 | 201 | 201 |
| mean | 885.88 | 918.47 | 262.13 | 685.96 | 1384.91 |
| N50 | 1167 | 1203 | 250 | 2721 | 4999 |
| GC | 69.35% | 69.90% | 25.92% | 56.40% | 65.23% |
| A | 856936 | 760071 | 84448542 | 2732461 | 1633570 |
| T | 871760 | 773325 | 76632293 | 2679788 | 1637239 |
| G | 1899561 | 1723004 | 31187939 | 3543162 | 3079760 |

TABLE 3

List of compounds used for MND enzyme substrate testing, the masses detected for each, and the percent of substrate demethylated by MND enzyme in an overnight enzyme assay.

| Compound | m/z of Parent ion (substrate) | m/z of Daughter ion (product) | Percent de-methylated |
|---|---|---|---|
| Oripavine | 298 | 284 | 100% |
| (R)-Reticuline | 330 | 316 | 25% |
| Salutaridine | 328 | 314 | 100% |
| Salutaridinol | 330 | 316 | 100% |
| Heroin | 370 | 356 | 70% |
| Thebaine | 312 | 298 | 100% |
| Morphinone | 284 | 270 | 100% |
| Codeinone | 298 | 284 | 100% |
| Codeine | 300 | 286 | 100% |
| Morphine | 286 | 272 | 100% |
| Hydromorphone | 286 | 272 | 98% |
| Oxymorphone | 302 | 288 | 73% |
| Galanthamine | 288 | 274 | 27% |
| Laudanine (Laudanidine) | 344 | 330 | 14% |
| Orientaline | 330 | 316 | 100% |
| Protosinomenine | 330 | 316 | 60% |
| Isoorientaline | 330 | 316 | 86% |
| Laudanosine | 358 | 344 | 31% |
| (S)-Reticuline | 330 | 316 | 55% |
| Scopolamine | 304 | 290 | 65% |
| Hyoscyamine | 290 | 276 | 18% |
| Noscapine (Narcotine) | 414 | 400 | 20% |
| Tropinone | 140 | 126 | 40% |
| Physostigmine | 276 | 262 | 37% |
| Isothebaine | 312 | 298 | 35% |
| (−)-Lobeline | 338 | 324 | 20% |
| Gramine | 175 | 161 | 51% |
| Autumnaline | 374 | 360 | 11% |

49.0 Thebainfresser Growth Media

TABLE 4

Minimal media (MODLS + THEBAINE)

| macronutrients | mg/L | 10 X stock solutions |
|---|---|---|
| KNO$_3$ | 250 | 2.5 g |
| MgSO$_4$ × 7H$_2$O | 250 | 2.5 g |
| KH$_2$PO$_4$ | 250 | 2.5 g |
| Ca(NO$_3$)$_2$*4H$_2$O | 1000 | 10.0 g |

TABLE 4-continued

Minimal media (MODLS + THEBAINE)

| micronutrients | mg/L | 1000X, 100 ml total volume |
|---|---|---|
| MnSO$_4$ × H$_2$O | 10 | 1000 mg |
| ZnSO$_4$ × 7H$_2$O | 2 | 200 mg |
| Na$_2$MoO$_4$ × 2H$_2$O | 0.25 | 25 mg |
| CuSO$_4$ × 5H$_2$0 | 0.025 | 2.5 mg |
| CoCl$_2$ × 6H$_2$O | 0.025 | 2.5 mg |
| NiCl$_2$*6H$_2$O | 0.03 | 3.0 mg |
| KI | 0.75 | 75 mg |
| H$_3$BO$_3$ | 3 | 300 mg |

↓

Adjust pH to 5.0
Autoclave 20 min, 121° C.
Add 373 mg thebaine per L after cooling to RT

REFERENCES

Augustin, J. M., Higashi, Y., Feng, X. and Kutchan, T. M. (2015) Production of mono- and sesquiterpenes in Camelina sativa oilseed. Planta, 242, 693-708.

Bolger, A. M., Lohse, M. and Usadel, B. (2014) Trimmomatic: a flexible trimmer for Illumina sequence data. Bioinformatics, 30, 2114-2120.

Burriesci, M. S., Lehnert, E. M. and Pringle, J. R. (2012) Fulcrum: condensing redundant reads from high-throughput sequencing studies. Bioinformatics, 28, 1324-1327.

Camacho, C., Coulouris, G., Avagyan, V., Ma, N., Papadopoulos, J., Bealer, K. and Madden, T. L. (2009) BLAST+: architecture and applications. BMC bioinformatics, 10, 421.

Finn, R. D., Coggill, P., Eberhardt, R. Y., Eddy, S. R., Mistry, J., Mitchell, A. L., Potter, S. C., Punta, M., Qureshi, M., Sangrador-Vegas, A., Salazar, G. A., Tate, J. and Bateman, A. (2016) The Pfam protein families database: towards a more sustainable future. Nucleic acids research, 44, D279-285.

Grabherr, M. G., Haas, B. J., Yassour, M., Levin, J. Z., Thompson, D. A., Amit, I., Adiconis, X., Fan, L., Raychowdhury, R., Zeng, Q., Chen, Z., Mauceli, E., Hacohen, N., Gnirke, A., Rhind, N., di Palma, F., Birren, B. W., Nusbaum, C., Lindblad-Toh, K., Friedman, N. and Regev, A. (2011) Full-length transcriptome assembly from RNA-Seq data without a reference genome. Nature biotechnology, 29, 644-652.

Li, H. and Durbin, R. (2009) Fast and accurate short read alignment with Burrows-Wheeler transform. Bioinformatics, 25, 1754-1760.

Lu, C. and Kang, J. (2008) Generation of transgenic plants of a potential oilseed crop *Camelina sativa* by *Agrobacterium*-mediated transformation. Plant cell reports, 27, 273-278.

Mockler, T. C., Michael, T. P., Priest, H. D., Shen, R., Sullivan, C. M., Givan, S. A., McEntee, C., Kay, S. A. and Chory, J. (2007) The DIURNAL project: DIURNAL and circadian expression profiling, model-based pattern matching, and promoter analysis. Cold Spring Harb Symp Quant Biol, 72, 353-363.

Paoni, N. F. and Koshland, D. E., Jr. (1979) Permeabilization of cells for studies on the biochemistry of bacterial chemotaxis. Proceedings of the National Academy of Sciences of the United States of America, 76, 3693-3697.

Tamura, K., Stecher, G., Peterson, D., Filipski, A. and Kumar, S. (2013) MEGA6: Molecular Evolutionary Genetics Analysis version 6.0. Molecular biology and evolution, 30, 2725-2729.

Tartoff, K. D. and Hobbs, C. A. (1987) Improved Media for Growing Plasmid and Cosmid Clones. Bethesda Res. Lab. Focus, 9.

William, S. and Copeland, H. F. (2012) Bacterial genomic DNA isolation using CTAB. World Wide Web at jgidoe-gov/collaborate-with-ghi/pmo-overview/protocols-sample-preparatioN-information.

What is claimed is:

1. A method of N-demethylating a low molecular weight N-methylated compound, the method comprising incubating the low molecular weight N-methylated compound with an isolated, purified, or isolated and purified morphinan N-demethylase (MND) enzyme, or a fragment thereof having N-demethylase activity, wherein the MND enzyme comprises an amino acid sequence that has at least 85% sequence identity with the amino acid sequence of SEQ ID NO: 2, thereby converting the low molecular weight N-methylated compound into an N-demethylated compound.

2. The method of claim 1, wherein flavin adenine dinucleotide (FAD) is added as a cofactor to the MND enzyme or fragment thereof prior to and/or during incubation with the low molecular weight N-methylated compound.

3. The method of claim 1, wherein the MND enzyme or fragment thereof comprises one or more of benzylisoquinoline alkaloid N-demethylase activity, tropane alkaloid N-demethylase activity, pyrroloindole alkaloid N-demethylase activity, piperidine alkaloid N-demethylase activity, aporphine alkaloid N-demethylase activity, indole alkaloid N-demethylase activity, or Amaryllidaceae alkaloid N-demethylase activity.

4. The method of claim 1, wherein the N-methylated compound is selected from the group consisting of thebaine, oripavine, (R)-reticuline, salutaridine, salutaridinol, heroin, morphinone, codeinone, codeine, morphine, hydromorphone, oxymorphone, galanthamine, laudanine, orientaline, protosinomenine, isoorientaline, laudanosine, (S)-reticuline, scopolamine, hyoscyamine, noscapine, gramine, (–)-lobeline, physostigmine, isothebaine, (R,S)-autumnaline, and tropinone.

5. The method of claim 1, wherein the MND enzyme or fragment thereof is immobilized.

6. The method of claim 1, wherein the low molecular weight N-methylated compound is incubated with the MND enzyme or fragment thereof at a pH of about 4.0 in a citrate buffer.

7. The method of claim 1, wherein the N-demethylated compound is further modified by the chemical or enzymatic addition of a functional moiety to the demethylated nitrogen.

8. A method of producing an active N-substituted compound or precursor thereof, the method comprising
(i) N-demethylating a low molecular weight N-methylated compound by incubating the low molecular weight N-methylated compound with an isolated, purified, or isolated and purified morphinan N-demethylase (MND) enzyme, or a fragment thereof having N-demethylase activity,
wherein the MND enzyme comprises an amino acid sequence that has at least 85% sequence identity with the amino acid sequence of SEQ ID NO: 2,
thereby converting the low molecular weight N-methylated compound into an N-demethylated compound, and
(ii) using the N-demethylated compound produced in (i) as a precursor to produce the active N-substituted compound or precursor thereof.

9. The method of claim 8, wherein the active N-substituted compound or precursor thereof is produced by the chemical or enzymatic addition of a functional moiety to the demethylated nitrogen of the N-demethylated compound.

10. The method of claim 8, wherein the method further comprises screening the activity of the active N-substituted compound for drug discovery.

11. The method of claim 8, wherein the active N-substituted compound is a pharmaceutical compound.

12. The method of claim 8, wherein the active N-substituted compound is a synthetic or semisynthetic opiate selected from the group consisting of oxycodone, oxymorphine, nalbuphine, naltrexone, buprenorphine, naloxone, and nalmefene, or is selected from the group consisting of tropane alkaloids, benzylisoquinoline alkaloids, pyrroloindole alkaloids, piperidine alkaloids, aporphine alkaloids, Amaryllidaceae alkaloids, noratropine, oxitropium, and ipratropium bromide.

13. The method of claim 9, wherein the functional moiety added to the demethylated nitrogen is:
(i) selected from the group consisting of a methyl group, an allyle group, an isopropyl group, an ethyl group, a propene group, a cyclopropylmethyl group, and a cyclobutylmethyl group, or
(ii) selected from the group consisting of a combination of a methyl group and an isopropyl group, a combination of a methyl group and an ethyl group, a combination of a methyl group and a propene group, a combination of a methyl group and a cyclopropylmethyl group, and a combination of a methyl group and a cyclobutylmethyl group.

14. The method of claim 7, wherein the functional moiety added to the demethylated nitrogen is:
(i) selected from the group consisting of a methyl group, an allyle group, an isopropyl group, an ethyl group, a propene group, a cyclopropylmethyl group, and a cyclobutylmethyl group, or
(ii) selected from the group consisting of a combination of a methyl group and an isopropyl group, a combination of a methyl group and an ethyl group, a combination of a methyl group and a propene group, a combination of a methyl group and a cyclopropylmethyl group, and a combination of a methyl group and a cyclobutylmethyl group.

15. The method of claim 1, wherein the N-methylated compound is selected from the group consisting of thebaine, oripavine, (R)-reticuline, salutaridine, salutaridinol, heroin, morphinone, codeinone, codeine, morphine, hydromorphone, oxymorphone, galanthamine, laudanine, orientaline, protosinomenine, isoorientaline, laudanosine, (S)-reticuline, scopolamine, hyoscyamine, noscapine, gramine, (–)-lobeline, physostigmine, isothebaine, and tropinone.

16. The method of claim 7, wherein the functional moiety added to the demethylated nitrogen is:
(i) selected from the group consisting of a methyl group, an isopropyl group, an ethyl group, a propene group, a cyclopropylmethyl group, and a cyclobutylmethyl group, or
(ii) selected from the group consisting of a combination of a methyl group and an isopropyl group, a combination of a methyl group and an ethyl group, a combination of a methyl group and a propene group, a combination of a methyl group and a cyclopropylmethyl group, and a combination of a methyl group and a cyclobutylmethyl group.

17. The method of claim 9, wherein the functional moiety added to the demethylated nitrogen is:
(i) selected from the group consisting of a methyl group, an isopropyl group, an ethyl group, a propene group, a cyclopropylmethyl group, and a cyclobutylmethyl group, or
(ii) selected from the group consisting of a combination of a methyl group and an isopropyl group, a combination of a methyl group and an ethyl group, a combination of a methyl group and a propene group, a combination of a methyl group and a cyclopropylmethyl group, and a combination of a methyl group and a cyclobutylmethyl group.

* * * * *

SEQUENCE LISTING

<160> NUMBER OF SEQ ID NOS: 9

<210> SEQ ID NO 1
<211> LENGTH: 2013
<212> TYPE: DNA
<213> ORGANISM: Methylobacterium Thebainfresser

<400> SEQUENCE: 1

```
atgactgaaa aaacgcctaa actaggctct gaagccgcaa ataaactcgg attagaagct      60
gacatttctc ggcgcgacat ggtgggcggc gtattgatcg gagcaggggc agctctgctc     120
gcatccgttg cgccaggggc gattaataga gcgttggccg aggggccgag caggctaccg     180
ccggtgcgtg gttccggtac cggttggcga ggaatagaga tcgccgatga ctggcaaggc     240
ccaggcggca tcggggatta ctctaagtca aacggcaaca cgggcaaagt tatccgtgac     300
gcgcatgcag gcattcggaa ccacgagttc gagaagcggc ttgctacggc gagtgacgtc     360
aacgagaaat atgatgttat tattgtaggc gcgggcattt cggggcttca cagcgcctac     420
gatcttcttc gccagcggcc aaatataaag atcctaatgc ttgacaacca tgccatcttc     480
ggtggggagg caaagcaaaa taagatggag gtagacggtc aggcgctgta tggcggccag     540
ggcccaacgc tttactcctt cgttggtgat gacctcccga gctggaaagg taatccggcc     600
ctcgcatcta tcatggaact caaaacatat cccaaggagt tcggacttcc gaccgaaact     660
acatggagcg ataagaagac ggacgtaaag gtgccggtcg acctttggtt ctccatggcc     720 agccccctcgc agaccgacat cgcctatcgg tgggagggaa gtgggttggt gaagaatcct     780
ttgctgaact cctttcgtga tgccccagtg tcgcagaaaa gcaaagatgc cattgccctt     840
atgctcgctg tcgacaacgg cgcgaagagg cctgttgaac cagtgggcga tgtatcgacc     900
tgggtcgaca atatgaccta tgcggagttt ctgaagaagg tatatggtgc ggacgacgaa     960
gctgttcagc ttgtcgacca gattgatgtc gttggaacag cggggcttgg cggtgatgtt    1020
tttaatgcaa gccttgcagc actcggacta aatcaatacg ggggcatcga gctctggaac    1080
ggcggtttgc aagggttgag tcttccgacc ggaaatggcg gcgtggggcg gtccatcctt    1140
cgcaagttca tgccaggagc tatcaagggc gggacatcgc tcaccgacac gcttttcggt    1200
gacgtgaact gggacgtgct tgaccacgct aacaacaacg ttcgaatccg gctcaattca    1260
actgtcgtag gtgttcagaa taatgagacg ccgactggca caaagatgc gaccgttttc    1320 ttccttcacg ataatcgcct ttacaaggcc aaagggaagg cggtgatcat gggtacaccg    1380
cagcaggtca atcgtaatgt ttgcctcaat ttgccaaacc atcttagcga ggcaatgggc    1440
gatttccatc atgctccgat cctggttgtg aatgtggccc tccggaactg gaaatcgatg    1500
```

```
gaaaaggctg gcgtttccgg cttgcggtgg ttcggagaat atccgggtat cggtcagata      1560
gttcgatcga tggtcattga cggcaaagag atcatgcctt gcgatccctc gaaaccagcg      1620
gtcatgacct tctatatccc gatgaatcaa gcgacacggg gcatgcctcg cggcgagcaa      1680
gcgatgaccg cccgccacat gcttttcaac ttgacgttcg cagatatcga actgctcatt      1740
cgggatcagc tcactcgtgc gttcggatct tatggatttg atgccaagcg ggacatcgct      1800
gccattgttg caaacaggtg gggacatgcg ctggtctgcg ccgggccagg attttacact      1860
gggcttaacg gcaaaccgcc cgtcagtaag gtgatcaccg ctggatggga ccgagtggca      1920
ttcgggcatt cggacctttc cggcagacaa gcatggaccg tggccgtaaa ttatgcacgg      1980
acagcggttg cgaatgtctt ccctaaaatc tga                                  2013

<210> SEQ ID NO 2
<211> LENGTH: 670
<212> TYPE: PRT
<213> ORGANISM: Methylobacterium Thebainfresser

<400> SEQUENCE: 2

Met Thr Glu Lys Thr Pro Lys Leu Gly Ser Glu Ala Ala Asn Lys Leu
1               5                   10                  15

Gly Leu Glu Ala Asp Ile Ser Arg Arg Asp Met Val Gly Gly Val Leu
            20                  25                  30

Ile Gly Ala Gly Ala Leu Leu Ala Ser Val Ala Pro Gly Ala Ile
        35                  40                  45

Asn Arg Ala Leu Ala Glu Gly Pro Ser Arg Leu Pro Pro Val Arg Gly
    50                  55                  60

Ser Gly Thr Gly Trp Arg Gly Ile Glu Ile Ala Asp Asp Trp Gln Gly
65                  70                  75                  80

Pro Gly Gly Ile Gly Asp Tyr Ser Lys Ser Asn Gly Asn Thr Gly Lys
                85                  90                  95

Val Ile Arg Asp Ala His Ala Gly Ile Arg Asn His Glu Phe Glu Lys
            100                 105                 110

Arg Leu Ala Thr Ala Ser Asp Val Asn Glu Lys Tyr Asp Val Ile Ile
        115                 120                 125

Val Gly Ala Gly Ile Ser Gly Leu His Ser Ala Tyr Asp Leu Leu Arg
    130                 135                 140

Gln Arg Pro Asn Ile Lys Ile Leu Met Leu Asp Asn His Ala Ile Phe
145                 150                 155                 160

Gly Gly Glu Ala Lys Gln Asn Lys Met Glu Val Asp Gly Gln Ala Leu
                165                 170                 175

Tyr Gly Gly Gln Gly Pro Thr Leu Tyr Ser Phe Val Gly Asp Asp Leu
            180                 185                 190

Pro Ser Trp Lys Gly Asn Pro Ala Leu Ala Ser Ile Met Glu Leu Lys
        195                 200                 205

Thr Tyr Pro Lys Glu Phe Gly Leu Pro Thr Glu Thr Thr Trp Ser Asp
    210                 215                 220

Lys Lys Thr Asp Val Lys Val Pro Val Asp Leu Trp Phe Ser Met Ala
225                 230                 235                 240

Ser Pro Ser Gln Thr Asp Ile Ala Tyr Arg Trp Glu Gly Ser Gly Leu
                245                 250                 255

Val Lys Asn Pro Leu Leu Asn Ser Phe Arg Asp Ala Pro Val Ser Gln
            260                 265                 270

Lys Ser Lys Asp Ala Ile Ala Leu Met Leu Ala Val Asp Asn Gly Ala
        275                 280                 285
```

Lys Arg Pro Val Glu Pro Val Gly Asp Val Ser Thr Trp Val Asp Asn
            290                 295                 300

Met Thr Tyr Ala Glu Phe Leu Lys Lys Val Tyr Gly Ala Asp Asp Glu
305                 310                 315                 320

Ala Val Gln Leu Val Asp Gln Ile Asp Val Val Gly Thr Ala Gly Leu
                325                 330                 335

Gly Gly Asp Val Phe Asn Ala Ser Leu Ala Ala Leu Gly Leu Asn Gln
            340                 345                 350

Tyr Gly Gly Ile Glu Leu Trp Asn Gly Gly Leu Gln Gly Leu Ser Leu
        355                 360                 365

Pro Thr Gly Asn Gly Gly Val Gly Arg Ser Ile Leu Arg Lys Phe Met
370                 375                 380

Pro Gly Ala Ile Lys Gly Gly Thr Ser Leu Thr Asp Thr Leu Phe Gly
385                 390                 395                 400

Asp Val Asn Trp Asp Val Leu Asp His Ala Asn Asn Val Arg Ile
                405                 410                 415

Arg Leu Asn Ser Thr Val Val Gly Val Gln Asn Asn Glu Thr Pro Thr
                420                 425                 430

Gly Thr Lys Asp Ala Thr Val Phe Phe Leu His Asp Asn Arg Leu Tyr
            435                 440                 445

Lys Ala Lys Gly Lys Ala Val Ile Met Gly Thr Pro Gln Gln Val Asn
450                 455                 460

Arg Asn Val Cys Leu Asn Leu Pro Asn His Leu Ser Glu Ala Met Gly
465                 470                 475                 480

Asp Phe His His Ala Pro Ile Leu Val Val Asn Val Ala Leu Arg Asn
                485                 490                 495

Trp Lys Ser Met Glu Lys Ala Gly Val Ser Gly Leu Arg Trp Phe Gly
            500                 505                 510

Glu Tyr Pro Gly Ile Gly Gln Ile Val Arg Ser Met Val Ile Asp Gly
        515                 520                 525

Lys Glu Ile Met Pro Cys Asp Pro Ser Lys Pro Ala Val Met Thr Phe
530                 535                 540

Tyr Ile Pro Met Asn Gln Ala Thr Arg Gly Met Pro Arg Gly Glu Gln
545                 550                 555                 560

Ala Met Thr Ala Arg His Met Leu Phe Asn Leu Thr Phe Ala Asp Ile
                565                 570                 575

Glu Leu Leu Ile Arg Asp Gln Leu Thr Arg Ala Phe Gly Ser Tyr Gly
            580                 585                 590

Phe Asp Ala Lys Arg Asp Ile Ala Ala Ile Val Ala Asn Arg Trp Gly
        595                 600                 605

His Ala Leu Val Cys Ala Gly Pro Gly Phe Tyr Thr Gly Leu Asn Gly
610                 615                 620

Lys Pro Pro Val Ser Lys Val Ile Thr Ala Gly Trp Asp Arg Val Ala
625                 630                 635                 640

Phe Gly His Ser Asp Leu Ser Gly Arg Gln Ala Trp Thr Val Ala Val
                645                 650                 655

Asn Tyr Ala Arg Thr Ala Val Ala Asn Val Phe Pro Lys Ile
            660                 665                 670

<210> SEQ ID NO 3
<211> LENGTH: 2013
<212> TYPE: DNA
<213> ORGANISM: Artificial Sequence
<220> FEATURE:

<223> OTHER INFORMATION: Synthetic

<400> SEQUENCE: 3

```
atgactgaga agacacctaa acttggatct gaggcagcta ataagttggg tttggaggct      60
gacatctcta ggagagatat ggtgggagga gtgcttatcg gtgcaggtgc tgctttgctt     120
gcatctgttg ctcctggtgc tatcaacagg gctcttgcag aaggaccatc aaggcttcct     180
ccagttagag gttcaggaac tggatggagg ggtattgaga ttgcagacga ctggcaagga     240
cctggaggaa tcggagatta ttctaagtct aacggtaaca ctggaaaggt gatcagggac     300
gctcacgctg gtatcaggaa ccatgagttc gaaagaggt tggctactgc ttctgacgtg      360
aacgagaagt acgacgtgat catcgtggga gctggtatct ctggacttca ctctgcatac     420
gatttgttga gacaaagacc taatattaaa attttaatgt ggacaaacca cgctatcttc     480
ggtggtgagg ctaagcagaa caagatggag gttgacggtc aggcattgta cggaggacag     540
ggaccaactc tttactcatt cgttggagac gatttgcctt catggaaggg aaaccctgct     600
ttggcatcta tcatgaact taagacatat ccaaaggagt tcggacttcc aactgagact      660
acttggtcag ataagaagac tgacgttaag gttccagtgg acctttggtt ctcaatggca     720
tcaccttcac agacagatat tgcttacagg tgggagggt ctggtttggt gaaaaatcct      780
ttgcttaact ctttcaggga tgctccagtt tctcagaagt caaaggatgc tatcgctttg     840
atgcttgcag tggacaacgg tgctaagaga cctgtgaaac tgttggaga cgtgtctaca      900
tgggtggaca acatgacata cgctgagttt ttgaagaagg tgtacggagc agatgatgag     960
gcagttcagt tggtggacca gatcgacgtt gtgggtacag ctggacttgg tggagacgtg    1020
ttcaacgcat cacttgctgc tttgggtttg aaccagtacg gtggaatcga gttgtggaac    1080
ggaggattgc agggtctttc tttgccaaca ggtaatggag gagtgggtag gtctatcctt    1140
aggaagttca tgcctggtgc tattaagggt ggaacatctt tgacagatac tcttttcggt    1200
gacgtgaact gggacgtttt ggatcacgca acaacaatg tgagaattag acttaattct     1260
acagtggttg gagtgcagaa caacgagact cctacaggaa caaagacgc tactgtgttt     1320
tttttgcatg acaatagact ttataaggct aagggaaaag ctgtgatcat gggaacacct    1380
cagcaggtga atagaaacgt ttgtcttaac cttccaaacc atctttctga ggctatgggt    1440
gacttccatc acgctccaat cttggtggtg aacgtggctc ttaggaactg gaaatctatg    1500
gaaaaggcag gagtgtcagg acttaggtgg tttggagagt accctggtat cggacagatc    1560
gttaggtcta tggtgattga tggaaaggag attatgccat gcgacccttc taagccagct    1620
gttatgacat tttacattcc tatgaatcaa gctactaggg gaatgccaag aggagagcag    1680
gctatgactg ctaggcacat gcttttcaat cttactttcg ctgatattga gttgcttatc    1740
agggaccagt tgactagggc tttcggttct tacggtttcg acgctaagag ggacattgct    1800
gctatcgtgg ctaacagatg gggtcatgct ttggtttgcg ctggtcctgg attctacact    1860
ggacttaacg gaaagcctcc agtgtcaaag gtgatcacac ctggatggga cagagtggct    1920
tttggacatt cagacttgtc aggaaggcag gcttggacag ttgctgtgaa ctacgctagg    1980
acagcagtgg ctaacgtttt ccctaagata tga                                 2013
```

<210> SEQ ID NO 4
<211> LENGTH: 25
<212> TYPE: DNA
<213> ORGANISM: Artificial Sequence
<220> FEATURE:
<223> OTHER INFORMATION: Synthetic

```
<400> SEQUENCE: 4
ccgatctatg acgggatatc tggga                                              25

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
tgacgcgaca atccctctac c                                                  21

<210> SEQ ID NO 6
<211> LENGTH: 31
<212> TYPE: DNA
<213> ORGANISM: Artificial Sequence
<220> FEATURE:
<223> OTHER INFORMATION: Synthetic

<400> SEQUENCE: 6
caccatatga ctgaaaaaac gcctaaacta g                                       31

<210> SEQ ID NO 7
<211> LENGTH: 37
<212> TYPE: DNA
<213> ORGANISM: Artificial Sequence
<220> FEATURE:
<223> OTHER INFORMATION: Synthetic

<400> SEQUENCE: 7
gaggaattct cagattttag ggaagacatt cgcaacc                                 37

<210> SEQ ID NO 8
<211> LENGTH: 32
<212> TYPE: DNA
<213> ORGANISM: Artificial Sequence
<220> FEATURE:
<223> OTHER INFORMATION: Synthetic

<400> SEQUENCE: 8
atggtaccta gggtacgtaa gtacgtactc aa                                      32

<210> SEQ ID NO 9
<211> LENGTH: 37
<212> TYPE: DNA
<213> ORGANISM: Artificial Sequence
<220> FEATURE:
<223> OTHER INFORMATION: Synthetic

<400> SEQUENCE: 9
cactcacgga ccgaagtcat gaagaacctg ataagac                                 37
```